(12) United States Patent
Payne et al.

(10) Patent No.: US 10,644,242 B2
(45) Date of Patent: May 5, 2020

(54) OLIGOMERIC PERYLENE DIIMIDE NON-FULLERENE ACCEPTORS VIA DIRECT (HETERO)ARYLATION CROSS-COUPLING REACTIONS

(71) Applicant: UTI Limited Partnership, Calgary (CA)

(72) Inventors: Abby-Jo Payne, Calgary (CA); Gregory C. Welch, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 0 days.

(21) Appl. No.: 16/562,829

(22) Filed: Sep. 6, 2019

(65) Prior Publication Data
US 2020/0083457 A1 Mar. 12, 2020

Related U.S. Application Data

(60) Provisional application No. 62/728,462, filed on Sep. 7, 2018.

(51) Int. Cl.
| | |
|---|---|
| C07D 519/00 | (2006.01) |
| H01L 51/00 | (2006.01) |
| H01L 51/42 | (2006.01) |
| H01L 51/05 | (2006.01) |

(52) U.S. Cl.
CPC ........ H01L 51/0053 (2013.01); C07D 519/00 (2013.01); H01L 51/0074 (2013.01); H01L 51/0558 (2013.01); H01L 51/4253 (2013.01)

(58) Field of Classification Search
CPC .............. C07D 519/00; H01L 51/0053; H01L 51/0558; H01L 51/4253
See application file for complete search history.

(56) References Cited

U.S. PATENT DOCUMENTS
9,865,819 B2   1/2018   Hendsbee et al.

FOREIGN PATENT DOCUMENTS
CN       107286157 A    10/2017

OTHER PUBLICATIONS

Luo et al., 6(5) J. Mat. Chem. C., 1136-1142 (2018) (Year: 2018).*
Bohra et al. (May 2017) "Direct C—H arylation: a "Greener" approach towards facile synthesis of organic semiconducting molecules and polymers," J. Mater. Chem. A 5(23): 11550-11571.
Bura et al. (2016) "Direct (Hetero)arylation Polymerization: Trends and Perspectives," J. Am. Chem. Soc. 138(32): 10056-10071.
Burke et al. (2013) "Green chemistry for organic solar cells," Energy Environ. Sci. 6: 2053-2066.
Cann et al. (Nov. 2017) "Spectroscopic Engineering toward Near-Infrared Absorption of Materials Containing Perylene Diimide," ChemPlusChem. 82(11):1359-1364.
Centore et al. (2012) "Perylene Diimides Functionalized with N-Thiadiazole Substituents: Synthesis and Electronic Properties in OFET Devices," Org. Electron. 13:2083-2093.
Chang et al. (Dec. 2017) "Rational design of two-dimensional PDI-based small molecular acceptor from extended indacenodithiazole core for organic solar cells," Dyes and Pigments 147: 31-39.
Chen et al. (2015) "A Perylene Diimide (PDI)-Based Small Molecule with Tetrahedral Configuration as a Non-Fullerene Acceptor for Organic Solar Cells," J. Mater. Chem. C. 3:4698-4705.
Cheng et al. (publicly available Feb. 2018) "Next-generation organic photovoltaics based on non-fullerene acceptors," Nat. Photonics (Mar. 2018) 12: 131-142.
Chochos et al. (2013) "Rational Design on N-Type Organic Materials for High Performance Organic Photovoltaics," RSC Adv. 3:7160-7181.
Dayneko et al. (publicly available Apr. 2018) "Combining Facile Synthetic Methods with Greener Processing for Efficient Polymer-Perylene Diimide Based Organic Solar Cells," Small Methods 2(6): 1800081 (published Jun. 2018), 9 pp.
Eftaiha et al. (2014) "Recent advances of non-fullerene, small molecular acceptors for solution processed bulk heterojunction solar cells," J. Mater. Chem. A 2(5): 1201-1213.
Fernandez-Lazaro et al. (2016) "Perylenediimides as Non-Fullerene Acceptors in Bulk-Heterojunction Solar Cells (BHJSCs)," J. Mater. Chem. A. 4:9336-9346.
Grenier (Jan. 2017) "Robust Direct (Hetero)arylation Polymerization in Biphasic Conditions," J. Am. Chem. Soc. 139(7): 2816-2824.
Hendsbee et al. (2016) "Synthesis, Self-Assembly, and Solar Cell Performance of N-Annulated Perylene Diimide Non-Fullerene Acceptors," Chem. Mater. 28(19): 7098-7109.
Hendsbee et al. (Mar. 2017) "N-annulated perylene diimide dimers: the effect of thiophene bridges on physical, electronic, optical, and photovoltaic properties," Sustainable Energy & Fuels. 1:1137-1147.
Hou et al. (publicly available Jan. 2018) "Organic solar cells based on non-fullerene acceptors," Nat. Mater. (Feb. 2018) 17: 119-128.
Kozma et al. (2013) "Perylene Diimides Based Materials for Organic Solar Cells," Dyes Pigm. 98:160-179.
Li et al. (2016) "A non-fullerene acceptor with a fully fused backbone for efficient polymer solar cells with a high open-circuit voltage," J. Mater. Chem. A 4(39): 14983-14987.

(Continued)

Primary Examiner — Timothy R Rozof
(74) Attorney, Agent, or Firm — Leydig, Voit & Mayer, Ltd.

(57) ABSTRACT

Oligomeric compounds useful as organic conjugated materials in electronic devices. Oligomeric compounds contain three or more or four or more of certain PDI units bonded to an organic core. The organic core contains one, two or more thiophene rings. The organic core can contain two or more thiophene rings separated by a linker group; two or more thiophene rings directly fused to each other or indirectly fused to each other through an optionally substituted aromatic or non-aromatic carbocylic ring system or an optionally substituted aromatic heterocyclic or non-aromatic heterocyclic ring system; or each of two or more thiophene rings is fused to an aromatic or non-aromatic carbocylic ring system or an aromatic heterocyclic or non-aromatic heterocyclic ring system and the resulting fused rings containing a thiophene ring are each separated by a linker group M. Methods for making oligomeric compounds by direct heteroarylation are provided.

28 Claims, 8 Drawing Sheets

(56) References Cited

OTHER PUBLICATIONS

Li et al. (2016) Electronic Supplementary Information for "A non-fullerene acceptor with a fully fused backbone for efficient polymer solar cells with a high open-circuit voltage," J. Mater. Chem. A 4(39): 14983-14987, pp. 1-9.
Li et al. (2016) "Structural effects of dibromocarbazoles on direct arylation polycondensation with 3,4-ethylenedioxythiophene," Polym. Chem. 7: 3165-3171.
Lin et al. (2014) "A Star-Shaped Perylene Diimide Electron Acceptor for High-Performance Organic Solar Cells," Adv. Mater. 26:5137-5142.
Lin et al. (2014) "A Twisted Dimeric Perylene Diimide Electron Acceptor for Efficient Organic Solar Cells," Adv. Energy Mater. 4(13): 1400420, pp. 1-5.
Lin et al. (2014) Supporting Information for "A Twisted Dimeric Perylene Diimide Electron Acceptor for Efficient Organic Solar Cells," 1-9.
Lin et al. (2014) "Non-Fullerene Acceptors for Organic Photovoltaics: An Emerging Horizon," Mater. Horiz. 1(5): 470-488.
Lin et al. (2015) "An Electron Acceptor Challenging Fullerenes for Efficient Polymer Solar Cells," Adv. Mater. 27(7): 1170-1174.
Liu et al. (2016) "Fast charge separation in a non-fullerene organic solar cell with a small driving force," Nat. Energy 1: 16089(1)-16089(7).
Liu et al. (2016) "Non-fullerene small molecule acceptors based on perylene diimides," J. Mater. Chem. A. 4:17604-17622.
Lombeck et al. (Jul. 2017) "To branch or not to branch: C—H selectivity of thiophene-based donor—acceptor—donor monomers in direct arylation polycondensation exemplified by PCDTBT," Polym. Chem. 8(32): 4738-4745.
Luo et al. (Jan. 2018) "A three-dimensional thiophene-annulated perylene bisimide as a fullerene-free acceptor for a high performance polymer solar cell with the highest PCE of 8.28% and a Voc over 1.0 V," J. Mater. Chem. C 6(5): 1136-1142.
Marrocchi et al. (2016) "Current Methodologies for a Sustainable Approach to [Capital Pi]—Conjugated Organic Semiconductors," Energy Environ. Sci. 9:763-786.
McAfee et al. (2015) "Key components to the recent performance increases of solution processed non-fullerene small molecule acceptors," J. Mater. Chem. A 3(32): 16393-16408.
McAfee et al. (2015) "Utility of a Heterogeneous Palladium Catalyst for the Synthesis of a Molecular Semiconductor via Stille, Suzuki, and Direct Heteroarylation Cross-Coupling Reactions," RSC Adv. 5:26097-26106.
McAfee et al. (Jan. 2017) "Simply Complex: The Efficient Synthesis of an Intricate Molecular Acceptor for High-Performance Air-Processed and Air-Tested Fullerene-Free Organic Solar Cells," Chem. Mater. 29:1309-1314.
McAfee et al. (Feb. 2017) "Applying direct heteroarylation synthesis to evaluate organic dyes as the core component in PDI-based molecular materials for fullerene-free organic solar cells," J. Mater. Chem. A 5(23): 11623-11633.
McAfee et al. (Jun. 2017) "A non-fullerene acceptor with a diagnostic morphological handle for streamlined screening of donor materials in organic solar cells," J. Mater. Chem. A. 5:16907-16913.
McAfee et al. (Jun. 2019) "Development of Organic Dye-Based Molecular Materials for Use in Fullerene-Free Organic Solar Cells," Chem. Rec. 19(6): 989-1007.
Meng et al. (2016) "High-Performance Solution-Processed Non-Fullerene Organic Solar Cells Based on Selenophene-Containing Perylene Bisimide Acceptor," J. Am. Chem. Soc. 138(1): 375-380.
Payne et al. (Aug. 2017) "An unsymmetrical non-fullerene acceptor: synthesis via direct heteroarylation, self-assembly, and utility as a low energy absorber in organic photovoltaic cells," Chem. Commun. 53(73): 10168-10171.
Payne et al. (publicly available Dec. 2017) "Optoelectronic engineering with organic dyes: utilizing squaraine and perylene diimide to access an electron-deficient molecule with near-IR absorption," Chemical Papers 2018 72(7): 1629-1634.
Payne et al. (Sep. 2018) "A tetrameric perylene diimide non-fullerene acceptor via unprecedented direct (hetero)arylation cross-coupling reactions," Chem. Commun. 54(81): 11443-11446.
Payne et al. (Sep. 2018) Supporting Information for "A tetrameric perylene diimide non-fullerene acceptor via unprecedented direct (hetero)arylation cross-coupling reactions," Chem. Commun. 54(81): 11443-11446, pp. S1-S16.
Pouliot et al. (2016) "Direct (Hetero)arylation Polymerization: Simplicity for Conjugated Polymer Synthesis," Chem. Rev. 116(22): 14225-14274.
Rajasingh et al. (2007) "Selective Bromination of Perylene Diimides under Mild Conditions," J. Org. Chem. 72:5973-5979.
Rudenko et al. (2015) "Optimization of direct arylation polymerization (DArP) through the identification and control of defects in polymer structure," J. Polym. Sci. Part A: Polym. Chem. 53: 135-147.
Schipper et al. (2011) "Direct Arylation as a Synthetic Tool for the Synthesis of Thiophene-Based Organic Electronic Materials," Chem. Mater. 23(6): 1594-1600.
Sun et al. (2015) "Non-Fullerene-Acceptor-Based Bulk-Heterojunction Organic Solar Cells with Efficiency over 7%," J. Am. Chem. Soc. 137(34): 11156-11162.
Urieta-Mora et al. (Apr. 2019) "Saddle-like, Π-conjugated, cyclooctatetrathiophene-based, hole-transporting material for perovskite solar cells," J. Mater. Chem. C 7(22): 6656-6663.
Vespa et al. (Jul. 2018) "Synthesis of a Perylene Diimide Dimer with Pyrrolic N—H Bonds and N-Functionalized Derivatives for Organic Field-Effect Transistors and Organic Solar Cells," Eur. J. Org. Chem. 4592-4599.
Wadsworth et al. (publicly available Apr. 2018) "Critical review of the molecular design progress in non-fullerene electron acceptors towards commercially viable organic solar cells," Chem. Soc. Rev. (2019) 48, DOI:10.1039/C7CS00892A, pp. 1596-1625.
Welsh et al. (Apr. 2018) "Direct (Hetero)Arylation for the Synthesis of Molecular Materials: Coupling Thieno[3,4-c]pyrrole-4,6 dione with Perylene Diimide to Yield Novel Non-Fullerene Acceptors for Organic Solar Cells," Molecules 23(4): 931, pp. 1-17.
Welsh et al. (May 2019) "Synthesis of aromatic imide tetramers relevant to organic electronics by direct (hetero)arylation," New J. Chem. 43(24): 9333-9337.
Wu et al. (2016) "Covalently Bound Clusters of Alpha-Substituted PDI—Rival Electron Acceptors to Fullerene for Organic Solar Cells," J. Am. Chem. Soc. 138(23): 7248-7251.
Wu et al. (Jan. 2017) "Propeller-Shaped Acceptors for High-Performance Non-Fullerene Solar Cells: Importance of the Rigidity of Molecular Geometry," Chem. Mater. 29(3): 1127-1133.
Yan et al. (2013) "Towards Rational Design of Organic Electron Acceptors for Photovoltaics: A Study Based on Perylenediimide Derivatives," Chem. Sci. 4:4389-4394.
Yan et al. (Feb. 2018) "Non-fullerene acceptors for organic solar cells," Nat. Rev. Mater. 3: 18003, pp. 1-19.
Zhan et al. (2007) "A High-Mobility Electron-Transport Polymer with Broad Absorption and Its Use in Field-Effect Transistors and All-Polymer Solar Cells," J. Am. Chem. Soc. 129:7246-7247.
Zhan et al. (2015) "New Advances in Non-Fullerene Acceptor Based Organic Solar Cells," RSC Adv. 5:93002-93026.
Zhan et al. (2016) "More than Conformational 'Twisting' or 'Coplanarity': Molecular Strategies for Designing High-Efficiency Nonfullerene Organic Solar Cells," Chem. Mater. 28: 1948-1964.
Zhang et al. (2014) "Non-Fullerene Organic Solar Cells with 6.1% Efficiency through Fine-Tuning Parameters of the Film—Forming Process," Chem. Mater. 27:166-173.
Zhang et al. (2015) "A Selenophenyl Bridged Perylene Diimide Dimer as an Efficient Solution—Processable Small Molecule Acceptor," Chem. Commun. 51:1058-1061.
Zhang et al. (2016) "High-Efficiency Nonfullerene Polymer Solar Cell Enabling by Integration of Film—Morphology Optimization, Donor Selection, and Interfacial Engineering," ACS Appl. Mater. Interfaces. 8: 15415-15421.

(56) References Cited

OTHER PUBLICATIONS

Zhang et al. (Nov. 2017) "Ring-Fusion of Perylene Diimide Acceptor Enabling Efficient Nonfullerene Organic Solar Cells with a Small Voltage Loss," J. Am. Chem. Soc. 139(45): 16092-16095.

Zhang et al. (publicly available Jul. 2018) "Material insights and challenges for non-fullerene organic solar cells based on small molecular acceptors," Nat. Energy (Sep. 2018) 3: 720-731.

Zhao et al. (2015) "High-Efficiency Non-Fullerene Organic Solar Cells Enabled by a Difluorobenzothiadiazole-Based Donor Polymer Combined with a Properly Matched Small Molecule Acceptor," Energy Environ. Sci. 8:520-525.

Zhao et al. (2016) "Fullerene-Free Polymer Solar Cells with over 11% Efficiency and Excellent Thermal Stability," Adv. Mater. 28(23): 4734-4739.

Zhao et al. (2016) "Electron Acceptors Based on α-Substituted Perylene Diimide (PDI) for Organic Solar Cells," Chem. Mater. 28:1139-1146.

\* cited by examiner

OLIGOMERIC PERYLENE DIIMIDE NON-FULLERENE ACCEPTORS VIA DIRECT (HETERO)ARYLATION CROSS-COUPLING REACTIONS

CROSS-REFERENCE TO RELATED APPLICATION

This application claims the benefit of U.S. provisional application 62/728,462, filed Sep. 7, 2018, which is incorporated by reference herein in its entirety.

BACKGROUND

The invention relates to the synthesis of thiophene-based core perylene diimide tetramers, hexamers, octamers or higher oligomers via a unique direct heteroarylation (DHA). Certain thiophene-based core structures are functionalized with four or more perylene diimides at active C—H positions in the core. The methods herein provide simple synthetic pathways to tetrameric and higher oligomeric perylene diimides, which are useful, at least, as electron acceptors for organic solar cells. The invention further relates to the PDI tetramers, hexamers, octamers and higher oligomers that are readily prepared by this new method.

Organic conjugated materials are useful in an array of applications ranging from photovoltaics to cancer cell imaging.[1-3] Interest in these materials stems from the ability to alter the chemical structure to fine tune materials properties.[4-7] In addition, the ability to render organic conjugated materials soluble has led to major advances in the field of printed electronics.[8] The development of practical organic building blocks and synthetic methods from which to construct organic materials suitable for large scale manufacturing is an active area of study.[9-11] With respect to the latter, the direct (hetero)arylation (DHA) reaction has emerged as one of the most useful coupling protocols to make new polymeric and molecular organic materials in a greener fashion.[12-15] Direct CH bond functionalization eliminates the need for incorporation of directing groups and allows for previously unavailable substrates to be utilized.

Specifically, for organic materials, their use as active materials in organic solar cells (OSCs) has been widely studied. In this application, the organic materials harvest the energy of photons, create free charge carriers and transport charges to electrodes.[17] Within the field of OSCs, the development of non-fullerene acceptors (NFAs) has been of significant recent interest.[18-23]

Two classes of NFAs based upon perylene diimides (PDI) and indancenodithiophene (IDT) building blocks have so far emerged as candidates for delivering good performance OSCs. The IDT based NFAs have an IDT core flanked with planar, electron withdrawing end caps, with the entire molecule rendered electron accepting.[24,25] The IDT core is insulated with bulky side chains and serves to shuttle electrons within the molecule, while the endcaps drive self-assembly and facilitates electron transfer. The molecules typically adopt a very planar geometry.

In contrast, PDI-based NFAs are multi-chromophore in nature and the best performing materials have highly twisted geometries to prevent strong aggregation of the PDIs, allowing for appropriate phase separation within the active layer films.[26-28] Many of the better performing materials are dimeric in nature, but an emerging trend has been to construct tetrameric PDI NFAs.[29-32] We note in particular that a fused ring PDI-tetramer (FTTB-PDI4) with PDI units ring-fused to a tetrathienylbezene is currently the best performing material to our knowledge.[45]

U.S. Pat. No. 9,865,819 relates to certain nitrogen annulated perylene diimides useful as electron transport materials in organic electronic devices. In one aspect, the patent relates to N-annulated PDI compounds of formula:

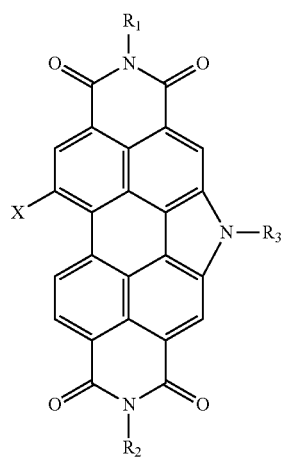

where:

X is halogen (F, Cl, Br or I), triflyl, tosyl, or mesyl;

$R_1$ and $R_2$ are independently straight-chain or branched alkyl groups having 1-30 carbon atoms; and $R_3$ is a straight-chain or branched alkyl group having 1-30 carbon atoms. These compounds are at least employed to prepare PDI dimers of formula:

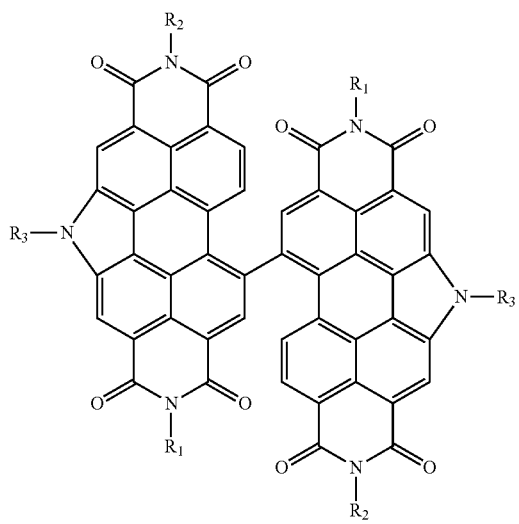

The patent also relates to PDI dimer compounds of formula:

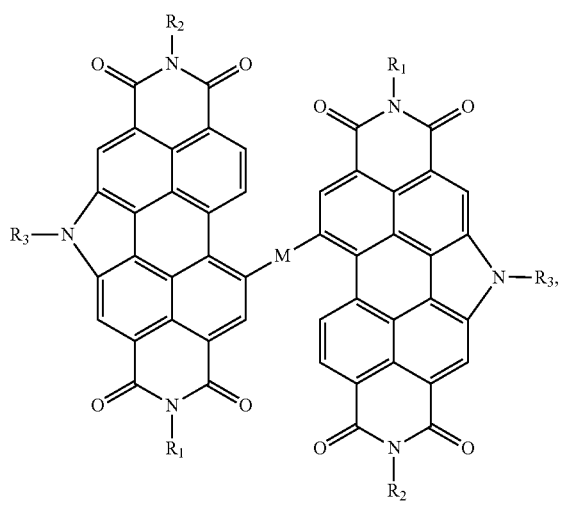

where M is certain divalent linking moieties selected from an arylene, a heteroarylene, an alkynylene, a dialkynlyene, an organic dye or M is and

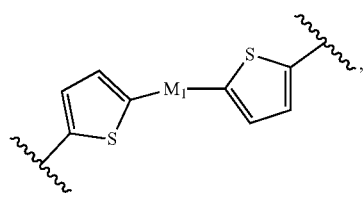

where $M_1$ is arylene, a heteroarylene, or an organic dye molecule, and to compounds of formula:

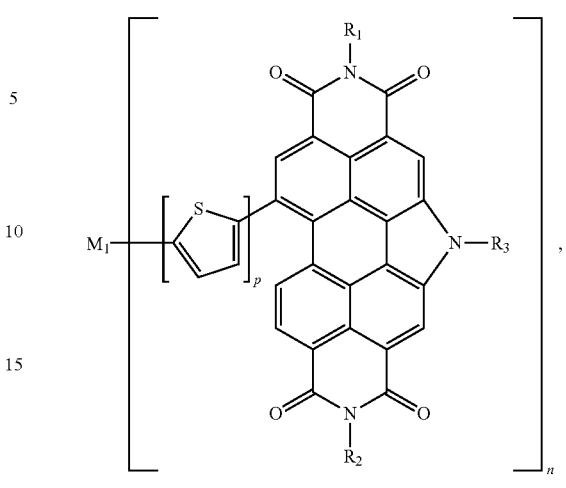

where:

p is 0 or 1, n is 2, 3 or 4, and $M_1$ is arylene, a heteroarylene, or an organic dye molecule and M 1 groups do not contain thiophene groups. This patent is incorporated by reference herein in its entirety for definitions of groups listed in formulas therein, for methods of synthesis of compounds therein as well as for descriptions of applications of the PDI compounds and descriptions of electronic devices therein.

DHA Reactivity with NPDI-Br:

has been extended with various coupling partners including diketopyrrolopyrrole[37,38] (DPP), isoindigo[37] (II), thienyl isoindigo[37] (II-TH), squaraine[39], and thieno[3,4-c]pyrrole-4,6-dione (TPD)[40]. The inventors are not aware of any report of using DHA for couplings with IDT.

PDI and IDT coupling via Stille coupling have been reported previously and to require silica-gel column chromatography purification.[34-36] The PDI dimer, IDT-2PDI:

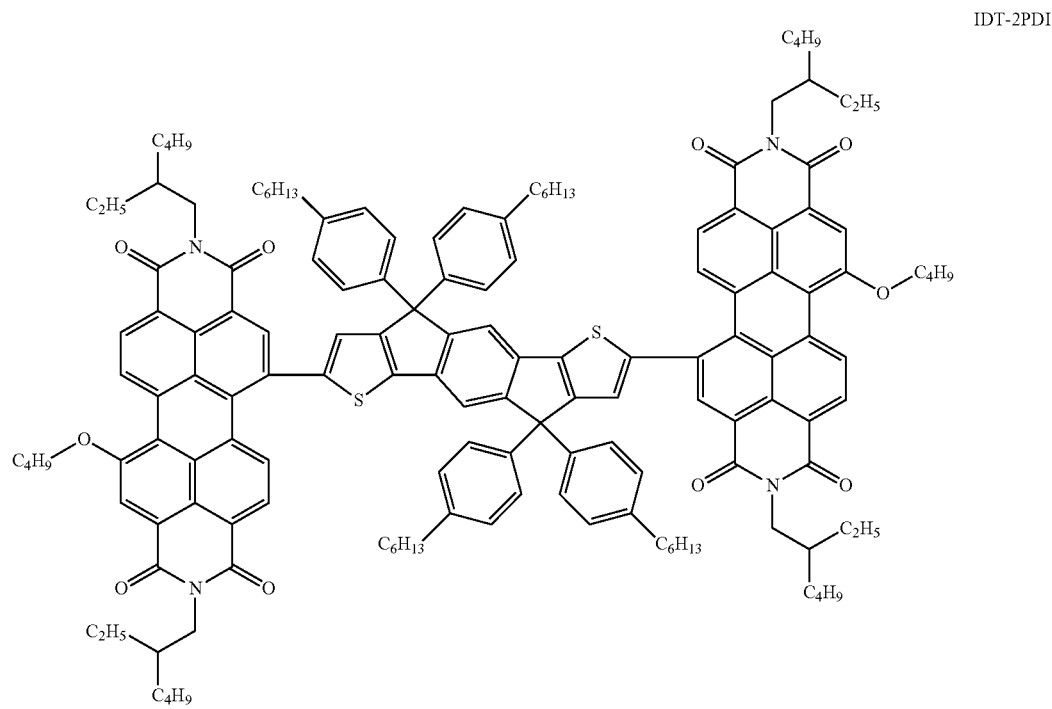
was reported prepared in 78% yield by reaction of the trimethyl tin IDT derivative:
with 2× of the PDI starting material:
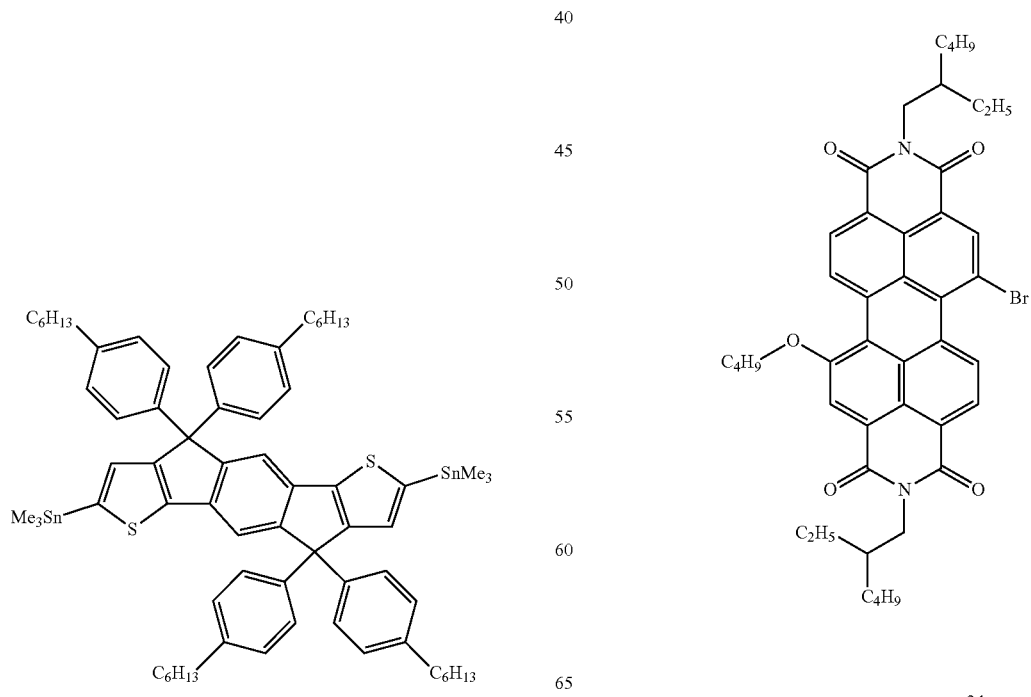
with Pd(PPh$_3$)$_4$ in toluene (110° C.)[34]. The structurally related PDI dimer:

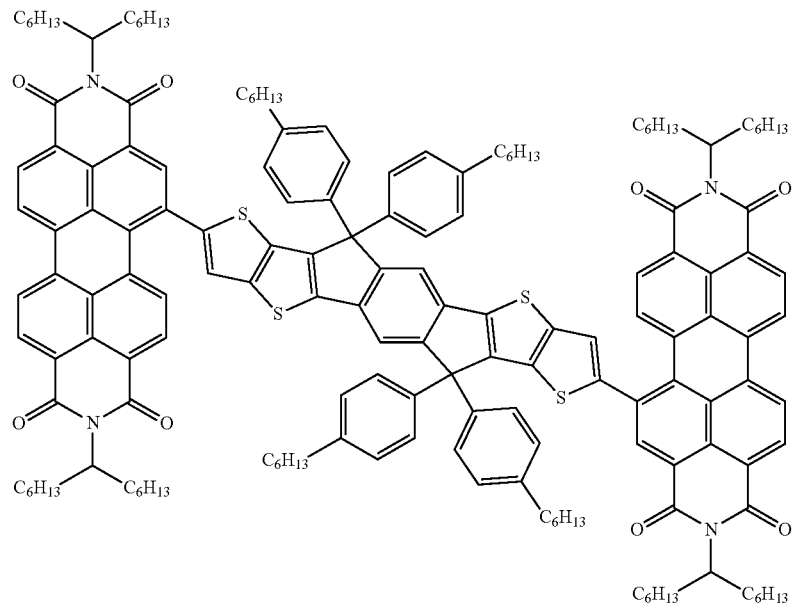
was reported prepared by an analogous method.[35]
PDI Dimers of Formula:
30
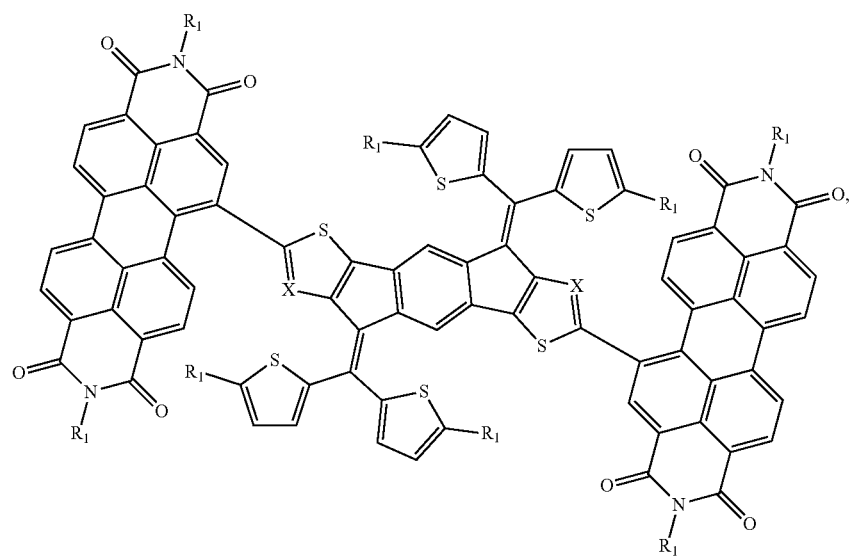

where:
X is C or N and $R_1$ is 2-ethylhexyl are reported by Chang et al.[36] References 34, 35 and 36 are each incorporated by reference herein in its entirety herein for description of methods for characterization of materials and preparation of electronic devices using these materials.

CN107286157 published Oct. 24, 2017 appears to report the synthesis of certain PDI tetramers having a core of 3,3'-bithiophene of structure:

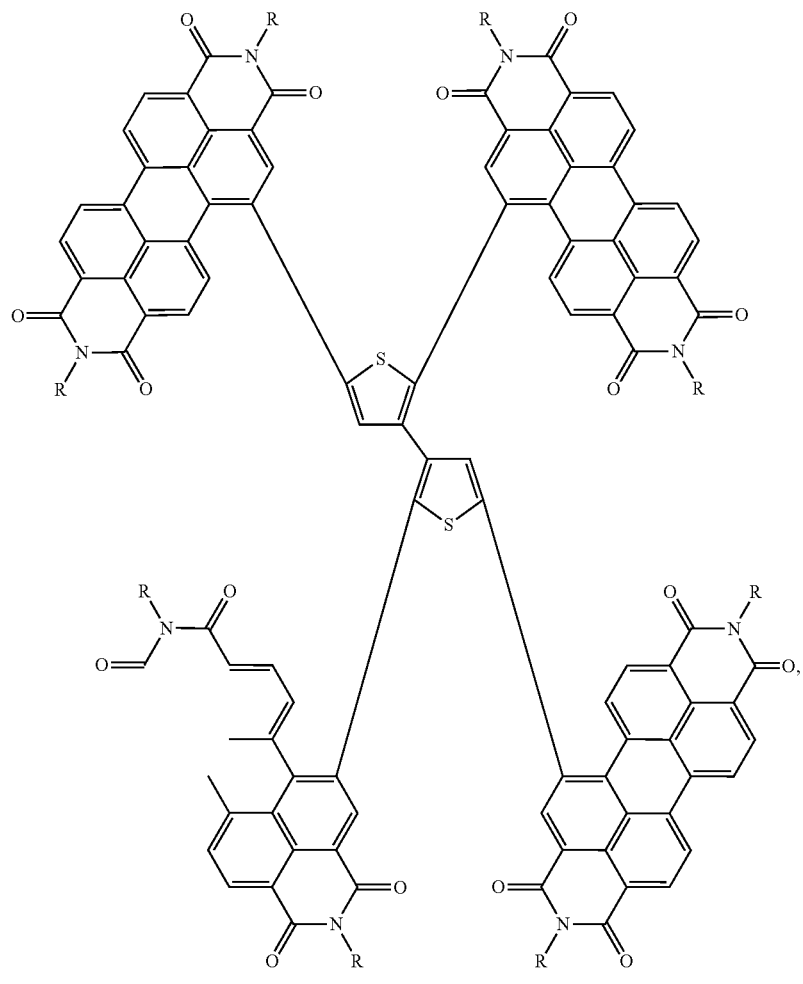

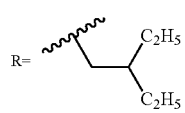

where R is various branched alkyl groups. The document also includes tetramers of structure:

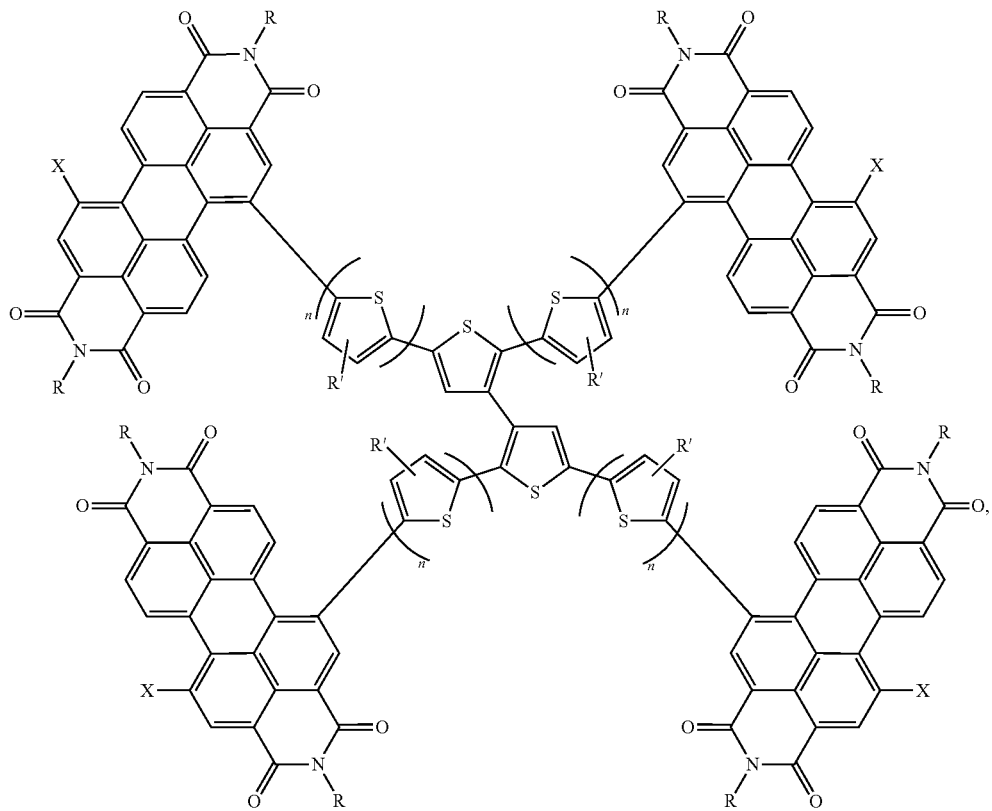

where:
n is 0, 1 or 2; R is an alkyl with 5-30 carbon atoms, R' is H or an alkyl with 1-15 carbon atoms and X is H, CN or alkoxy having 1-10 carbon atoms. Tetramer cores:

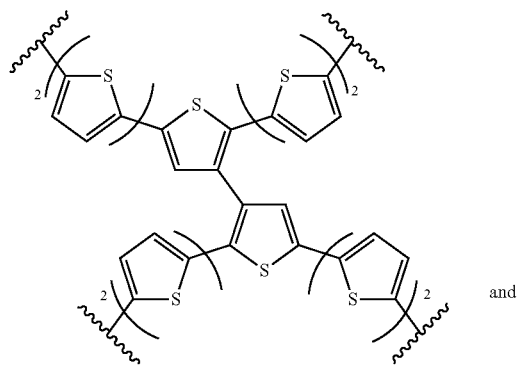

and

-continued

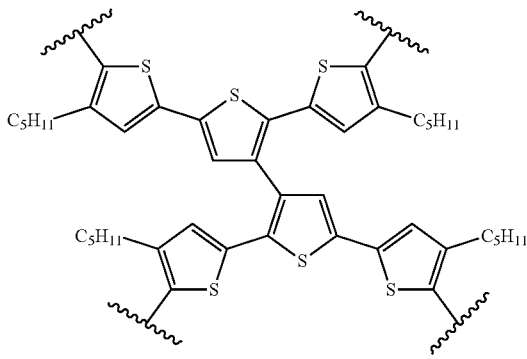

are more specifically described therein. This document is incorporated by reference herein in its entirety for descriptions of various tetramers and for support for optional exclusion of certain cores from claims herein.

This invention extends the DHA coupling method to reaction of N-annulated PDI derivatives and related PDI derivatives with certain thiophene-based cores, such as IDT, to prepare new N-annulated PDI tetrameric, hexameric, octameric and higher oligomeric structures. The resulting PDI tetramers and higher oligomers function as non-fullerene acceptors providing OSCs with high open-circuit voltages preferably greater than 1V.

SUMMARY

In one aspect, the invention relates to compounds useful as organic conjugated materials in electronic devices that contain four or more of certain PDI units bonded to an organic core. In a specific embodiment, the organic core contains one or more thiophene rings and more preferably contains two or more thiophene rings. In a specific embodiment, the PDI oligomeric compounds are prepared by direct heteroarylation.

In a specific embodiment, the oligomeric compound has the generic structure I:

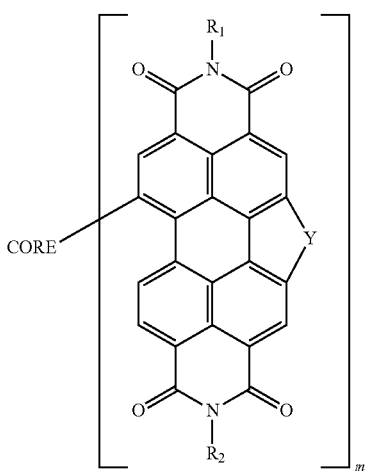

where:
m is an integer of 4 or higher and more specifically is an integer from 4-10, and yet more specifically is 4, 6, 8 or 10;
Y is S, Se or N—$R_3$, where each $R_3$ in the molecule is independently selected from an alkyl, aryl or arylalkyl; and each $R_1$ and each $R_2$ is independently selected from straight-chain or branched alkyl groups having 1-30 carbon atoms, or more preferably 3-20 carbon atoms, or yet more preferably 6-12 carbon atoms.

In a specific embodiment, all PDI moieties in the compound are the same. In a specific embodiment, $R_1$ and $R_2$ are alkyl groups having 6-12 carbon atoms and Y is N—$R_3$, where $R_3$ is an alkyl group having 6-12 carbon atoms.

In a specific embodiment, m is 4 and the oligomeric compound is a PDI tetramer. In a specific embodiment, m is 6 and the oligomeric compound is a PDI hexamer. Scheme 1B illustrates an exemplary synthesis of a PDI tetramer with an IDT core.

In specific embodiments, the oligomeric compounds have four or more PDI groups therein, each of which is bonded to a core structure containing at least two thiophene rings, wherein:

(1) the two or more thiophene rings are separated by a linker group M;
(2) the two or more thiophene rings are directly fused to each other or indirectly fused to each other through an optionally substituted aromatic or non-aromatic carbocylic ring system or an optionally substituted aromatic heterocyclic or non-aromatic heterocyclic ring system; or
(3) each of two or more thiophene rings is fused to an aromatic or non-aromatic carbocylic ring system or an aromatic heterocyclic or non-aromatic heterocyclic ring system and the resulting fused rings containing a thiophene ring are each separated by a linker group M.

The linker M can be a single bond, a double bond, or a divalent or trivalent linker comprising an alkylene (—$(CH_2)_x$—), an alkenylene (e.g., —CH═CH—), a dialkenylene (e.g., —CH═CH—CH═CH—), an alkynylene (e.g., —C≡C—), a dialkynylene (—C≡C—C≡C—), or an optionally substituted aromatic or non-aromatic carbocyclic or heterocyclic ring system. In specific embodiments, M is an arylene or a heteroarylene. In specific embodiments, M is a moiety as illustrated in Scheme 2.

In specific embodiments, the CORE is a moiety C1-C40 as illustrated in Scheme 3, where:
each $R_4$ is independently selected from H, an alkyl or alkoxy group having 1-30 carbon atoms, an optionally substituted aryl or heteroaryl group, where optional substitution is substitution with one or more halogen, CN, alkyl or alkoxy having 1-30 carbon atoms, 1-12 carbon atoms, 3-12 carbon atoms, 6-12 carbon atoms or 1-3 carbon atoms;
each $R_5$ is independently selected from hydrogen, halogen, CN, or alkyl or alkoxy having 1-30, 1-12, 3-12, 6-12 or 1-3 carbon atoms;
each $R_6$ is independently selected from hydrogen, halogen, CN, an optionally substituted phenyl or benzyl or an alkyl or alkoxy having 1-30, 1-12, 3-12, 6-12 or 1-3 carbon atoms;
each $R_7$ is independently selected from hydrogen, halogen, CN, an optionally substituted phenyl or benzyl or an alkyl or alkoxy having 1-30, 1-12, 3-12, 6-12 or 1-3 carbon atoms; and
$R_N$ is selected from hydrogen, an alkyl group having 1-30, 1-12, 3-12, 6-12 or 1-3 carbon atoms, an aryl group or an arylalkyl group. For CORES of Scheme 3, aryl groups include phenyl and naphthyl groups, among others, and arylalkyl groups include benzyl and phenethyl groups.

In specific embodiments, each $R_7$ is independently hydrogen or halogen or yet more specifically, each $R_7$ is independently hydrogen or fluorine. In specific embodiments, each $R_N$ is hydrogen or an alkyl group having 1-12 carbon atoms or an alkyl group having 1-3 carbon atoms.

More specifically, the CORE is:
(a) the moiety C1, C2, C6 or C7;
(b) the moiety C3, C4 or C5;
(c) the moiety C8, C9 or C35;
(d) the moiety C10 or C11;
(e) the moiety C12;
(f) the moiety C13;
(g) the moiety C14, C15 or C16;
(h) the moiety C17 or C18;
(i) the moiety C19a (Y is C), C19b (Y is P), C19c (Y is N), C19d (Y is S), C19e (Y is Si), or C19f(Y is Ge);
(j) the moiety C19a, C19c or C19d);
(k) the moiety C20a, C20b or C20c;
(l) the moiety C21, C23 or C24;
(m) the moiety C22 or C25;
(n) the moiety C26 or C27;
(o) the moiety C28 or C29;
(p) the moiety C30, C31, C32, or C33;
(q) the moiety C34 or C36;
(r) the moiety C37;
(s) the moiety C38;
(t) the moiety C39; or
(u) the moiety C40.

The invention additionally relates to an electronic device employing an electron acceptor wherein the electron acceptor is one or more PDI oligomeric compounds herein. More specifically, the disclosure provides an organic solar cell employing an electron acceptor wherein the electron acceptor is one or more PDI oligomeric compounds herein. More specifically the disclosure provides an organic thin film transistor employing an electron acceptor wherein the electron acceptor is one or more PDI oligomeric compounds herein. More specifically, the disclosure provides a redox flow battery, which comprises one or more PDI oligomeric compounds herein.

In another aspect, the invention relates to a method for making oligomeric PDI compounds, and more specifically for making PDI tetramers, hexamers and higher oligomers. The method reacts a core carrying 4 or more active C—H bonds with 2 or more equivalents (with respect to the core) of a PDI precursor and more preferably with 4 or more equivalents of a PDI precursor in an appropriate solvent in which the reactants (core and PDI precursor) are at least partially soluble, in the presence of a palladium catalyst, a proton shuttle and carbonate base.

The reaction is preferably carried out at a temperature of 70° C. or higher, dependent at least in part upon the solvent employed, and is preferably carried out at above ambient room pressure in a sealed vessel under an inert atmosphere (e.g., $N_2$). More preferably, the reaction is carried out at a temperature of 80° C. or higher. More preferably, the reaction is carried out at a temperature of 100° C. of higher. In specific embodiments, the precipitated oligomeric reaction product is washed with appropriate solvent to remove partially reacted products, such as dimers and trimers.

Other aspects of the disclosure will be apparent to one of ordinary skill in the art in view of the following detailed description and examples.

BRIEF DESCRIPTION OF THE DRAWINGS

FIG. 4A gives structures of IDT, NPDI and IDT-NPDI4. FIG. 4B shows the absorption profiles.

FIG. 5A shows the solution cyclic voltammogram of IDT-NPDI4. FIG. 5B shows the solution cyclic voltammogram of IDT-NPDI4 (solid black traces) with those of the components IDT (dotted trace 1) and NPDI (dotted trace 2).

FIG. 6A shows current-voltage curves and FIG. 6B shows external quantum efficiency of 1:1 blends processed with varying volume percentage of CN solvent additive. FIGS. 6C and 6D are AFM height and AFM phase images, respectively, of the 1:1 blended PTB7-Th: IDT-NPDI4 active layer processed from 10 mg/mL chlorobenzene solution with 5% v/v CN added. Images are 2 µm×2 µm with the surface having an RMS roughness of 1.36 nm.

DETAILED DESCRIPTION

Figure 1:
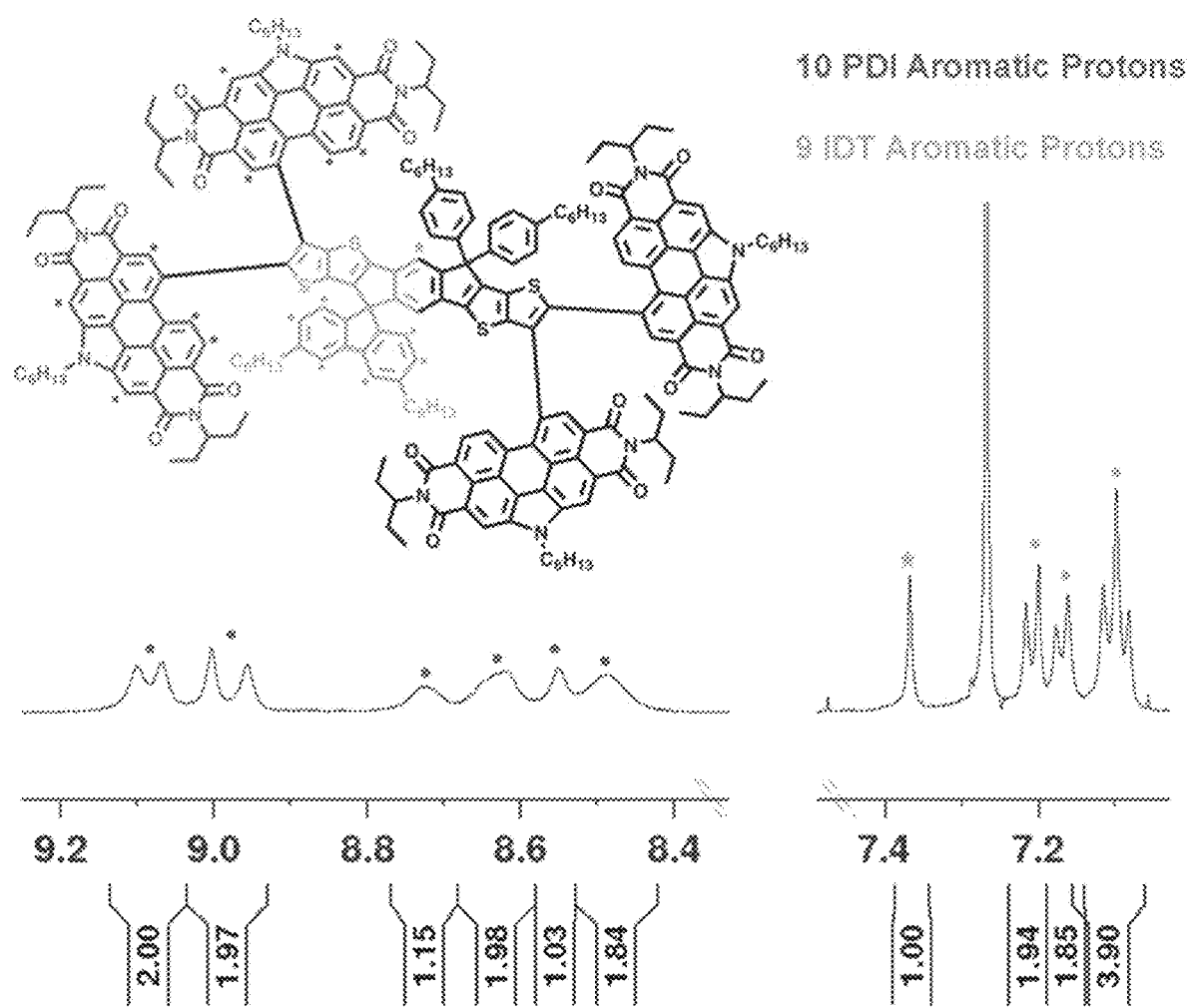
FIG. 1 illustrates the proton NMR spectrum of the aromatic region of IDT-NPDI4.

This invention relates to certain oligomeric PDI compounds in which four or more PDI units are bonded to a selected organic core, particularly a core containing a thiophene ring and preferably containing two or more thiophene rings. In an exemplary embodiment the oligomeric PDI compounds of the invention have structure:

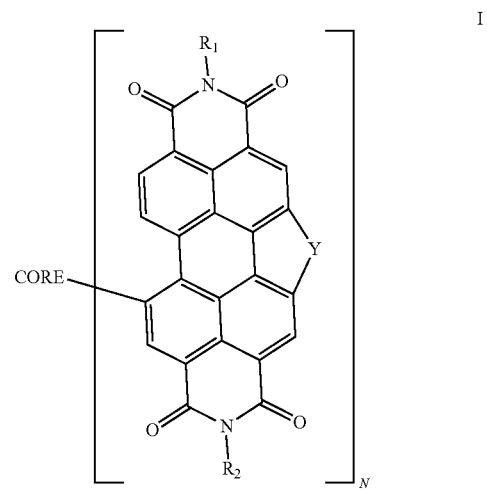

I where N is the integer number of PDI moieties in the oligomeric compound and more specifically N is 4 or more and more specifically N is 4-10 and CORE is an organic core carrying N C—H bonds that are active for DHA, such as those in thiophene rings. In specific embodiments, N is 4, 6, 8 or 10. In specific embodiments, N is 4. In other embodiments, N is 6.

In specific embodiments, the PDI units are those of formula X:

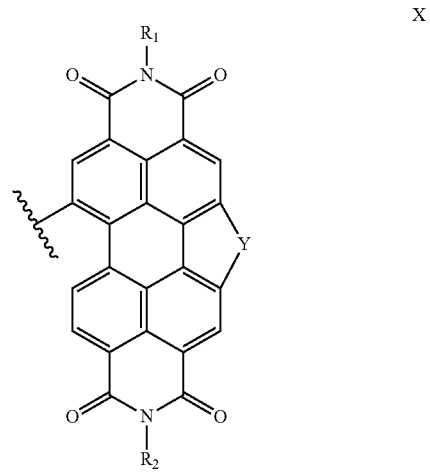

X where:

$Y$ is S, Se or N—$R_3$, $R_1$ and $R_2$ are the same or different and are each independently selected from alkyl groups having 1-30 carbon atoms, and $R_3$ is the same or different from $R_1$ and $R_2$ and is selected from alkyl groups having 1-30 carbon atoms.

In embodiments, the PDI precursor is a compound of formula XI:

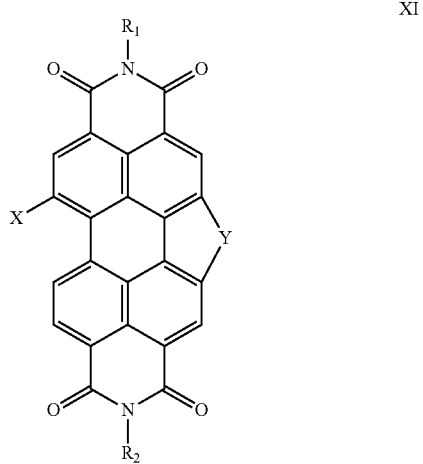

XI where X is halogen (F, Cl, Br or I), triflyl, tosyl, or mesyl and other variables are as in formula X. In a specific embodiment, X is a halogen and in a more specific embodiment, X is Br.

In specific embodiments of formulas X and XI, $R_1$ and $R_2$ are independently selected from a straight-chain alkyl having 10 or more carbon atoms or a branched chain alkyl having 3 to 20 carbon atoms. In specific embodiments, $R_1$ and $R_2$ are independently selected from a straight-chain alky having 3 to 9 carbon atoms. In specific embodiments, $R_1$ and $R_2$ are independently selected from a branched-chain alky having 3 to 10 carbon atoms. In specific embodiments, $R_1$ and $R_2$ are the same group. In specific embodiments, $R_1$ and $R_2$ are selected from branched alkyl groups of formula —C(Ra)(Rb), where Ra and Rb are, independently, alkyl groups having 2-10 carbon atoms. In specific embodiments, Ra and Rb are the same alkyl group. In specific embodiments, Ra and Rb are different alkyl groups. In specific embodiments, Ra and Rb are straight-chain alkyl groups. In specific embodiments, Ra and Rb are branched alkyl groups. In specific embodiments, $R_1$ and $R_2$ are independently 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl. In specific embodiments, $R_1$ and $R_2$ are the same alkyl group. In specific embodiments, $R_1$ and $R_2$ are different alkyl groups. In specific embodiments, $R_1$ and $R_2$ are both 1-ethylpropyl groups. In specific embodiments, $R_1$ and $R_2$ are independently selected from branched alkyl groups having 3-8 carbon atoms. In specific embodiments, $R_1$ and $R_2$ are the same branched alkyl groups.

In specific embodiments of formulas X and XI, Y is N—$R_3$.

In specific embodiments of formulas X and XI, Y is S.

In specific embodiments of formulas X and XI, Y is Se.

In specific embodiments of formulas X and XI, $R_3$ is independently selected from a straight chain alkyl having 1 to 12, or 1-10 or 4 to 12 or 4 to 10 or 4 to 6 carbon atoms or a branched chain alkyl having 3-12 or 3-10 carbon atoms. In specific embodiments, $R_3$ is independently a straight-chain alkyl group selected from a methyl, ethyl, propyl, butyl, pentyl, hexyl, heptyl, octyl, nonyl, and decyl group. In specific embodiments, $R_3$ is independently a branched alkyl group having 3-12 carbon atoms. In specific embodiments, $R_3$ is independently a branched alkyl group having 6-12 carbon atoms. In specific embodiments, $R_3$ is independently a branched alkyl group having 3-6 carbon atoms. In specific embodiments, $R_3$ is independently selected from 1-ethylpropyl, 1-propyl butyl, and 2-ethylhexyl.

In specific embodiments, the CORE of the oligomer is an organic moiety which carries 4 or more C—H bonds that are active for direct arylation or direct heteroarylation. For example, C—H bonds of thiophene rings are active for direct arylation or direct heteroarylation. A thiophene ring has the general structure:

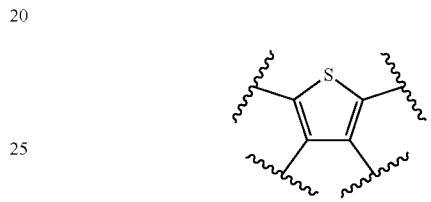

where the ring may carry substituents or be bonded to or fused to one or more aryl, heteroaryl or non-aromatic carbocyclic or heterocyclic rings.

Thus, in an embodiment, the CORE comprises two or more thiophene rings. A thiophene ring of the core may be directly or indirectly linked to or may be directly or indirectly fused to one or more thiophene ring, one or more aryl or heteroaryl rings (other than a thiophene ring) or to one or more non-aromatic carbocyclic or heterocyclic rings.

In embodiments, the core structure contains at least two thiophene rings, wherein (1) the two or more thiophene rings are separated by a linker group M;

(2) the two or more thiophene rings are directly fused to each other or indirectly fused to each other through an optionally substituted aromatic or non-aromatic carbocylic or an optionally substituted aromatic or non-aromatic heterocyclic ring system; or (3) each of two or more thiophene rings is fused to an aromatic or non-aromatic carbocyclic or an aromatic or non-aromatic heterocyclic ring system and the resulting fused rings containing a thiophene ring are each separated by a linker group M.

The linker M can be a single bond, a double bond, or a divalent or trivalent linker comprising an alkylene (—(CH$_2$)$_x$, where x is 1-12, preferably 1-6, more preferably 1-4), an alkenylene (e.g., —CH═CH—), a dialkenylene (e.g., —CH═CH—CH═CH—), an alkynylene (e.g., —C≡C—), a dialkynylene (—C≡C—C≡C—), or an optionally substituted aromatic or non-aromatic carbocyclic or heterocyclic ring system. In specific embodiments, the linker is linear. In specific embodiments, the linker is branched. In specific embodiments, the linker is an alkylene, a dialkenylene, an alkynylene, a dialkynylene or an optionally substituted aromatic or non-aromatic carbocyclic or heterocyclic ring system. In specific embodiments the linker is —CH═CH—, —CH═CH—CH═CH—, —C≡C—, a dialkynylene (—C≡C—C≡C—), or an optionally-substituted aromatic or non-aromatic carbocyclic or heterocyclic ring system. In specific embodiments, M is an optionally-substituted arylene or a heteroarylene. In specific embodiments, M is a moiety as illustrated in Scheme 2.

In specific embodiments, optional substitution of aromatic or non-aromatic carbocyclic or heterocyclic ring systems, arylene or heteroarylene is substitution with one or more halogen, CN, alkyl or alkoxy having 1-30 carbon atoms, 1-12 carbon atoms, 3-12 carbon atoms, 6-12 carbon atoms or 1-3 carbon atoms. In specific embodiments, optional substitution of aromatic or non-aromatic carbocyclic or heterocyclic ring systems is substitution with one or more halogens, or one or more alkyl groups In specific embodiments, the oligomeric compounds have four or more PDI groups therein, each of which is bonded to a core structure containing at least two thiophene rings, wherein:
(1) the two or more thiophene rings are separated by a linker group M;
(2) two or more thiophene rings are directly fused to each other or indirectly fused to each other through an optionally substituted aromatic or non-aromatic carbocylic or an optionally substituted aromatic or non-aromatic heterocyclic ring system; or
(3) each of two or more thiophene rings is fused to an aromatic or non-aromatic carbocyclic or an aromatic or non-aromatic heterocyclic ring system and the resulting fused rings containing a thiophene ring are each separated by a linker group M.

The linker M can be a single bond, a double bond, or a divalent or trivalent linker comprising an alkylene (—(CH$_2$)$_x$—), an alkenylene (e.g., —CH=CH—), a dialkenylene (e.g., —CH=CH—CH=CH—), an alkynylene (e.g., —C≡C—), a dialkynylene (—C≡C—C≡C—), or an optionally substituted aromatic or non-aromatic carbocyclic or heterocyclic ring system. In specific embodiments, M is an arylene or a heteroarylene.

In specific embodiments, M is a moiety as illustrated in Scheme 2 (L1-L15), where:
each R$_6$ is independently selected from hydrogen, halogen, CN, an optionally substituted phenyl or benzyl or an alkyl or alkoxy having 1-30, 1-12, 3-12, 6-12 or 1-3 carbon atoms;
each R$_7$ is independently selected from hydrogen, halogen, CN, an optionally substituted phenyl or benzyl or an alkyl or alkoxy having 1-30, 1-12, 3-12, 6-12 or 1-3 carbon atoms;
each R$_8$ is independently selected from hydrogen, an optionally substituted phenyl or benzyl or an alkyl having 1-30, 1-12, 3-12, 6-12 or 1-3 carbon atoms; and
R$_N$ is selected from hydrogen, an alkyl group having 1-30, 1-12, 3-12, 6-12 or 1-3 carbon atoms, an aryl group and an arylalkyl group. For M of Scheme 2, aryl groups include phenyl and naphthyl groups, among others, and arylalkyl groups include benzyl and phenethyl groups.

More specifically, M is:
(a) L1 or L2;
(b) L3 or L4;
(c) L5 or L6;
(d) L7;
(e) L8;
(f) L9 or L10;
(g) L, L12 or L15;
(h) L13; or
(i) L14

In specific embodiments, the CORE is a moiety C1-C40 as illustrated in Scheme 3, where:
each R$_4$ is independently selected from H, an alkyl or alkoxy group having 1-30 carbon atoms, an optionally substituted aryl or heteroaryl group, where optional substitution is substitution with one or more halogen, CN, alkyl or alkoxy having 1-30 carbon atoms, 1-12 carbon atoms, 3-12 carbon atoms, 6-12 carbon atoms or 1-3 carbon atoms;
each R$_5$ is independently selected from hydrogen, halogen, CN, or alkyl or alkoxy having 1-30, 1-12, 3-12, 6-12 or 1-3 carbon atoms;
each R$_6$ is independently selected from hydrogen, halogen, CN, an optionally substituted phenyl or benzyl or an alkyl or alkoxy having 1-30, 1-12, 3-12, 6-12 or 1-3 carbon atoms;
each R$_7$ is independently selected from hydrogen, halogen, CN, an optionally substituted phenyl or benzyl or an alkyl or alkoxy having 1-30, 1-12, 3-12, 6-12 or 1-3 carbon atoms; and
R$_N$ is selected from hydrogen, an alkyl group having 1-30, 1-12, 3-12, 6-12 or 1-3 carbon atoms, an aryl group or an arylalkyl group.

For CORES of Scheme 3, aryl groups include phenyl and naphthyl groups, among others, and arylalkyl groups include benzyl and phenethyl groups.

In specific embodiments of CORES of Scheme 3, each R$_6$ is hydrogen. In specific embodiments of CORES of Scheme 3, each R$_6$ is an alkyl group having 1-6 carbon atoms. In specific embodiments of CORES of Scheme 3, each R$_7$ is hydrogen, or a halogen and more specifically, each R$_7$ is hydrogen or fluorine and in a further embodiment, one R$_7$ is hydrogen and the other R$_7$ is fluorine. In specific embodiments of the CORES of Scheme 3, each R$_8$ is hydrogen. In specific embodiments, each R$_8$ is an alkyl group having 1-6 carbon atoms. In specific embodiments of CORES of Scheme 3, each R$_7$ is independently hydrogen or halogen or yet more specifically, each R$_7$ is independently hydrogen or fluorine. In specific embodiments, each R$_N$ is hydrogen or an alkyl group having 1-12 carbon atoms or an alkyl group having 1-3 carbon atoms.

More specifically, the CORE is:
a) the moiety C1, C2, C6 or C7;
b) the moiety C3, C4 or C5;
c) the moiety C8, C9 or C35;
d) the moiety C10 or C11;
e) the moiety C12;
f) the moiety C13;
g) the moiety C14, C15 or C16;
h) the moiety C17 or C18;
i) the moiety C19a (Y is C), C19b (Y is P), C19c (Y is N), C19d (Y is S), C19e (Y is Si), or C19f(Y is Ge);
j) the moiety C19a, C19c or C19d);
k) the moiety C20a, C20b or C20c;
l) the moiety C21, C23 or C24;
m) the moiety C22 or C25;
n) the moiety C26 or C27;
o) the moiety C28 or C29;
p) the moiety C30, C31, C32, or C33;
q) the moiety C34 or C36;
r) the moiety C37;
s) the moiety C38;
t) the moiety C39; or
u) the moiety C40.

In a specific embodiment, the core precursor has structure:

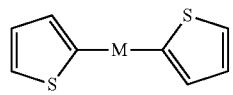

XX1 and the oligomer is:

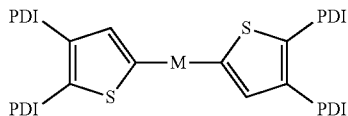

where -M- is a single bond, an alkylene (—(CH$_2$)$_x$—), an alkenylene (e.g., —CH=CH—), a dialkenylene (e.g., —CH=CH—CH=CH—), an alkynylene (e.g., —C≡C—), a dialkynylene (—C≡C—C≡C—), or an optionally substituted aromatic or non-aromatic carbocyclic or heterocyclic ring system. In specific embodiments, M is an arylene or a heteroarylene. In specific embodiments, M is a moiety as illustrated in Scheme 2. In an embodiment, M itself does not contain a thiophene ring with one or more active C—H groups. M may however contain a thiophene ring with no active C—H bonds.

In a specific embodiment, the core precursor has structure:

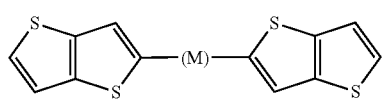

XXII and the oligomer is:

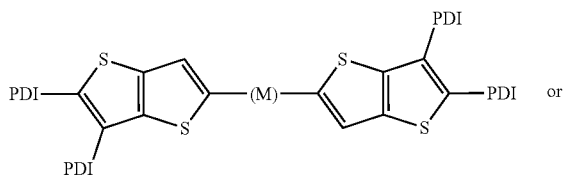

XXXIIA or

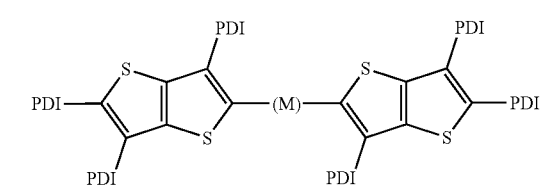

XXXIIB where -M- is a single bond, an alkylene (—(CH$_2$)$_x$—), an alkenylene (e.g., —CH=CH—), a dialkenylene (e.g., —CH=CH—CH=CH—), an alkynylene (e.g., —C≡C—), a dialkynylene (—C≡C—C≡C—), or an optionally substituted aromatic or non-aromatic carbocyclic or heterocyclic ring system. In specific embodiments, M is an arylene or a heteroarylene. In specific embodiments, M is a moiety as illustrated in Scheme 2. In an embodiment, M itself does not contain a thiophene ring with one or more active C—H groups. M may however contain a thiophene ring with no active C—H bonds.

In a specific embodiment, the core precursor has structure:

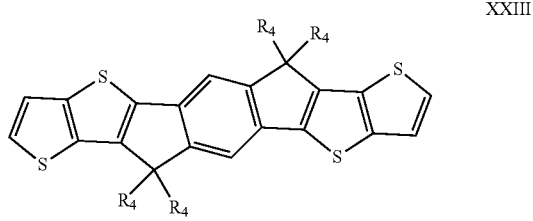

XXIII and the oligomer has structure:

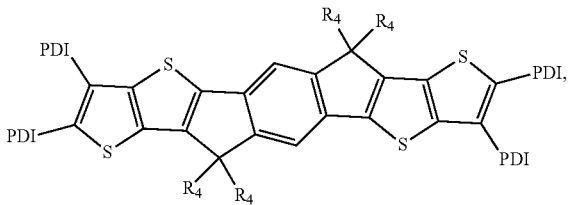

where R$_4$ is as defined above. In specific embodiments, each R$_4$ is alkyl. In specific embodiments, each R$_4$ is alkoxy. In specific embodiments, each R$_4$ is optionally substituted aryl. In specific embodiments, each R$_4$ is optionally substituted phenyl. Optional substitution is substitution of a phenyl with 1-4 non-hydrogen substituents selected from halogen, alkyl or alkoxy having 1-12 carbon atoms, or CN.

In a specific embodiment, the core precursor has structure:

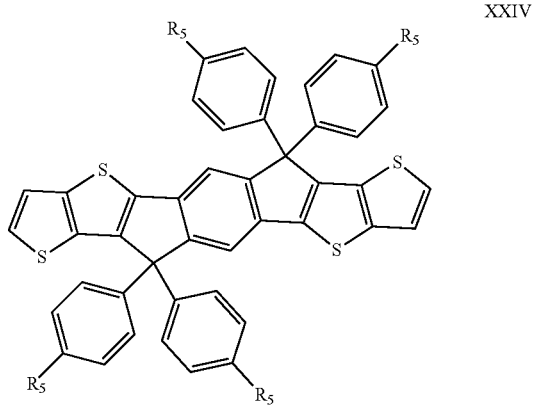

XXIV and the oligomer has structure:

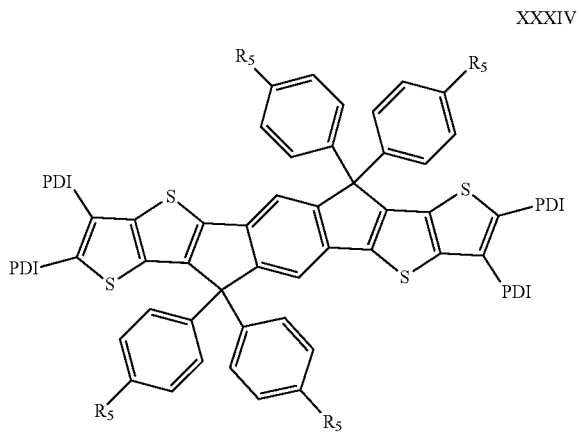

XXXIV where each $R_5$ is as defined above and in specific embodiments each $R_5$ is an alkyl group. In an embodiment all $R_5$ are the same group. In an embodiment, each $R_5$ is a straight-chain alkyl of 3-12 or 3-8 carbon atoms. In a specific embodiment each $R_5$ is —$C_6H_{13}$. In other embodiments, each $R_5$ is a branched alkyl group. In specific embodiments, each $R_5$ is selected from branched alkyl groups of formula —C(Ra)(Rb), where Ra and Rb are, independently, alkyl groups having 2-10 carbon atoms. In specific embodiments, Ra and Rb are the same alkyl group. In specific embodiments, Ra and Rb are different alkyl groups. In specific embodiments, Ra and Rb are straight-chain alkyl groups. In specific embodiments, each $R_5$ is independently a 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl.

In an embodiment, the oligomer of the invention has CORE of structure:

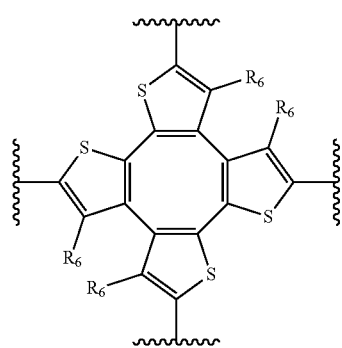

LV where $R_6$ is independently selected from hydrogen, halogen, CN, an optionally substituted phenyl or benzyl or an alkyl or alkoxy having 1-30 carbon atoms. In more specific embodiments, $R_6$ is hydrogen or an alkyl group having 1-12 carbon atoms. In more specific embodiments, $R_6$ is hydrogen or an alkyl group having 1-6 carbon atoms. In more specific embodiments. In more specific embodiments of compounds of core LV, in PDI, Y is NR3. In more specific embodiments of compounds of core LV, in PDI, Y is S or Se. In more specific embodiments of compounds of compounds of core LV, in PDI, $R_1$ and $R_2$ are alkyl groups having 6-12 carbon atoms.

In specific embodiments, tetramers of the disclosure include:

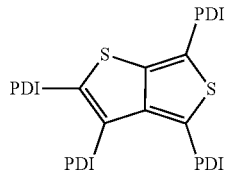

IVA

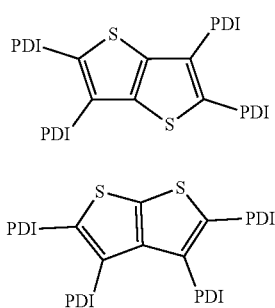

IVB

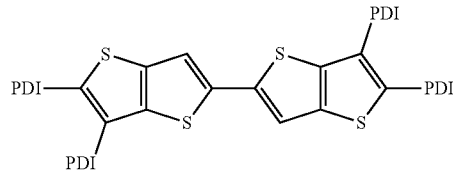

IVC

IVD

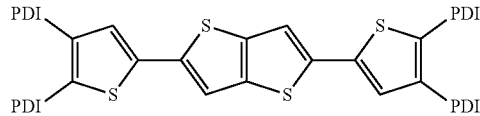

IVE

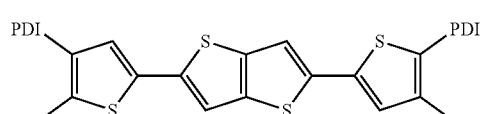

IVF or

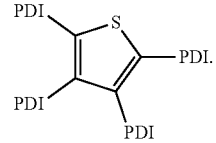

IVG

In specific embodiments of IVA-IVG, in PDI groups, Y is N—$R_3$.

In specific embodiments, hexamers of the disclosure include:

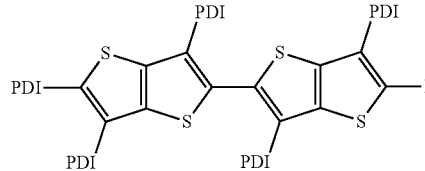

VIA, or

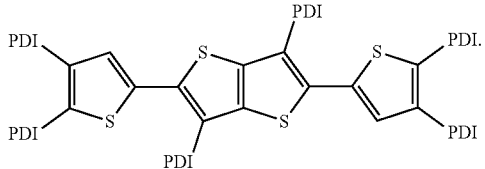

VIB

In specific embodiments of VIA or VIB, in PDI groups, Y is N—$R_3$.

In specific embodiments, hexamers of the disclosure include:

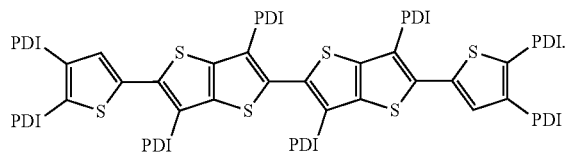

VIIIA

In specific embodiments of VIIIA in PDI groups, Y is N—R$_3$.

In specific embodiments, the cores of tetramers herein include:

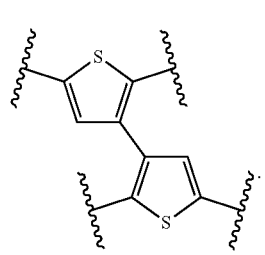

(3, 3'-bithiophene)

In specific embodiments, the cores of tetramers herein include:

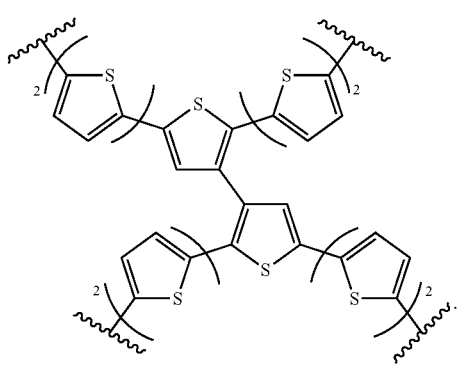

In specific embodiments, the cores of tetramers herein include:

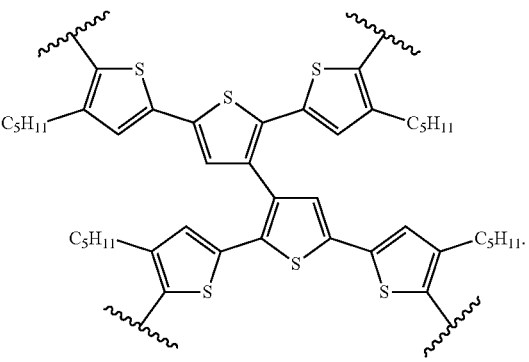

In specific embodiments, the cores of tetramers herein include:

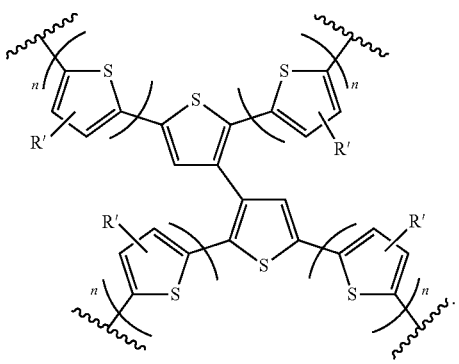

where n is 0, 1 or 2, R' is H or an alkyl having 1-15 carbon atoms.

In specific embodiments, the cores of tetramers herein are other than 3, 3'-bithiophene.

In specific embodiments, the cores of tetramers herein are other than:

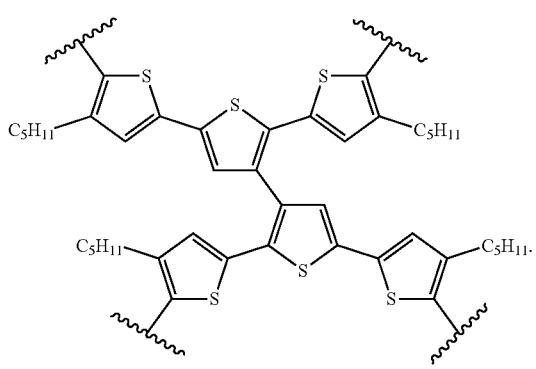

In specific embodiments, the cores of tetramers herein are other than:

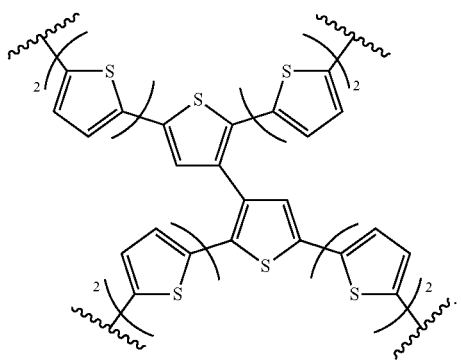

In specific embodiments, the cores of tetramers herein are other than:

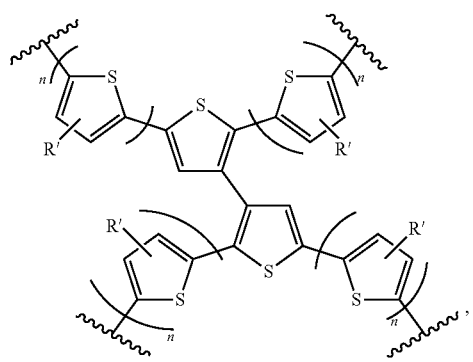

where n is 0, 1 or 2, R' is H or an alkyl having 1-15 carbon atoms.

In specific embodiments, the cores of tetramers herein are other than

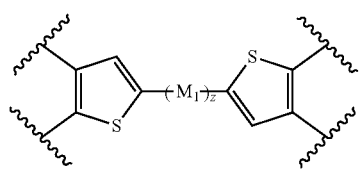

where:

z is 0 or 1 and M1 is an arylene, a heteroarylene, or an organic dye molecule.

In an aspect, the invention relates to a method of making the oligomeric PDI compound herein which comprises reacting a core precursor carrying 4 or more C—H bonds that are active for direct arylation or direct heteroarylation with 2 or more equivalents with respect to the amount of core precursor of the PDI precursor of formula XI, wherein X is a good leaving group, such as Br.

Scheme 1A illustrates a generic reaction of the disclosure in which N (which is 4 or more) PDI units are bonded to a multivalent core having N (4 or more) C—H bonds which are active for DHA coupling with a Pd catalyst.

Scheme 1B illustrates a more specific reaction of the in which 4 PDI units are bonded to a tetrameric core (containing 4 active C—H bonds which are indicated by "*") to form a tetramer. The reaction is conducted in an appropriate solvent above room temperature and is illustrated to employ at least the stoichiometric amount of the PDI precursor to form the tetramer. Specific reagents, solvents and reaction conditions are illustrated herein and in the Examples.

SCHEME 1A

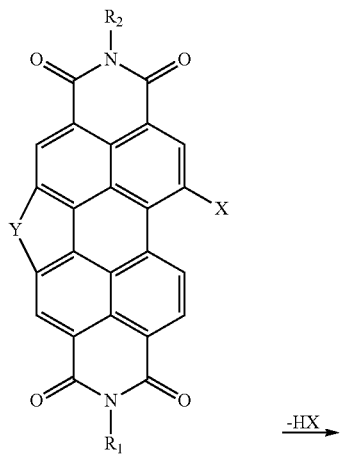

N eq.    -HX→

CORE (Carrying N active C—H bonds)

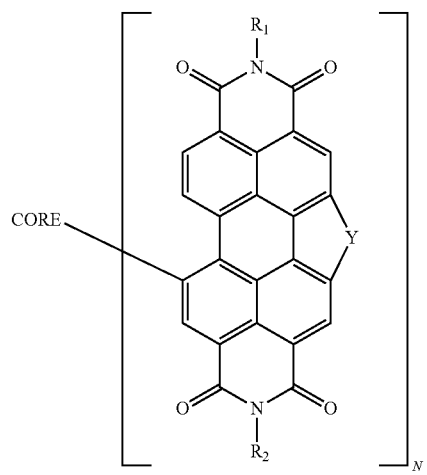

SCHEME 1B

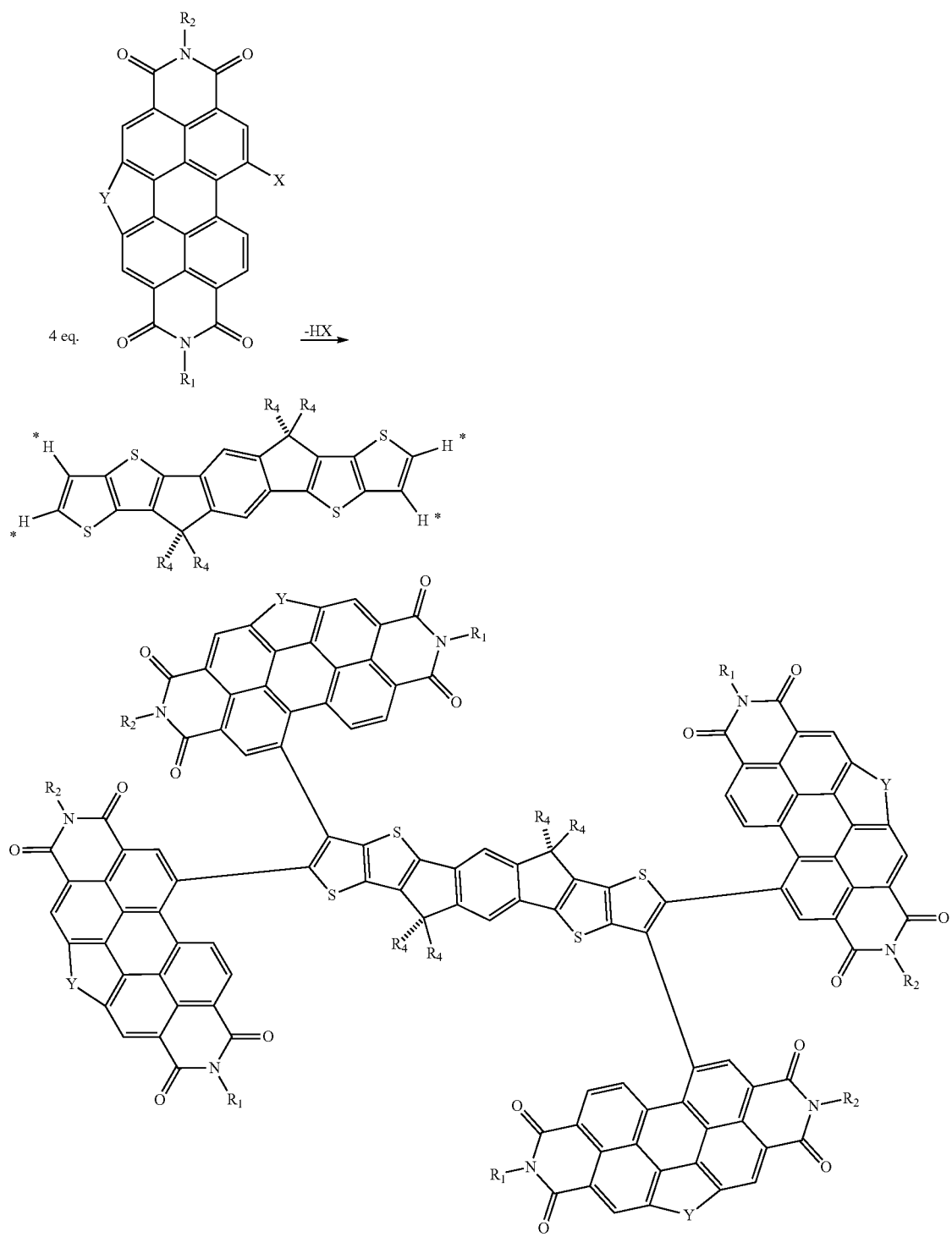

More specifically, if the oligomer is a tetramer, it is preferred to employ 4 or more equivalents of the PDI precursor. More specifically, if the oligomer is a hexamer, it is preferred to employ 6 or more equivalents of the PDI precursor. More specifically, if the oligomer is an octamer, it is preferred to employ 8 or more equivalents of the PDI precursor. More specifically, if the oligomer is a decamer, it is preferred to employ 10 or more equivalents of the PDI precursor. Generally, it is preferred to employ from 1-10% in excess of the stoichiometric amount of the PDI precursor needed to form the desired oligomeric PDI compound.

The reaction is generally conducted in a solvent in which the PDI precursor and the core precursor are at least partially soluble. Useful solvents include dimethylacetamide (DMA), dimethylformamide (DMF), tolulene, xylene(s), tetrahydrofuran. One of ordinary skill in the art can select an appropriate solvent for a given set of reactants in view of what isexemplified herein and in view of what is known in the art.

The reaction is typically conducted at temperatures above ambient room temperature. More specifically the reaction is conducted at a temperature greater than 50° C. and more preferably at a temperature greater than 70° C. and yet more preferably at a temperature greater than 100° C. The upper temperature limit of the reaction at ambient room pressure is generally about the boiling point of the selected solvent and the reaction is conducted under reflux. In a specific embodiment, the reaction is carried out in a sealed vessel at about ambient room pressure at temperatures greater than 50 OC and more preferably at a temperature greater than 70 OC and yet more preferably at a temperature greater than 100° C. In a specific embodiment, the reaction is carried out in a sealed vessel at a temperature ranging from 70° C. to 130° C., or more preferably at a temperature ranging from 80° C. to 130° C., or more preferably at a temperature ranging from 100° C. to 130° C. As illustrated in the examples herein, increasing reaction temperature of the sealed reaction vessel can result in yield improvements. One of ordinary skill in the art can select appropriate reaction temperature for a given solvent and a given set of reactants in view of what is exemplified herein and in view of what is known in the art.

The reaction is conducted in the presence of a DHA catalyst, such as a palladium catalyst. Exemplary Pd catalysts are $Pd(PPh_3)_4$ or $Pd(OAc)_2$. In a specific embodiment, the Pd catalyst is a catalyst with a diphenylphosphine ligand and that catalyst may be attached to a silica support. In an embodiment, the catalyst is a heterogeneous Pd catalyst of formula:

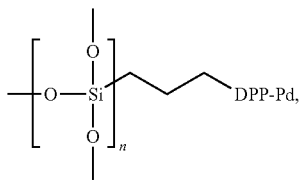

such as the commercially available heterogeneous Pd catalyst SiliaCat® DPP-Pd (see web site silicycle.com). One of ordinary skill in the art can select an appropriate catalyst for the desired DHA reaction and the selected reactants, solvent and reaction conditions in view of what is exemplified herein and in view of what is known in the art.

It is preferred to prepare a given oligomeric compound substantially free of other oligomers. For example a tetramer is preferably prepared substantially free of corresponding dimers, trimers and higher oligomers. Substantially free of other oligomers means that the desired oligomer contains less than 1% by weight of other oligomers. Preferably the desired oligomer is prepared with less than 0.5% by weight of other oligomers. The oligomer prepared is generally controlled by controlling the stoichiometry of the added reactants and the reaction conditions, as illustrated in the examples herein. Undesired oligomers, if present, can be removed by selected washing with solvent as illustrated in the examples herein. However, alternatively or in combination, crude product or washed product can be purified by silica gel column chromatography employing an appropriate solvent gradient, e.g., a hexane to dichoromethane gradient.

It will be appreciated that purification steps, such as elution time, can vary dependent upon the given oligomer, and reactants employed.

One of ordinary skill in the art will recognize that starting materials and reagents other than those specifically disclosed in the Examples can be employed in the reactions herein without resort to undue experimentation. One of ordinary skill in the art knows how to select appropriate starting materials for alkylation and to if necessary adjust the solvent employed.

SCHEME 2 - EXEMPLARY M LINKERS

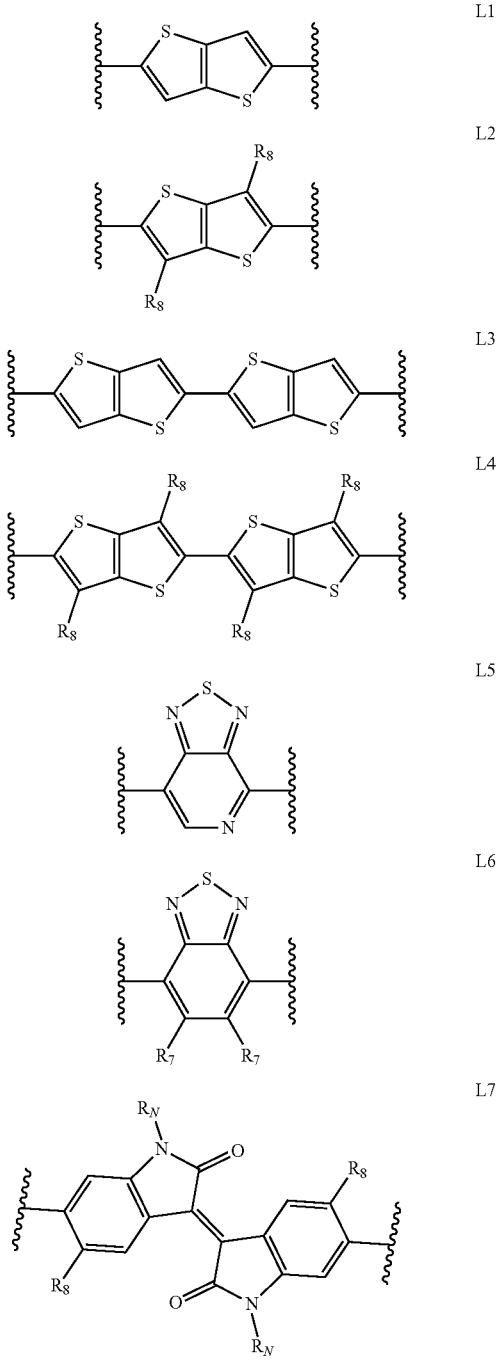

-continued
L8
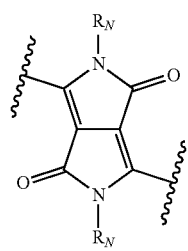
L9
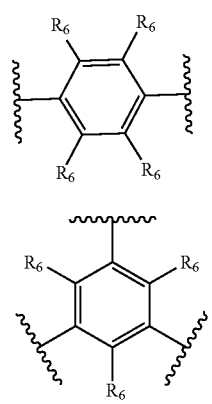
L11
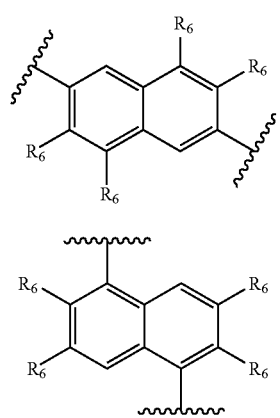
L13
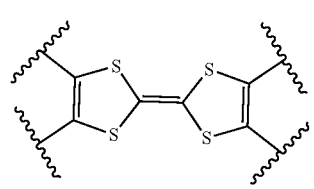
L14
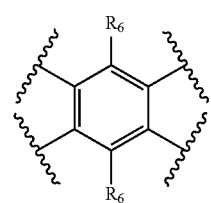
-continued
L15
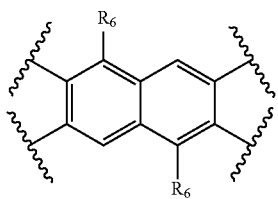
SCHEME 3
C1
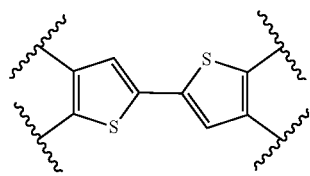
C2
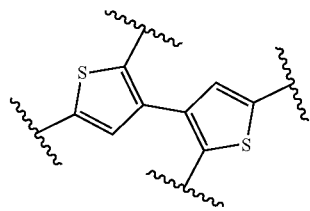
C3
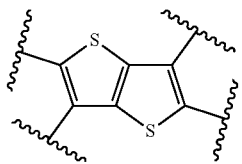
C4
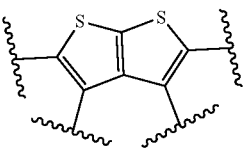
C5
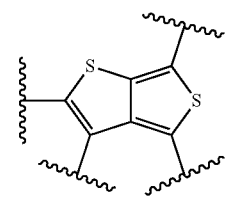
C6
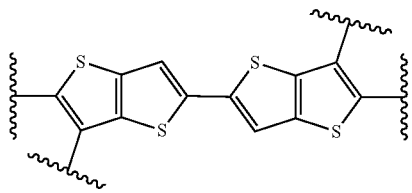

-continued
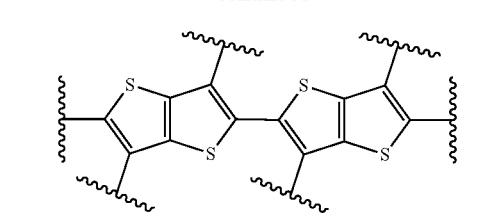
C7
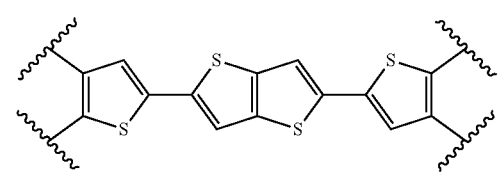
C8
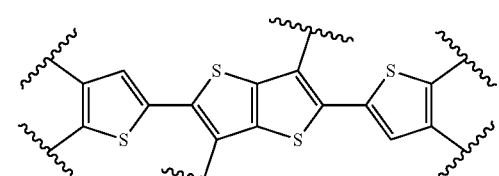
C9
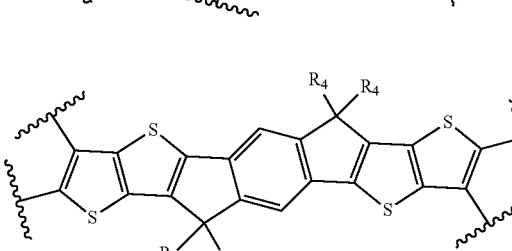
C10
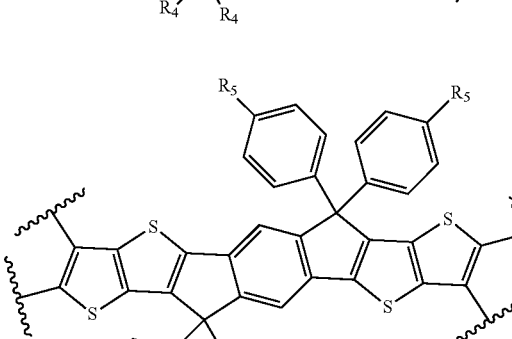
C11
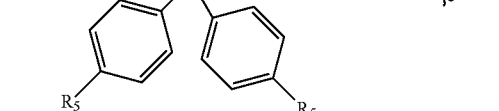
C12
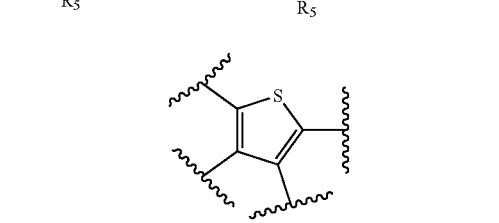
C13
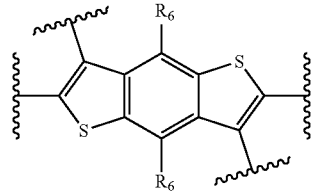
C14
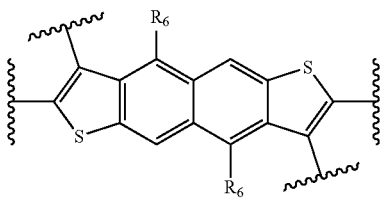
C15
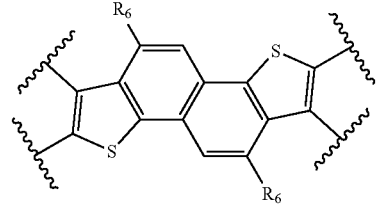
C16
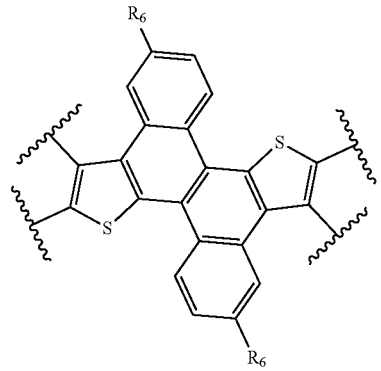
C17
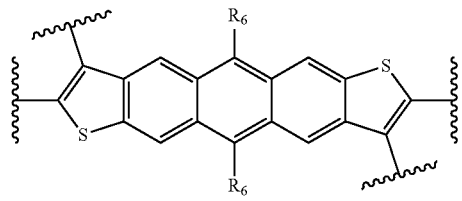
C18
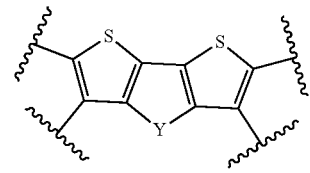
C19a-C19f
Y = C, P, N, S, Si, Ge -continued
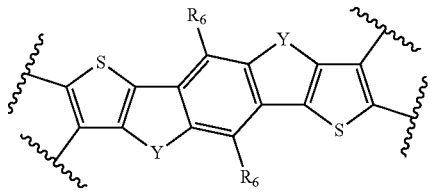
each Y = S or N
C20a (both Y = S)
C20b (both Y = N)
C20c (one Y = S, other Y = N)
C21
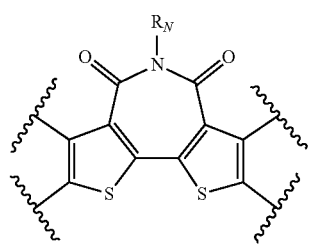
C22
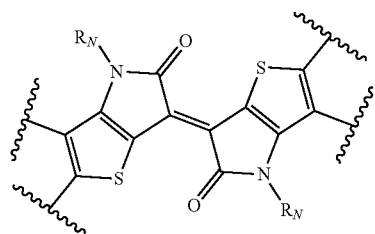
C23
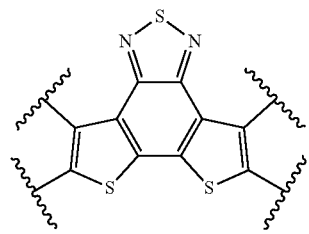
C24
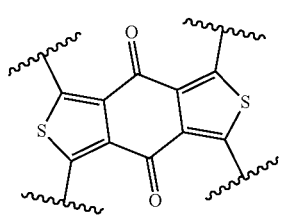
C25
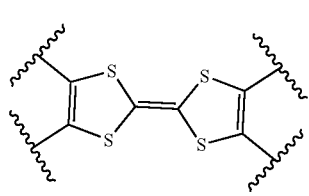
-continued
C26
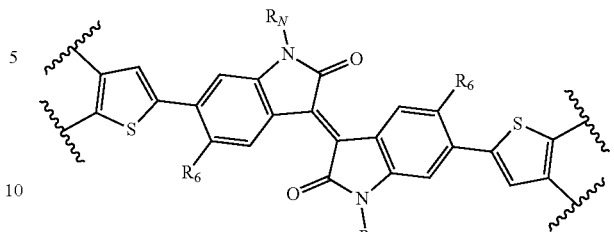
C27
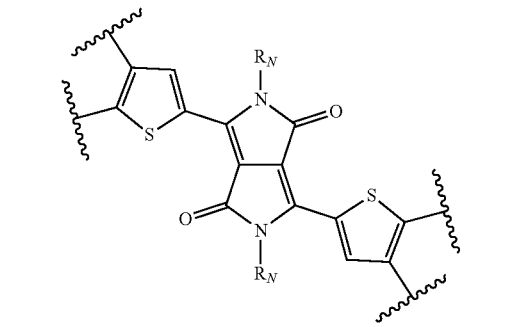
C28
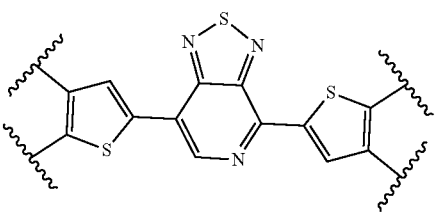
C29
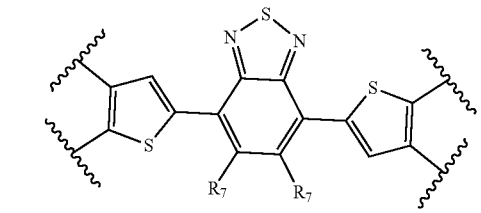
C30
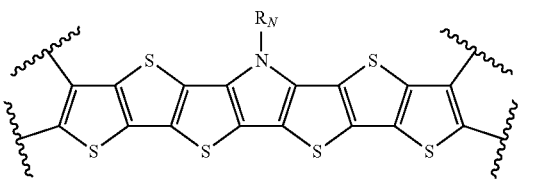
C31
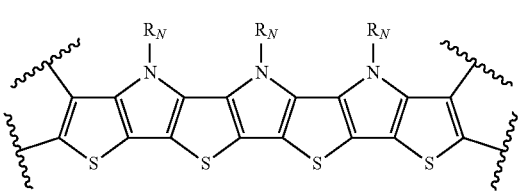

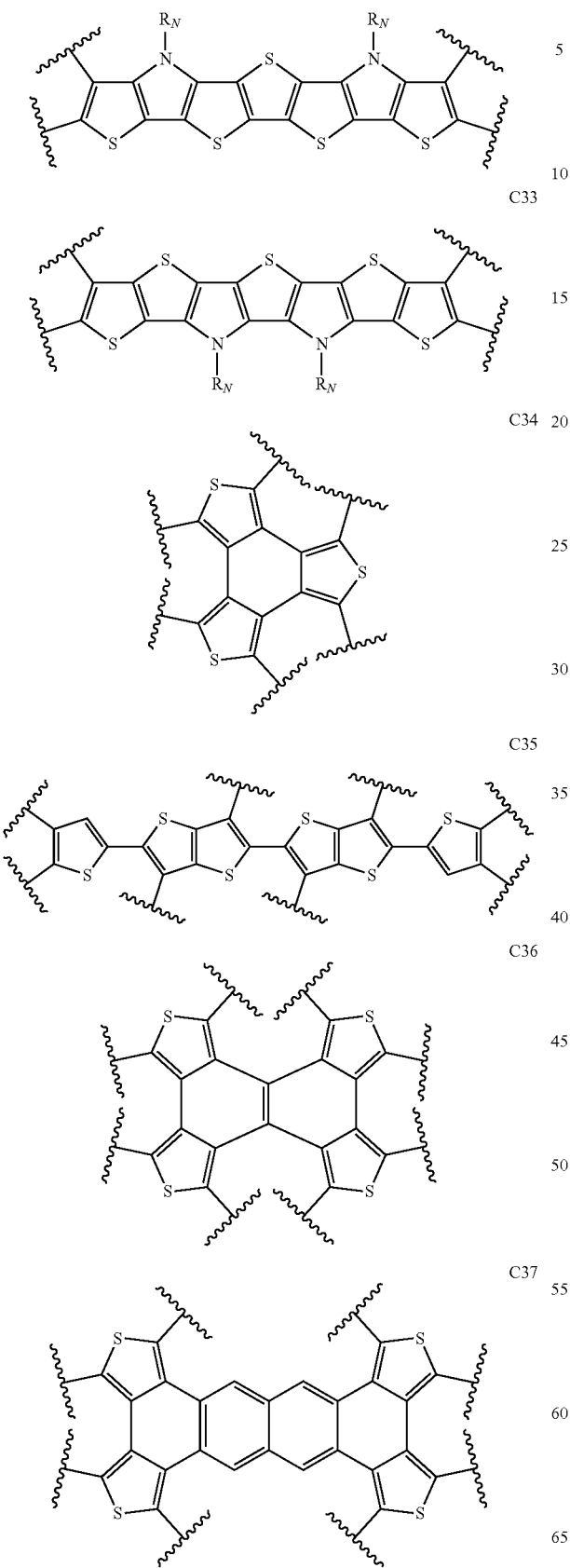
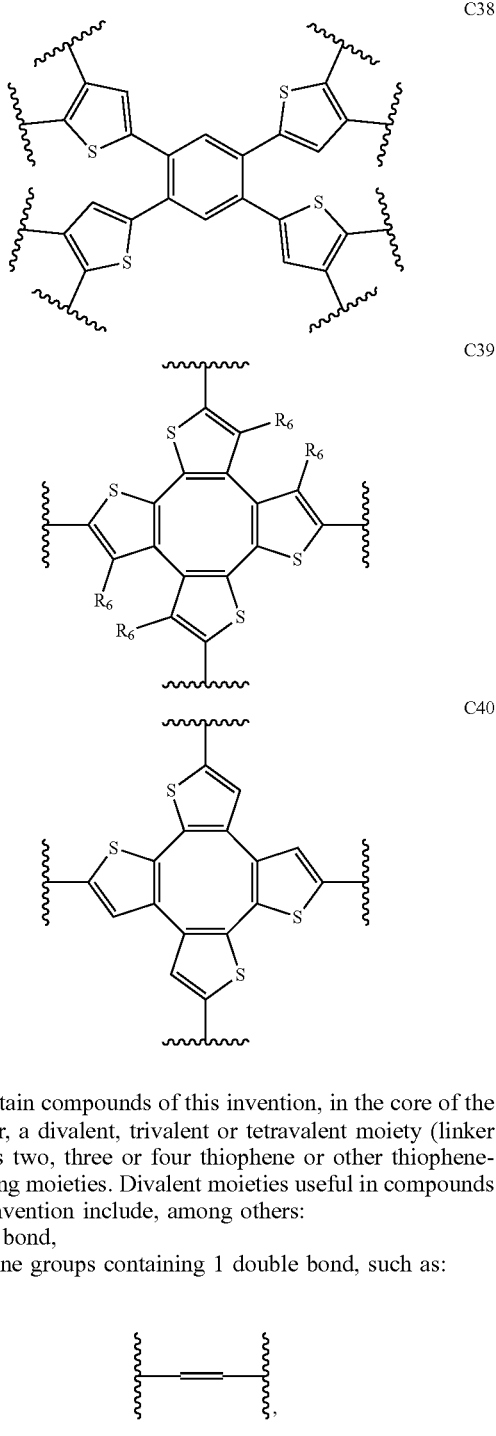

In certain compounds of this invention, in the core of the oligomer, a divalent, trivalent or tetravalent moiety (linker M) links two, three or four thiophene or other thiophene-containing moieties. Divalent moieties useful in compounds of the invention include, among others:
a single bond,
alkenylene groups containing 1 double bond, such as:

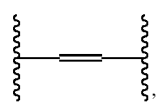

containing one double bond; or
or those containing 2 double bonds (also designated dialkenylene groups), such as

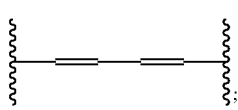

alkynylene groups, containing 1 triple bond, such as:

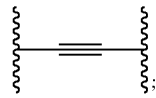

or those containing 2 triple bonds (also designated dialkynylene groups), such as:

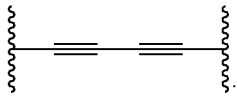

A divalent arylene moiety is derived from an aromatic hydrocarbon formally by removal of two hydrogens. A trivalent arylene moiety is derived from an aromatic hydrocarbon formally by removal of three hydrogens. A tetravalent arylene moiety is derived from an aromatic hydrocarbon formally by removal of four hydrogens arylene groups herein include those derived from an aromatic hydrocarbon have one or more aromatic hydrocarbon rings which include those with fused rings. More specifically, the arylene group can include 1, 2, 3 or 4 aromatic rings. In specific embodiments, arylene groups are optionally substituted with one or more alkyl groups, halogens or CN groups.

Divalent moieties include arylene groups having available two sites of attachment:

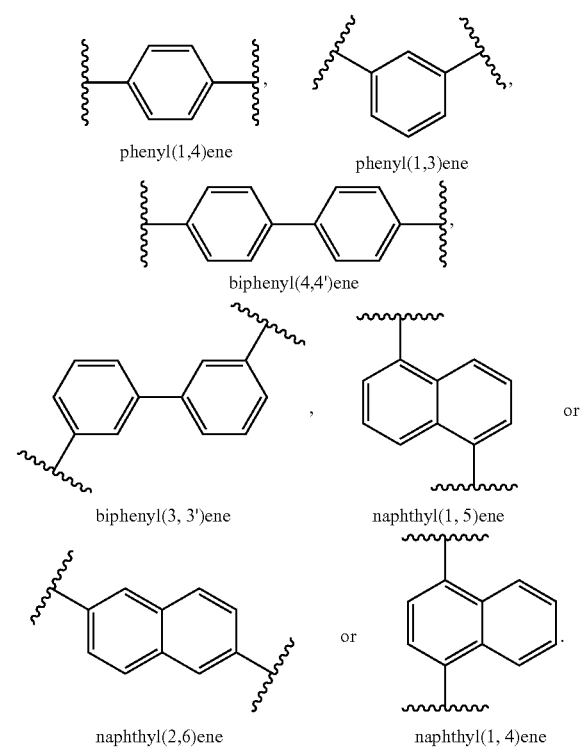

Di-, tri- or tetravalent aromatic linkers include those where the aromatic rings are bonded to each other by one or more single bonds (as in biphenylenes above) and are also exemplified by:

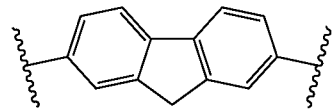
(derived from fluorene)

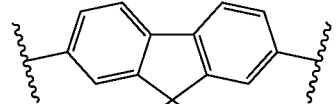
(derived from spirobifluorene

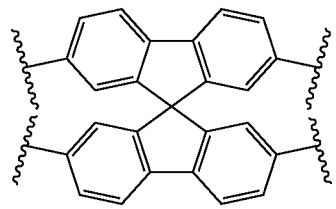
(derived from spirobifluorene)

Each of the exemplified linkers above is optionally substituted with one or more alkyl groups, halogens, nitro groups or CN groups.

Di-, tri- or tetravalent linkers include those that are derived from heteroaromatic compounds. Heteroaromatic compounds include those having one or more aromatic rings that have at least one heteroatom, e.g., N, O or S. In specific embodiments, heteroaromatic compounds have at least one 5- or 6-member heteroaromatic ring. In a specific embodiment, the heteroaromtic linker can be an oligomer having 1-8 repeats of the heteroaromatic ring(s).

Divalent heteroaromtic linkers include:

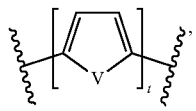

here V is O, S or Se and t is 1, 2, 3, 4, 5, 6, 7 or 8.

Additional exemplary M groups are illustrated in Scheme 2.

It will be appreciated that trivalent and tetravalent moieties or groups illustrated in Scheme 3 can be converted into divalent groups by substitution of one or two hydrogens, alkyl groups (e.g., a $C_{1-12}$, $C_{1-6}$, $C_{6-12}$, $C_{1-3}$, $C_{3-9}$ or $C_{3-6}$ alkyl group) or another non-hydrogen substituent (e.g., a nitro group, a cyano group or a halogen) at one (for trivalent moieties) or two (for tetravalent moieties) of the possible bonding sites on the moiety. Similarly a tetravalent moiety can be converted to a trivalent moiety.

The term alkyl refers to a monovalent group formally derived from a saturated hydrocarbon group by removal of a hydrogen. An alkyl group has the general formula $C_nH_{2n+1}$. Alkyl groups can be straight-chain (linear) or branched. Alkyl groups herein can have 1-30 carbon atoms and more preferably 1-20 carbon atoms. Branched alkyl groups herein can have 3-30 carbon atoms and more preferably 3-20 carbon atoms. Straight-chain alkyl groups include those having 1-3 carbon atoms, 1-6 carbon atoms, 4-8 carbon atoms, 6-12 carbon atoms, and 6-20 carbon atoms, among other groups of carbon atom range. Straight-chain alkyl groups include methyl, ethyl, propyl, hexyl, heptyl, octyl, nonyl, decyl, dodecyl individually or in any combination. Branched alkyl groups include isopropyl, iso-butyl, sec-butyl, 1-ethylpropyl, 1-propylbutyl, 1-butylpentyl, 1-pentylhexyl, lhexylheptyl, 1-heptyloctyl, 1-octylnonyl, 1-nonyldecyl, 2-ethylhexyl individually or in any combination. Branching may occur anywhere along the alkyl chain from the site of attachment of the alkyl group. For example, a branch may occur at the first carbon (as in al-ethylpropyl group). The branching can occur for example at the second carbon along the chain (e.g., 2-ethylhexyl). There may be multiple branches along the chain (e.g., 1-ethyl-5-methylhexyl). In specific embodiments, a branched alkyl chain has one branching point which is at the first, second or third carbon from the site of attachment.

Cycloalkyl is a subset of alkyl groups having a carbon ring of 3 or more atoms, typically 3-12 atoms and more typically 3-10 atoms. In specific embodiments, cycloalkyl groups have 3, 4, 5, 6, 7 or 8 member carbon rings. Herein a cycloalkyl can replace an alkyl group. Specific cycloalkyl groups include cyclopropyl, cyclobutyl, cyclopentyl, cyclohexyl, cycloheptyl, cyclooctyl, cyclononyl and cyclodecyl groups. Cycloalkyl groups are optionally substituted.

An alkoxy group is an alkyl group, as broadly discussed above, linked to oxygen ($R_{alkyl}$—O—).

A divalent alkyl group (e.g., for a straight-chain group —$(CH_2)_p$—, where p is 1-12) is called an alkylene group herein. Such a group is attached between two other moieties by formation of a bond to two carbons in the group. The alkylene group is an exemplary linker herein. Alkylene groups may be straight-chain or branched and are optionally substituted with one or more non-hydrogen substituents. Alkylene groups include those having 2-12, 2-8, 2-6 or 2-4 carbon atoms. Linker groups (L1) herein include alkylene groups, particularly straight chain, unsubstituted alkylene groups, —$(CH_2)n$-, where n is 1-12, n is 1-10, n is 1-9, n is 1-8, n is 1-7, n is 1-6, n is 1-5, n is 1-4, n is 1-3, n is 2-10, n is 2-9, n is 2-8, n is 2-7, n is 2-6, n is 2-5 or n is 2-4. Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are unsubstituted or optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated (perfluorinated) or partially fluorinated aryl groups, such as aryl groups having one or more hydrogens replaced with one or more fluorine atoms.

Arylalkyl groups are those in which an alkyl group is substituted with an aryl group. Arylalkyl groups include benzyl and phenethyl groups among others. Most generally alkyl groups are straight-chain or branched as described herein. In specific embodiments, the alkyl groups of arylalkyl groups have 1-6 carbon atoms and more preferably 1-3 carbon atoms. Arylalkyl groups can contain any aryl group as described herein. Arylalkyl groups are optionally substituted as described herein. Substituted arylalkyl groups include those in which the aryl group is substituted with 1-5 non-hydrogen substituents and particularly those substituted with 1, 2 or 3 non-hydrogen substituents. Useful substituents include among others, methyl, methoxy, hydroxy, halogen, and nitro. Particularly useful substituents are one or more halogens. Specific substituents include F. Cl, and nitro.

A divalent arylene (AR) moiety is derived from an aromatic hydrocarbon formally by removal of two hydrogens. Arylene groups herein include those derived from an aromatic hydrocarbon have one or more aromatic hydrocarbon rings which include those with fused rings. More specifically, the arylene group can include 1, 2, 3 or 4 aromatic rings. In specific embodiments, arylene groups are optionally substituted with one or more alkyl groups, halogens or CN groups. Arylene groups include among others phenylene, biphenylene, and naphthylene.

A heterocyclic (or herterocycyl) group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclic groups include those having 3-12 carbon atoms, and 1-6, heteroatoms, wherein 1 or 2 carbon atoms are replaced with a —CO— group. Heterocyclic groups include those having 3-12 or 3-10 ring atoms of which up to three can be heteroatoms other than carbon. Heterocyclic groups can contain one or more rings each of which is saturated or unsaturated. Heterocyclic groups include bicyclic and tricyclic groups. Preferred heterocyclic groups have 5- or 6-member rings. Heterocyclic groups are optionally substituted as described herein. Specifically, heterocyclic groups may be substituted with one or more alkyl groups. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic group include those having 5- or 6-member rings and two different heteroatom, e.g., N and O, O and S or N and S. Specific heterocyclic groups include among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Rings of the group may be fused. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyrrolyl, pyridinyl, pyrazinyl, pyrimidinyl, quinolinyl, purinyl, thiophenyl, or indolyl groups.

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

The term carbocyclic refers generally to a hydrocarbon having one or more carbon rings, wherein the rings are not aromatic rings. Aryl and heteroaryl groups include those with 5 or 6-member rings. Carbocyclic rings include those with 3-12 member carbon rings. Carbocyclic rings can include bicyclic and tricyclic rings.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

With respect to the various compounds of the disclosure, the atoms therein may have various isotopic forms (e.g., isotopes of hydrogen include deuterium and tritium). All isotopic variants of compounds of the disclosure are included within the disclosure and particularly include deuterium and 13C isotopic variants. It will be appreciated that such isotopic variants may be useful for carrying out various chemical and biological analyses, investigations of reaction mechanisms and the like. Methods for making isotopic variants are known in the art.

Compounds of the disclosure can be prepared by one of ordinary skill in the art in view of the descriptions provided herein and what is known in the art from commercially or otherwise readily available starting materials and reagents. As described herein in the Examples, known synthetic methods can be readily adapted for synthesis of the compounds of the formulas herein.

Compounds of the disclosure may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (e.g., organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the invention may include salts and solvates of compounds of formulas herein. Solvates include solvates of salts. Solvates include, among others, hydrates.

Compounds of the present disclosure, and salts thereof, may exist in their tautomeric form, in which hydrogen atoms are transposed to other parts of the molecules and the chemical bonds between the atoms of the molecules are consequently rearranged. It is understood that all tautomeric forms, insofar as they may exist, are included within the disclosure. Additionally, compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended.

The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form. The term enantiomerically pure refers to a sample containing molecules of a given structure whose molecules have the same chirality sense (i.e., are the same optical isomer) within the limits of detection. The term substantially enantiomerically pure refers to a sample containing molecules of a given structure, wherein equal to or less than 1% of the molecules of the sample have a different chirality sense. Compounds of the invention include those which are enatiomerically pure and those that are substantially enatiomerically pure.

In embodiments, the disclosure provides an electronic device employing an electron acceptor wherein the electron acceptor is one or more compounds of formulas herein.

In embodiments, the disclosure provides an organic solar cell, which comprises one or more compounds of any one of the formulas herein which is an electron acceptor.

In embodiments, the disclosure provides an organic thin film transistor, which comprises one or more compounds of any one of the formulas herein which is an electron acceptor.

In embodiments, the disclosure provides a redox flow battery, which comprises one or more compounds of any one of the formulas herein which is an electron acceptor.

Those of ordinary skill in the art will appreciate that methods for the preparation of organic solar cells, organic thin film transistors and redox flow batteries are known in the art and can be applied employing materials of the formulas herein. In view of what is known in the art and what is described herein one of ordinary skill in the art can employ materials described and characterized herein in such devices without resort to undue experimentation.

Additional details of the synthesis, characterization and application of oligomeric PDI materials are provided in references cited herein and any supporting information of each of these references, which is freely available on-line for the publisher. For example, references[47,48] (Payne et al., 2018; Welsh et al., 2019, respectively) provide additional examples of synthesis of oligomers as described herein and are each incorporated by reference herein in its entirety for synthetic methods, examples methods and example starting materials and oligomers.

Additional details of processing of materials, such as oliogmeric PDI materials of the invention, and the preparation of devices, such as organic solar cells are provided in certain references cited herein and any supporting information of each of these references which is freely available on-line for the publisher. Each of the references cited herein and any corresponding supporting information is incorporated by reference herein in its entirety for such additional details including synthetic methods for starting materials, purification methods, characterization of compounds, processing of oligomeric PDT materials, components of devices employing these materials and methods for such characterization, construction and testing of organic solar cell, as well as structure and components of organic solar cells.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. For compositions as claimed herein, the term consisting essentially of excludes any component that detrimentally and materially affects the properties of that composition for use in an application recited herein, such as use of the composition as an electron acceptor particularly in an electronic device or more specifically in a thin film transistor, a redox flow battery Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

IDT flanked with N-annulated PDI (IDT-NPD12) as shown in Scheme 4 was an initial target of continuing work in view of previous success of N-annulated perylene diimide materials[33] as non-fullerene acceptors and PDI-IDT compounds showing good OPV performance[34-36] Using optimized DHA conditions, IDT was reacted with 2.0 equivalents of the activated PDI starting material NPDI-Br (FIG. 1A). Unexpectedly, the reaction proceeded almost exclusively, albeit in relatively low yield, to the tetra-substituted product, IDT-NPDI4, instead of the expected bis-substituted product.

To probe this unexpected reactivity, the same reaction was performed with 4.2 equivalents of NPDI-Br which was found to result in a mixture of both starting materials, mono-, bis-, tris- and tetra-substituted products, suggesting a stepwise reaction (FIG. 1B). The individual products proved difficult to separate by silica-gel column chromatography, but the fractions isolated were characterized by mass spectroscopy and found to be mono-, bis-, tris-, and tetra-substituted products. The ¹H NMR spectra were convoluted, especially for the bis-substituted product suggesting product mixtures of various substitutions i.e. 2'2, 2'3, 3'3. Typically, these alternate substitutions are unwanted and have been seen as a major drawback of DHA reactions which has resulted in studies addressing this unselective C—H activation and how it can be mitigated. This is particularly seen as a problem in direct heteroarylation polymerization (DHAP) reactions where once formed, such 'defect' structures are covalently incorporated into the polymer backbone and cannot be removed.[9-11] However, it was found that this direct reactivity could be exploited to access new materials, specifically those with tetra and higher PDI-substituted thiophene-based cores. It was determined that increasing the reaction temperature could be employed to drive the reaction to further completion resulting in the tetramer as the main product with only a small amount of tris-substitution. It was also found that the tris-substituted product could be removed by an ethyl acetate wash and the tetrameric product, IDT-NPDI4, was isolated as a fine dark red crystalline powder in 62% yield (FIG. 1C). The IDT-NPDI4 tetramer structure as shown, was confirmed by NMR spectroscopy MALDI-TOF mass spectrometry and elemental analysis.

For example, the aromatic region of the ¹H NMR spectrum of IDT-NPD14 is depicted in FIG. 1. The downfield shifted peaks between 8.4-9.2 ppm are attributed to NPDI (10 NPDI protons for the half molecule). The peaks corresponding to the electron rich IDT core

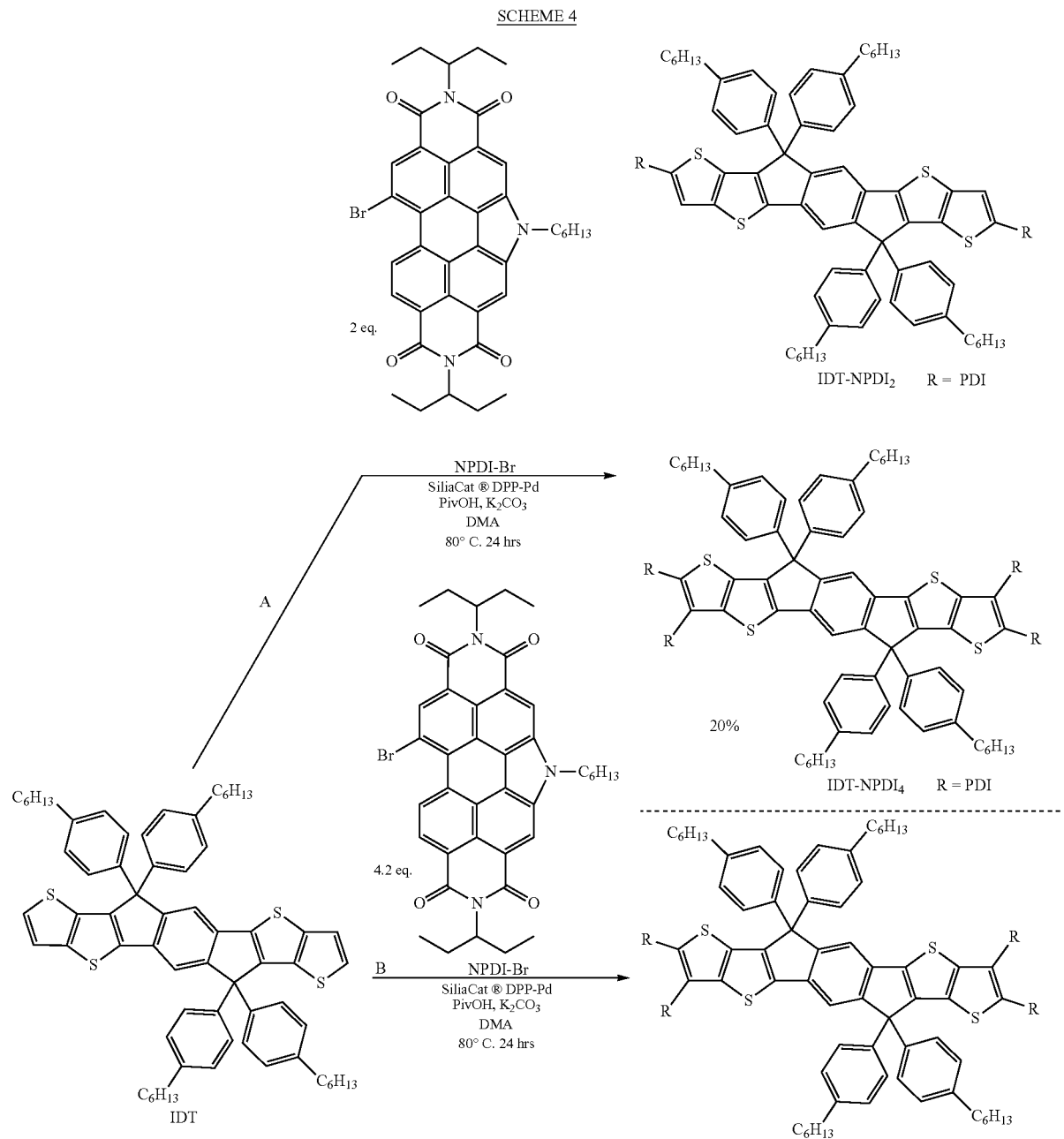

Figure 2A:
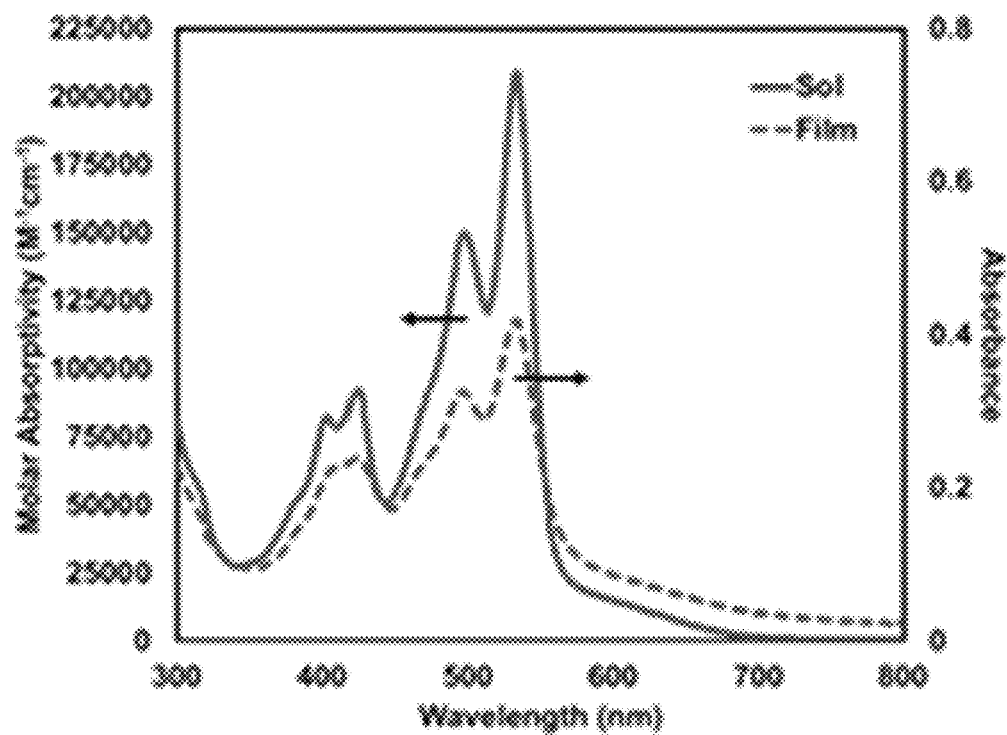
FIG. 2A illustrates the solution UV-Vis absorption (solid trace) and thin film UV-Vis absorption (dashed trace) of IDT-NPDI4.
Figure 2B:
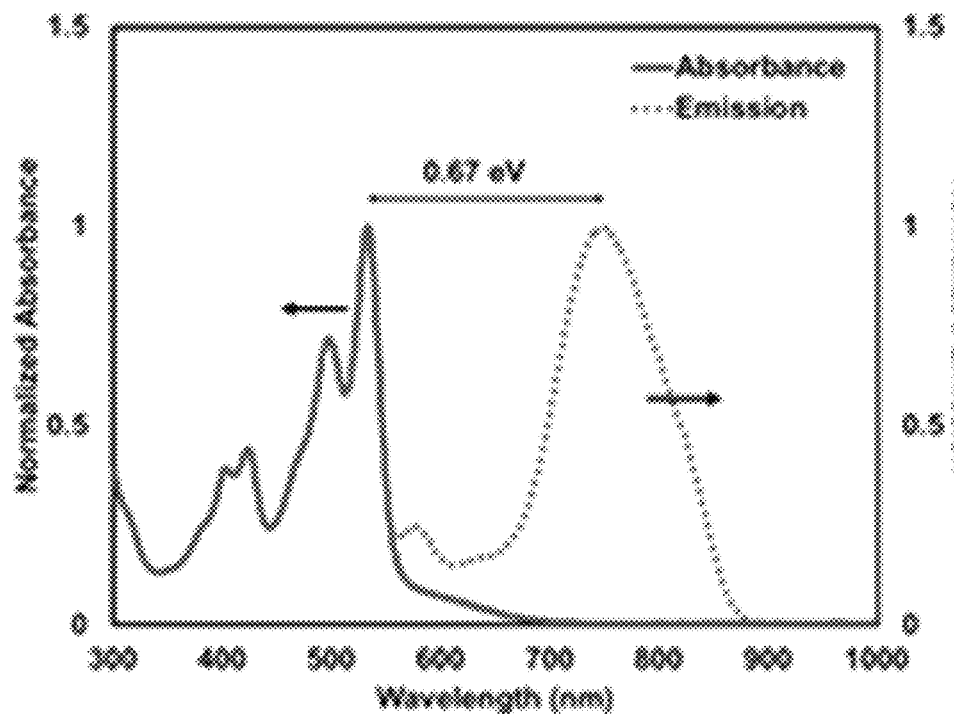
FIG. 2B illustrates the solution UV-Vis absorption (solid trace) versus florescence (dotted trace) of IDT-NPDI4. Solution measurements were performed in $CHCl_3$, film was spun cast from 100 µL of a 1% w/v solution of IDT-NPDI4 in $CHCl_3$ at 1500 RPM onto a 2×2 cm UV-ozone-cleaned glass substrate.

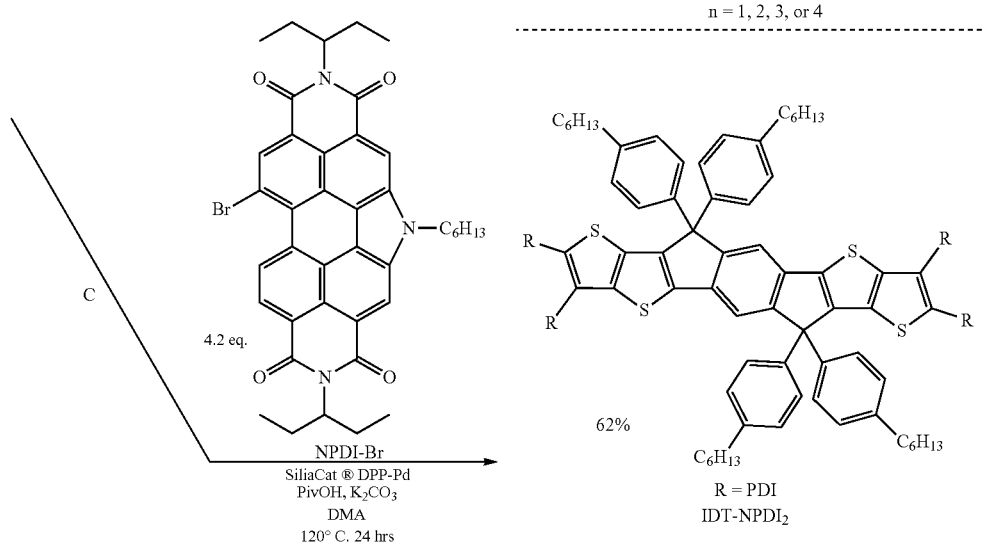

remain further upfield with the singlet at 7.37 ppm corresponding to the para protons on the central phenyl ring of the IDT core. The optical properties of IDT-NPDI4 were evaluated using UV-Vis spectroscopy (FIG. 2A, Table 1), photoluminescence spectroscopy (FIG. 2B, Table 1). As expected, with four PDI units, the UV-Vis profile is dominated by NPDI with a high molar absorptivity surpassing 200,000 M−1cm−1, which is approximately four times that observed for monomeric PDI species. The higher energy absorption from 350-440 nm is attributed to the IDT core. The lack of any significant lower energy absorption bands indicates that there is minimal electron delocalization between the IDT and NPDI units which can be expected due to the likelihood of large dihedral angles between the building blocks as a result of the inherent steric strains.

Figure 3A:
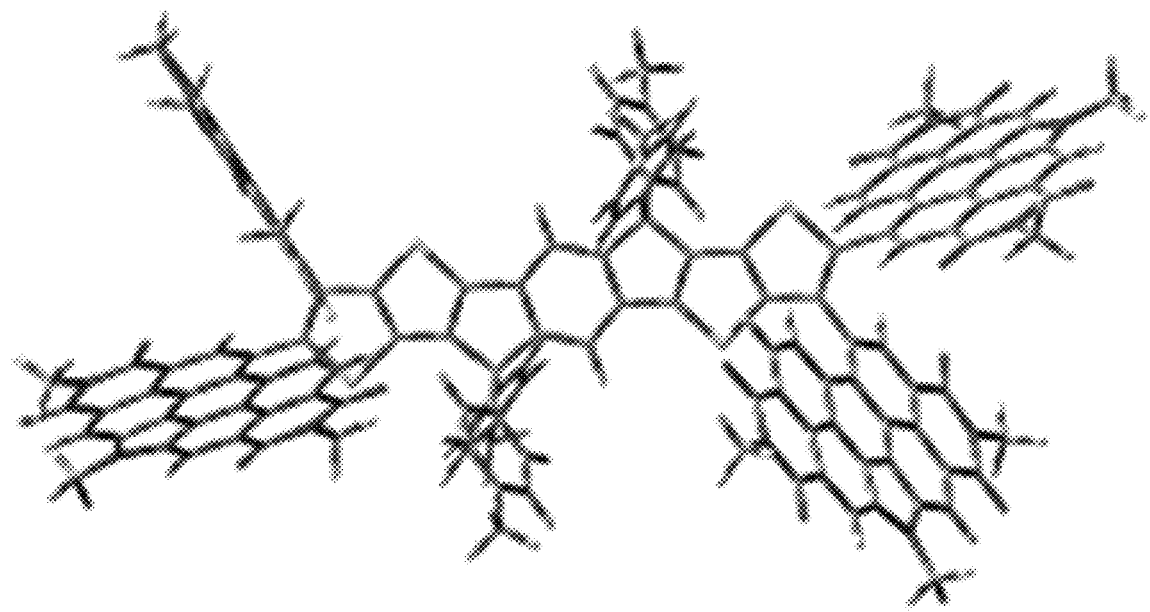
FIGS. 3A and 3B illustrate the optimized structure of IDT-NPDI4 face-on (A) and side-on (B) calculated using DFT at the B3LYP-6-31G(d,p) level of theory.
Figure 3B:
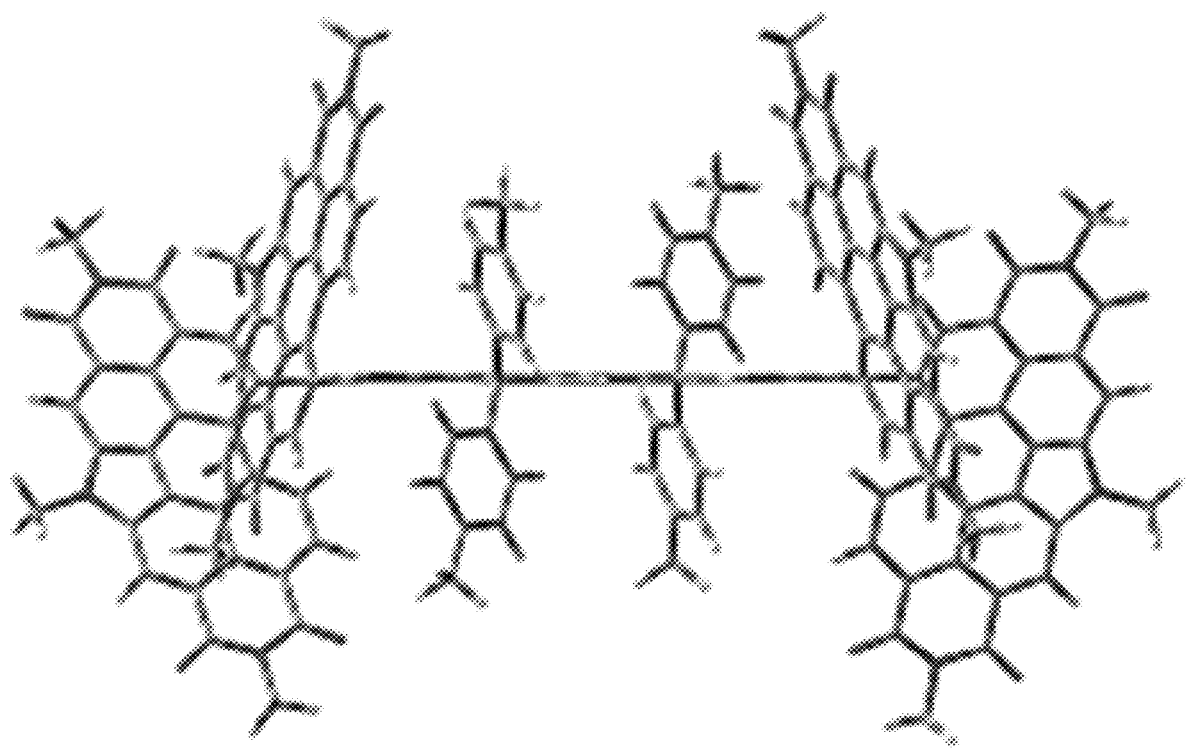

Large dihedral angles of 180° between the NPDI units and IDT core are observed for the theoretical optimized structure calculated by density functional theory (DFT) at the B3LYP-6-31G(d,p) level of theory. As can be seen in FIGS. 3A and 3B, the NPDI backbones in the calculated structure are orthogonal to that of IDT giving the molecule a butterfly-type shape.

Figure 4A:
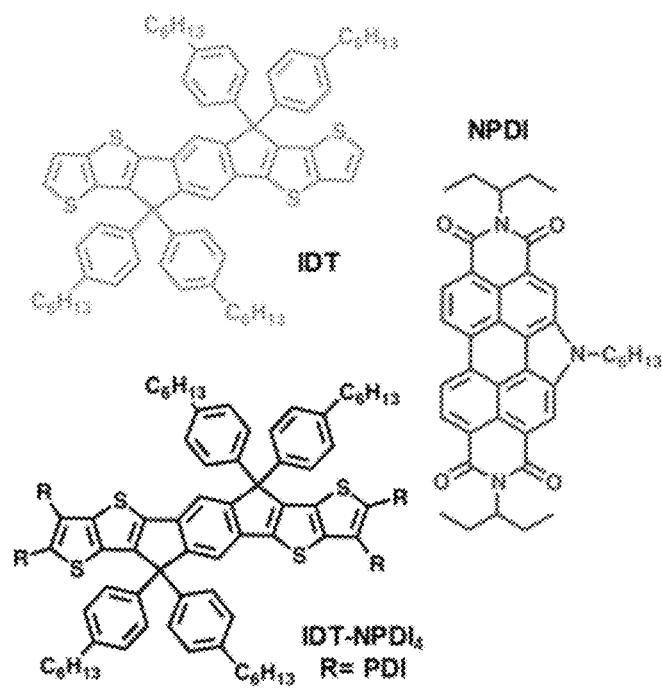
FIGS. 4A and 4B illustrate the normalized thin film ($CHCl_3$) absorption profiles of IDT (dotted trace 1), NPDI (dotted trace 2), and IDT-NPDI4 (solid trace).
Figure 4B:
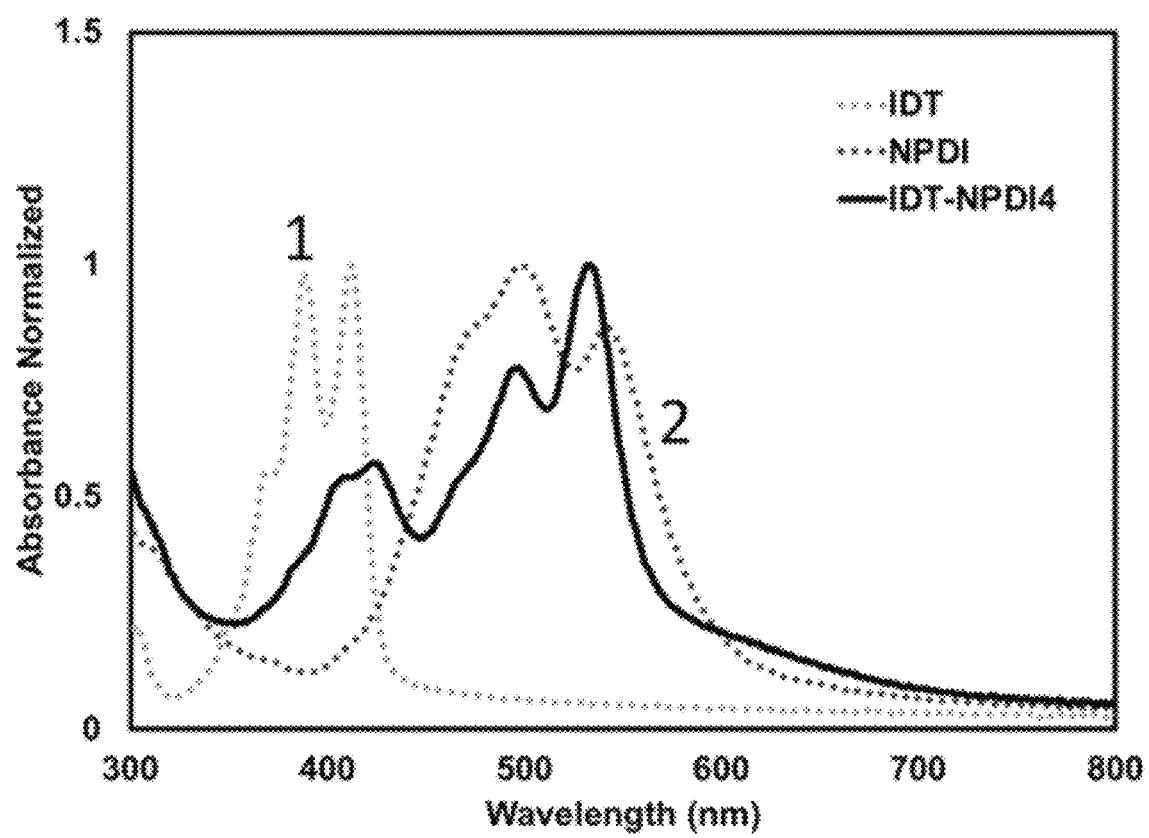

Minimal change in optical absorption is observed upon transitioning from solution to film suggesting no significant change in molecular organization from solution to solid state. Thin film UV-Vis spectra of the individual components (IDT and NPDI) of IDT-NPDI4 can be viewed in FIG. 4B and assist in the assignment of the optical transitions. The photoluminescence spectra show relatively large stokes shifts for IDT-PDI4 in both solution (0.67 eV) and solid state (0.64 eV). Typically, PDI compounds exhibit small stoke shifts so it is postulated that this large red-shifted emission observed may be the result of an intramolecular charge transfer state. Structures of IDT, NPDI and IDT-NPDI4 are shown in FIG. 4A.

Figure 5A:
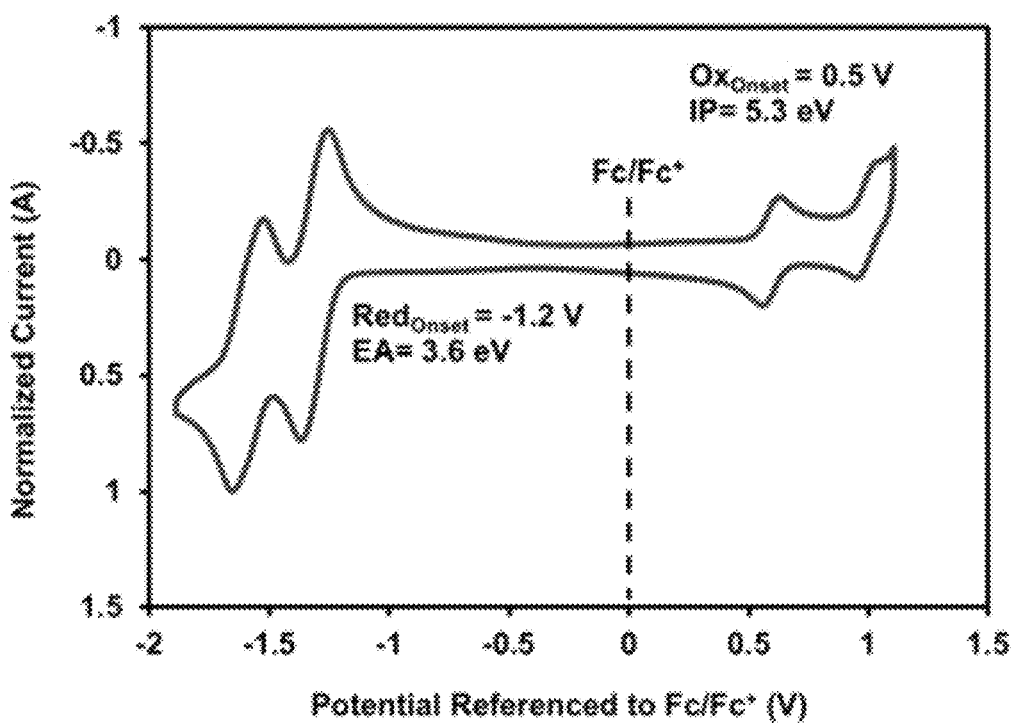
FIGS. 5A and 5B illustrate cyclic voltammograms.
Figure 5B:
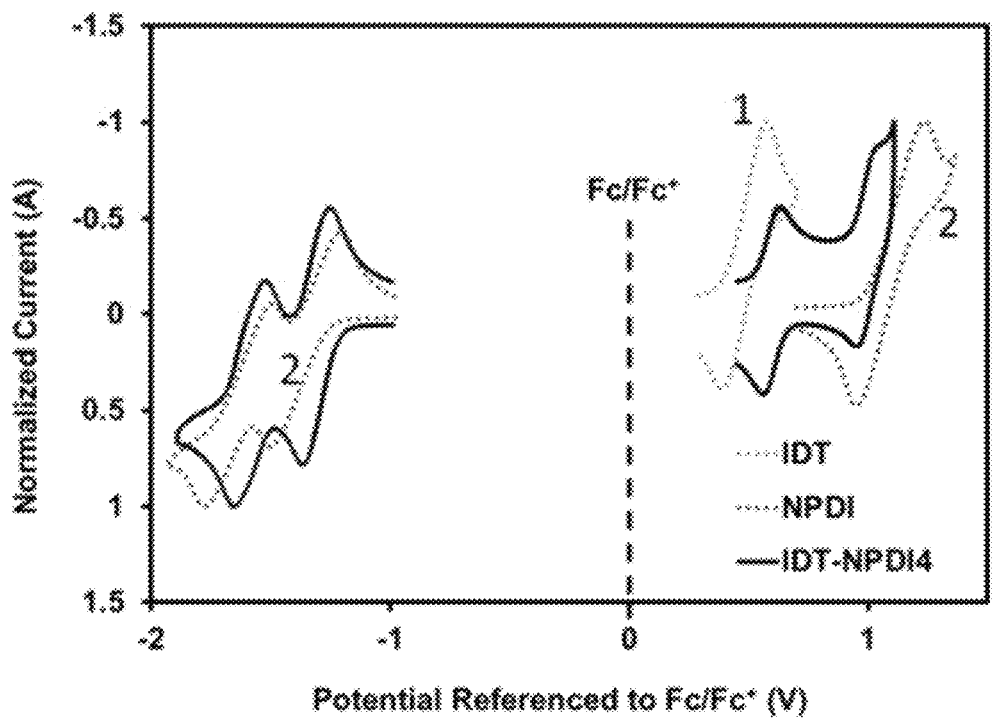

The electronic properties were investigated using cyclic voltammetry (FIGS. 5A and 5B, Table 2). IDT-NPDI4 shows stable ambipolar redox behaviour with two reversible oxidations, the first being attributed to IDT (E1/2=0.61 V) and the second NPDI (E1/2=1.00 V), and two reversible reductions attributed to NPDI (E1/2=−1.32 V, −1.59 V). The assignments of the oxidation and reduction waves are based on the overlaid cyclic voltammograms of IDT-PDI4 with its individual components, IDT and NPDI (FIG. 5B). The ionization potentials (IP) and electron affinities (EA) were estimated by correlating the onsets of oxidation and reduction, respectively, to the normal hydrogen electrode (NHE), assuming the IP of Fc/Fc+ to be 4.80 eV. The IP, dominated by the IDT core, was found to be 5.3 eV and the EA, dictated by the NPDI units, was calculated at 3.6 eV.

Figure 6A:
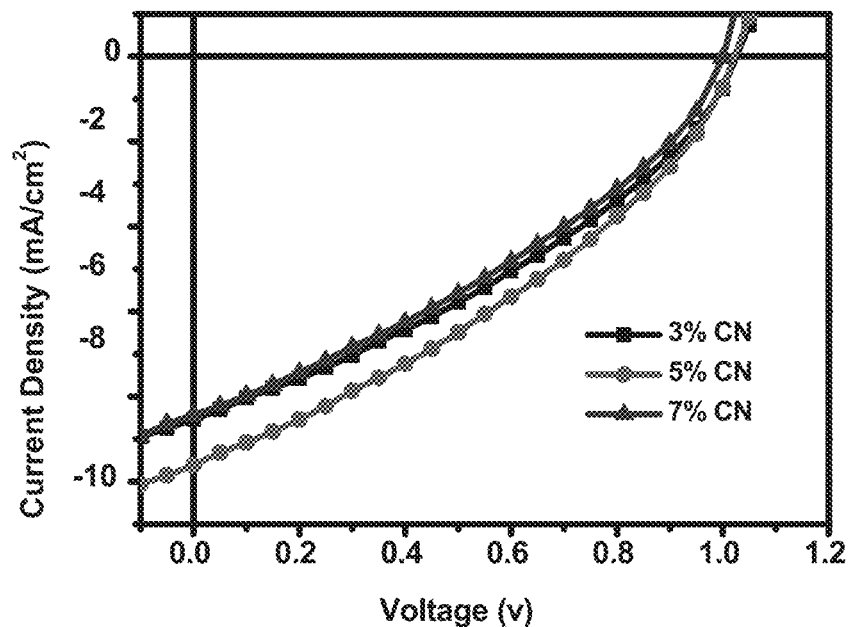
FIGS. 6A-6D show characterization of OSCs with a PTB7-Th: IDT-NPDI4 active layer.
Figure 6B:
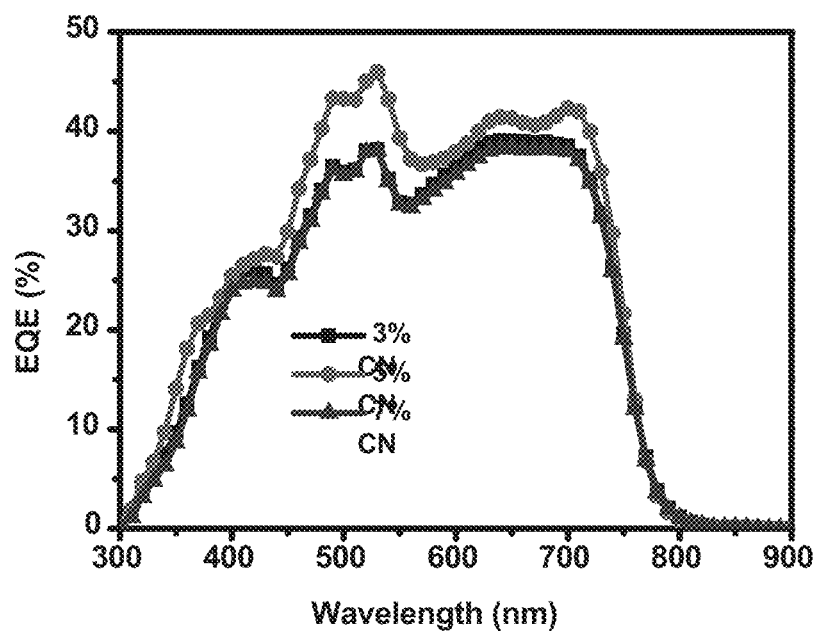
Figure 6C:
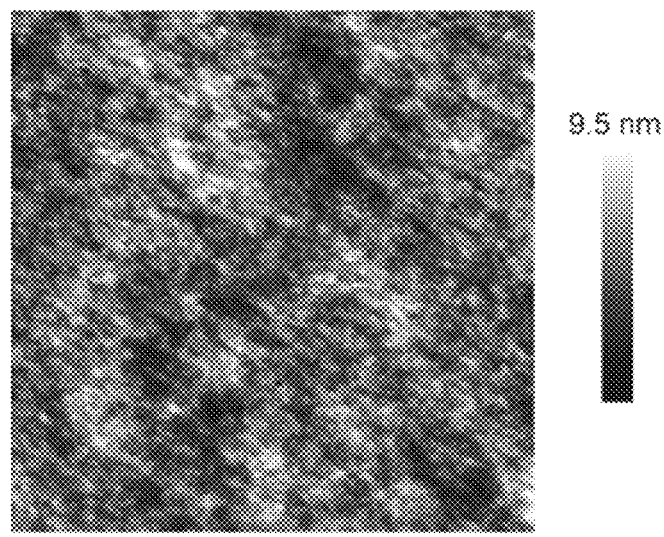
Figure 6D:
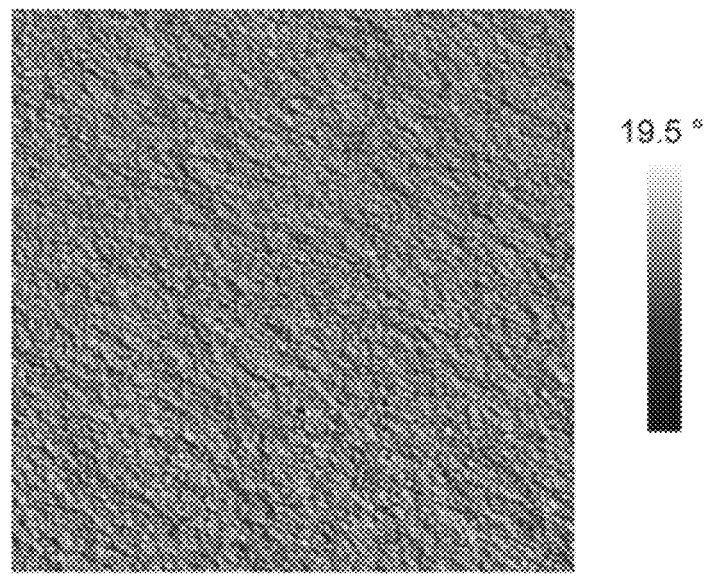
Figure 7A:
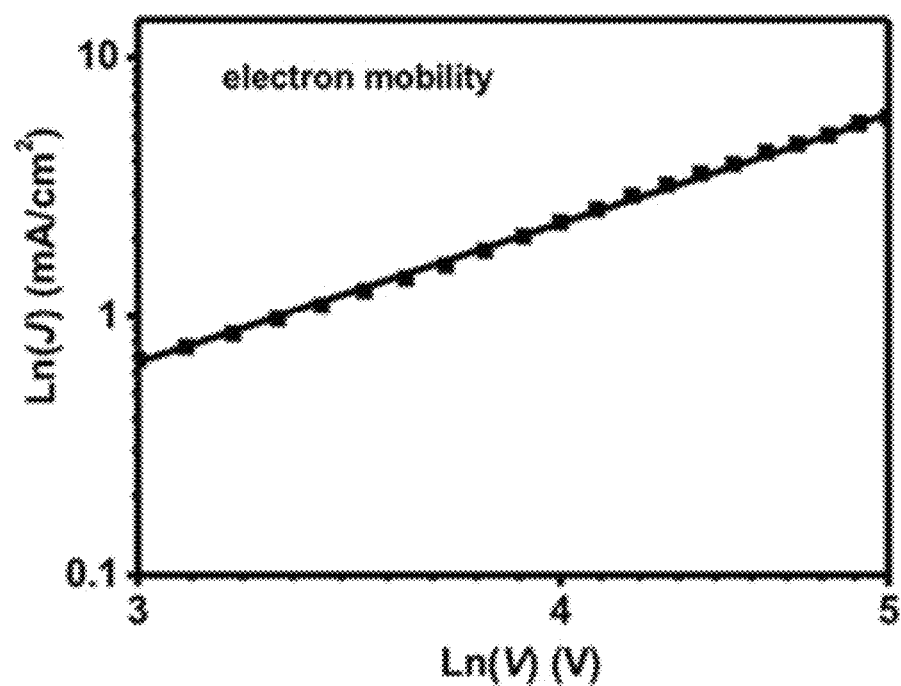
FIGS. 7A and B are space charge limited current (SCLC) measurement plots for electron and hole mobility, respectively.
Figure 7B:
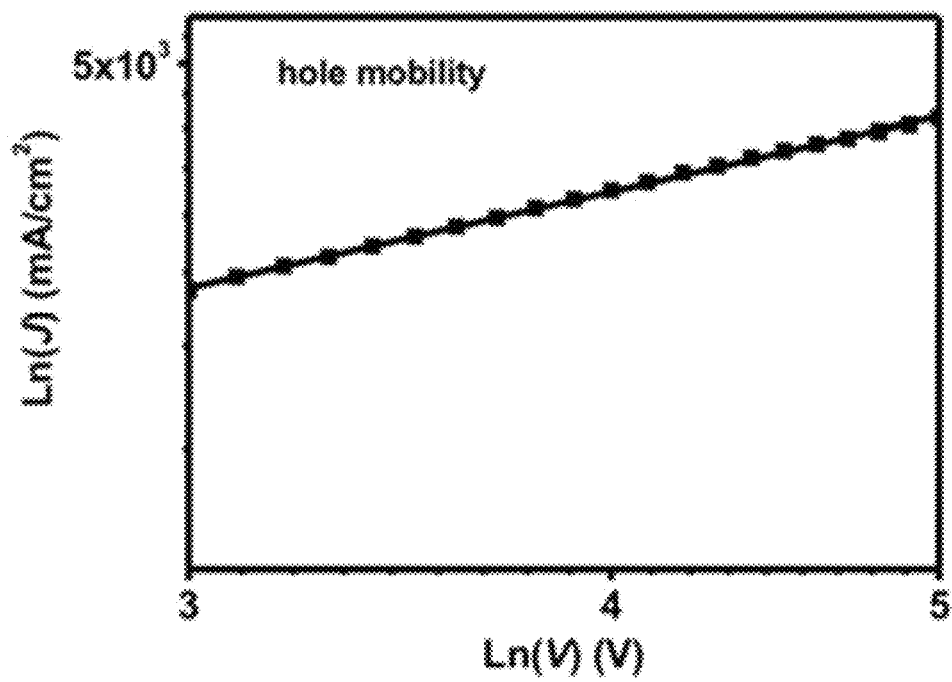

OSC devices were fabricated using the standard donor polymer PTB7-Th with the exemplary tetramer IDT-NPDI4 as the NFA. An inverted bulk heterojunction (BHJ) architecture was utilized with active layer processing from chlorobenzene with the solvent additive chloronaphthalene (CN), a common processing method found to improve device performance of PDI OSCs. OSC characterization and device metrics are detailed in FIGS. 6A-D and Table 3. The PTB7-Th:IDT-NPDI4-based OSCs showed a good photovoltaic response with devices reaching power conversion efficiencies (PCEs) of 3.4% using 5% v/v CN processing additive. As seen in FIG. 6A, the OCS produced high voltages (VOC) above 1V, but ultimately had modest currents (JSC) from 8-10 mA cm−2 and poor fill factors (FF). Photocurrent generation occurred from 300-800 nm with a maximum from 500-550 nm, which is where IDT-NPDI4 absorbs indicating its significant contribution to photocurrent generation (FIG. 6B). Investigation of the active layer morphology of the best OSC via atomic force microscopy (AFM, FIGS. 6C and 6D) revealed a very smooth film. The electron and hole mobility of the active layer was determined via the space charge limited current (SCLC) method and found to be 4.00×10−6 cm2V−1s−1 and 2.74×10−4 cm2V−1s−1, respectively (FIGS. 7A and B, respectively).

The unbalanced charge transport of the active layer is the primary cause of the lower FF and JSC in this case. Indeed, the shunt resistance is low indicating that free charge carriers are being generated, but not being collected fast enough. These results are quite encouraging as the JSC and FF can be improved through further active layer processing optimization.

TABLE 1

Tabulated optical absorption data

| | $\lambda_{max}$ abs (nm) | $\lambda_{onset}$ abs (nm) | Eg (eV) | $\varepsilon(\lambda_{max})$ (M$^{-1}$cm$^{-1}$) | $\lambda_{max}$ em (nm) | Stokes Shift (eV) |
|---|---|---|---|---|---|---|
| Solution | 533 | 568 | 2.2 | 209,803 | 748 | 0.67 |
| Film | 533 | 574 | 2.2 | | 732 | 0.64 |

TABLE 2

Tabulated electrochemical data

| Oxidation Potentials (V) | Ox$_{onset}$ (V) | IP (eV) | Reduction Potentials (V) | Red$_{onset}$ (V) | EA (eV) | Eg (eV) |
|---|---|---|---|---|---|---|
| 0.61, 1.00 | 0.50 | 5.3 | −1.32, −1.59 | −1.20 | 3.6 | 1.7 |

TABLE 3

Tabulated organic solar cell data

| CN (v/v) | $V_{OC}$ (V) | $J_{SC}$ (mA cm$^{-2}$) | FF | PCE |
|---|---|---|---|---|
| 3% | 1.03 | 8.53 | 0.35 | 3.03 |
| 5% | 1.02 | 9.62 | 0.35 | 3.41 |
| 7% | 1.00 | 8.44 | 0.34 | 2.90 |

Example 2: Synthetic Example

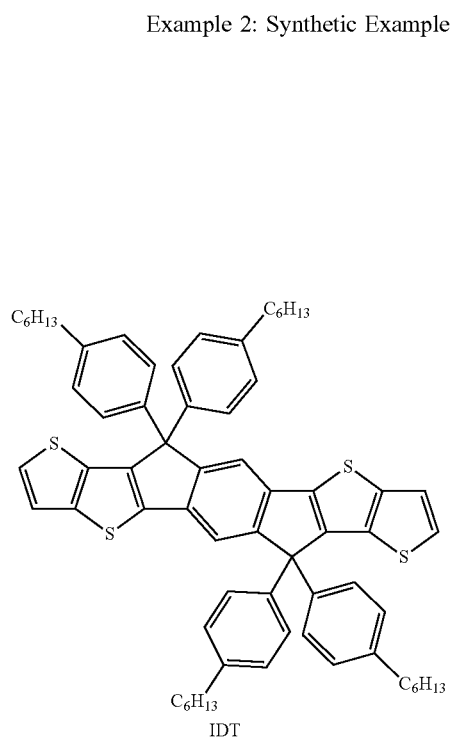

IDT

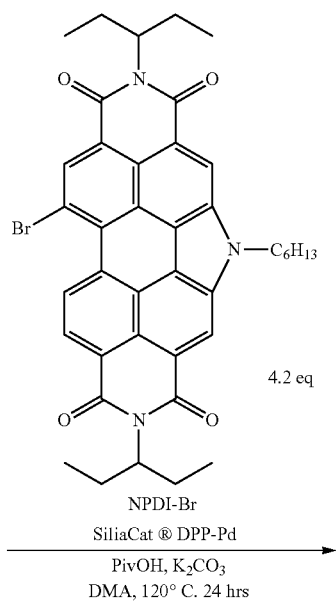

NPDI-Br $\xrightarrow{\text{SiliaCat} \circledR \text{ DPP-Pd}}_{\substack{\text{PivOH, K}_2\text{CO}_3 \\ \text{DMA, 120}° \text{C. 24 hrs}}}$ 4.2 eq

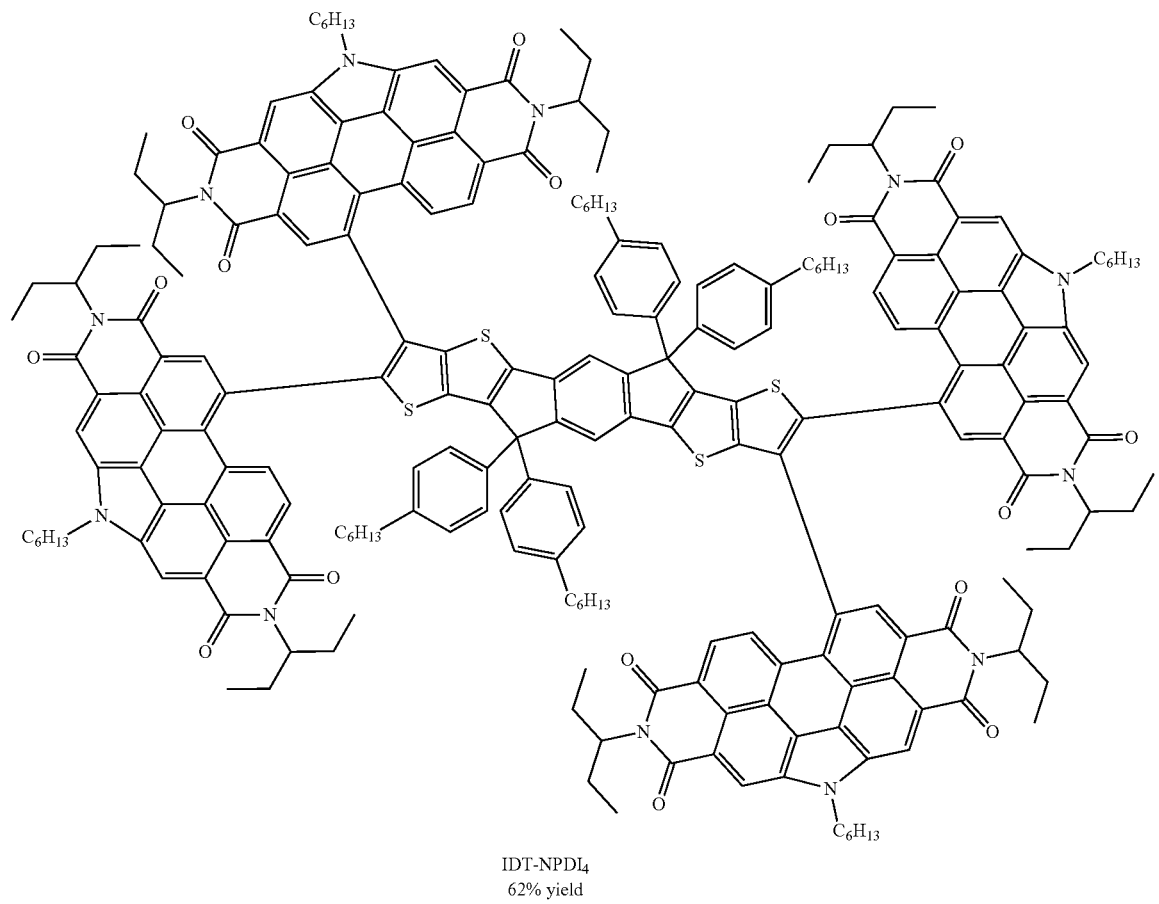

IDT-NPDI₄
62% yield

In a 5 mL pressure vial, IDT (0.025 g, 0.0245 mmol, 1 eq), PDI precursor NPDI-Br (0.075 mg, 0.106 mmol, 4.2 eq), SiliaCat® DPP-Pd (5 mol % Pd), pivalic acid (PivOH, 30 mol % with respect to IDT core), and potassium carbonate (0.015 g, 0.0109 mmol, 4.5 eq.) were added with a stir bar followed by the addition of anhydrous N,N'-dimethylacetamide (1 mL) solvent. The reaction mixture was sealed with a Teflon® cap under $N_2$ and heated at 120° C. in a LabArmor® bead bath for 24 hours. After 24 hours, the reaction mixture was poured into acetone (50 mL) and stirred overnight. The precipitated product was collected by filtration and the filtrate was discarded. The solid product was subsequently dissolved in dichloromethane and passed through a short neutral alumina plug to remove the silica-supported catalyst and any remaining inorganics. Upon removal of solvent, the resulting material was sonicated in EtOAc (ethyl acetate, 50 mL) before allowing it to stir at reflux for several hours. The resulting solution was allowed to cool to room temperature and the resulting material was subsequently filtered washing with EtOAc followed by acetone and isolated as a dark red powder yielding the desired product in 62% yield (0.055 g, 0.0156 mmol, 62% yield). It is believed that a small amount of tris-substituted compound was removed with the ethyl acetate washing procedure.

Example 3: Synthetic Example

Synthesis of TMS4Th4

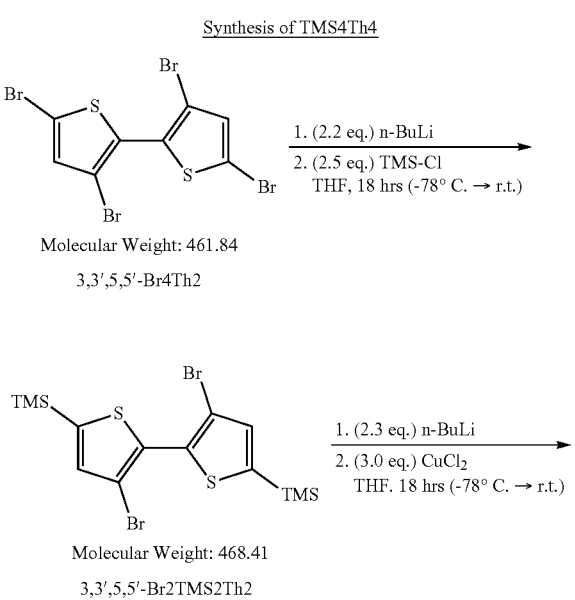

-continued

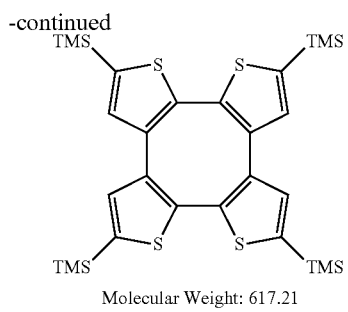

Molecular Weight: 617.21

TMS4Th4

Into a 250 mL Schlenk flask, add 3,3',5,5'-Br4Th2 (2.0 g, 4.16 mmol) and a stir-bar. Seal the flask with a new septum and complete three vacuum purge+$N_2$-backfill cycles on a Schlenk line. Once filled with $N_2$, close off the Schlenk line and disconnect. Cannula transfer dried THF (80 mL) into the Schlenk flask. Stir to dissolve 3,3',5,5'-Br4Th2 and then cool the reaction mixture to −78° C. Add n-BuLi (3.7 mL, 9.2 mmol) dropwise over 5 mins. Allow reaction mixture to stir for 1 hour. Add TMS-Cl (2.5 eq.) dropwise to the cooled solution. Allow reaction mixture to stir overnight. Cool the stirring reaction mixture (containing 3,3',5,5'-Br2TMS2Th2) to −78° C. Add nBuLi (4.0 mL, 9.8 mmol, 2.3 eq) for 5 mins. Allow reaction to stir for ~1 hour. Add $CuCl_2$ (1.70 g, 12.6 mmol, 3 eq) to the solution under a stream of $N_2$. Allow the reaction mixture to stir overnight. Quench the reaction with water (75 mL), then extract using $Et_2O$ (4×50 mL). Dry the $Et_2O$ extracts over $Na_2SO_4$. Filter away the drying agent, then concentrate the solvent by rotoevaporation. The resulting crude oil was purified by silica gel column chromatography (hexanes) to afford TMS4Th4 as a yellow solid (452 mg, 0.73 mmol, 35%).

Methods and materials for making precursors useful in this method can be found in Urieta-Mora et al. which is incorporated by reference herein in its entirety.

Deprotection of TMS4Th4

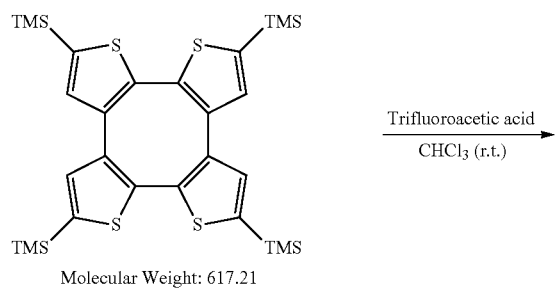

Molecular Weight: 617.21

TMS4Th4

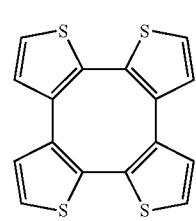

Molecular Weight: 328.48

Into a 100 mL round-bottomed flash, dissolve TMS4Th4 (0.30 g, 0.48 mmol) in minimal $CHCl_3$. Add TFA dropwise (4.5 equivalents), stir for ~15 mins, then quench the reaction by adding excess water. Extract the aqueous mixture with $CHCl_3$ (3×30 mL); wash these extracts with water (2×50 mL), and then dry organic extracts over $Na_2SO_4$. Filter the dried extracts through Celite and remove solvent under reduced pressure. Precipitate product Th4 from MeOH, and collect the resulting pale yellow solid by vacuum filtration (128 mg, 0.47 mmol, 98%).

Synthesis/Purification of Th4PDI4

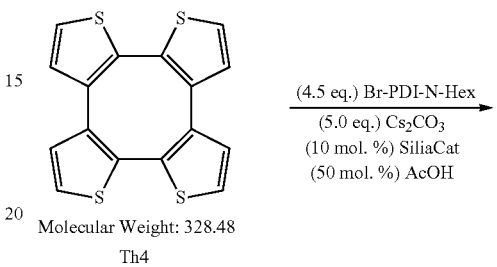

Molecular Weight: 328.48

Th4

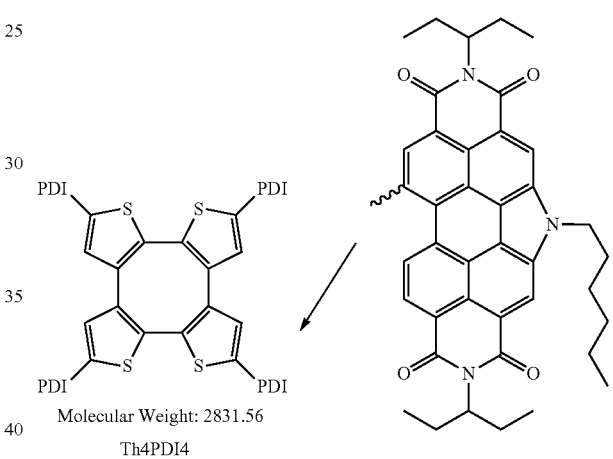

Molecular Weight: 2831.56

Th4PDI4

Into a 10 mL microwave vial, add Th4 (1 eq., 32.8 mg, 0.10 mmol), Br-PDI—N-Hex (4.5 eq., 320 mg, 0.45 mmol), $Cs_2CO_3$ (5 eq., 163 mg, 0.50 mmol), and SiliaCat-Pd-DPP (0.1 eq., 40 mg, 0.01 mmol) and a stir-bar. Seal the vial and purge with $N_2$ for 30 minutes. Dried dimethylacetamide (6 mL) was cannula transferred into the vial and the reaction mixture was sparged with $N_2$ for an additional 15 minutes. Acetic acid (0.5 eq., 3 mg, 0.05 mmol) was injected into the reaction vial and then the vial was placed in a 120° C. bead bath for 24 hours. The reaction mixture was then poured into methanol (150 mL), stirred for 1 hour, and vacuum filtered. The resulting crude solid was dissolved in $CHCl_3$ and adhered to silica. The silica adhered compound was placed on top of more silica and the plug was eluted using: i) Hexanes:Acetone (4:1), then ii) $CHCl_3$, and lastly iii) $CHCl_3$+5% MeOH. The $CHCl_3$ fraction was further purified by column chromatography using $CHCl_3$. After removing solvent under reduced pressure, the crimson red solid Th4PDI4 was precipitated in methanol and collected by vacuum filtration. (187 mg, 0.07 mmol, 70%).

$^1$H NMR, and HR-Maldi-MS of the resultant product are consistent with TH4PDI4 of structure:

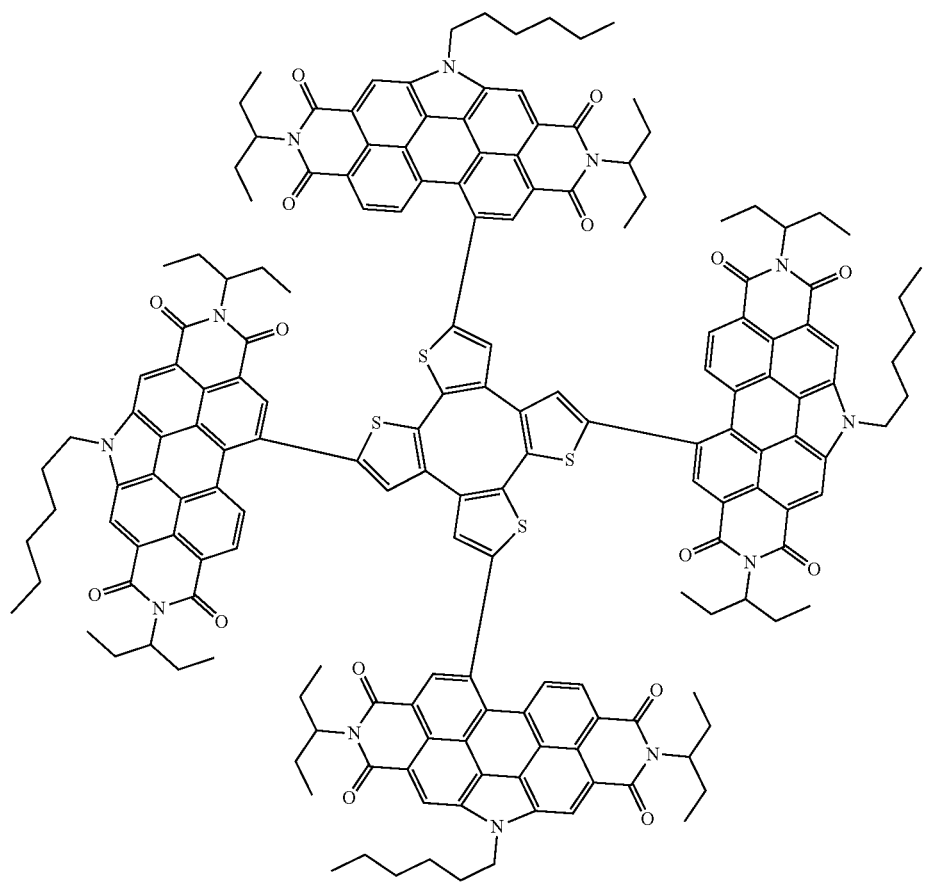 [SMILES: CCCCCCn1c2cc3c(=O)n(C(CC)CC)c(=O)c4ccc5c6c(-c7cc8c(s7)-c7sc(-c9cc%10c(=O)n(C(CC)CC)c(=O)c%11cc%12c%13c(c9c9ccc%14c(=O)n(C(CC)CC)c(=O)c%15cc(c%13c9c%14%15)n%12CCCCCC)c%10%11)cc7-c7cc(-c9cc%10c(=O)n(C(CC)CC)c(=O)c%11cc%12c%13c(c9c9ccc%14c(=O)n(C(CC)CC)c(=O)c%15cc(c%13c9c%14%15)n%12CCCCCC)c%10%11)sc7-c7sc(-c9cc%10c(=O)n(C(CC)CC)c(=O)c%11cc%12c%13c(c9c9ccc%14c(=O)n(C(CC)CC)c(=O)c%15cc(c%13c9c%14%15)n%12CCCCCC)c%10%11)cc7-8)cc7c(=O)n(C(CC)CC)c(=O)c8cc1c(c6c78)c2c5c43]

REFERENCES

1. T. W. Kelley, P. F. Baude, C. Gerlach, D. E. Ender, D. Muyres, M. A. Haase, D. E. Vogel and S. D. Theiss, Chem. Mater., 2004, 16, 4413-4422.
2. A. Facchetti, Chem. Mater., 2011, 23, 733-758.
3. T. P. Kaloni, P. K. Giesbrecht, G. Schreckenbach and M. S. Freund, Chem. Mater., 2017, 29, 10248-10283.
4. J. Roncali, Chem. Rev., 1997, 97, 173-206.
5. P. M. Beaujuge and J. R. Reynolds, Chem. Rev., 2010, 110, 268-320.
6. Y.-J. Cheng, S.-H. Yang and C.-S. Hsu, Chem. Rev., 2009, 109, 5868-5923.
7. G. Zhang, J. Zhao, P. C. Y. Chow, K. Jiang, J. Zhang, Z. Zhu, J. Zhang, F. Huang and H. Yan, Chem. Rev., 2018, 118, 3447-3507.
8. C. Sekine, Y. Tsubata, T. Yamada, M. Kitano and S. Doi, Sci. Technol. Adv. Mater., 2014, 15, 034203.
9. D. J. Burke and D. J. Lipomi, Energy Environ. Sci., 2013, 6, 2053-2066.
10. R. Po and J. Roncali, J. Mater. Chem. C, 2016, 4, 3677-3685.
11. A. Wadsworth, M. Moser, A. Marks, M. S. Little, N. Gasparini, C. J. Brabec, D. Baran and I. McCulloch, Chem. Soc. Rev., 2018, DOI:10.1039/C7CS00892A.
12. H. Bohra and M. Wang, J. Mater. Chem. A, 2017, 5, 11550-11571.
13. J.-R. Pouliot, F. Grenier, J. T. Blaskovits, S. Beaupre and M. Leclerc, Chem. Rev., 2016, 116, 14225-14274.
14. T. Bura, J. T. Blaskovits and M. Leclerc, J. Am. Chem. Soc., 2016, 138, 10056-10071.
15. D. J. Schipper and K. Fagnou, Chem. Mater., 2011, 23, 1594-1600.
16. F. Grenier, K. Goudreau and M. Leclerc, J. Am. Chem. Soc., 2017, 139, 2816-2824.
17. J. Zhang, L. Zhu and Z. Wei, Small Methods, 2017, 1, 1700258.
18. A. F. Eftaiha, J.-P. Sun, I. G. Hill and G. C. Welch, J. Mater. Chem. A, 2013, 2, 1201-1213.
19. S. M. McAfee, J. M. Topple, I. G. Hill and G. C. Welch, J. Mater. Chem. A, 2015, 3, 16393-16408.
20. P. Cheng, G. Li, X. Zhan and Y. Yang, Nat. Photonics, 2018, 12, 131-142.
21. J. Hou, O. Inganas, R. H. Friend and F. Gao, Nat. Mater., 2018, 17, 119-128.
22. C. Yan, S. Barlow, Z. Wang, H. Yan, A. K.-Y. Jen, S. R. Marder and X. Zhan, Nat. Rev. Mater., 2018, 3, 18003.
23. J. Zhang, H. S. Tan, X. Guo, A. Facchetti and H. Yan, Nat. Energy, DOI: 10.1038/s41560-018-0181-5.
24. Y. Lin, J. Wang, Z.-G. Zhang, H. Bai, Y. Li, D. Zhu and X. Zhan, Adv. Mater., 2015, 27, 1170-1174.
25. W. Zhao, D. Qian, S. Zhang, S. Li, O. Ingants, F. Gao and J. Hou, Adv. Mater., 28, 4734-4739.
26. J. Liu, S. Chen, D. Qian, B. Gautam, G. Yang, J. Zhao, J. Bergqvist, F. Zhang, W. Ma, H. Ade, O. Ingants, K. Gundogdu, F. Gao and H. Yan, Nat. Energy, 2016, 1, 16089(1)-16089(7).
27. D. Meng, D. Sun, C. Zhong, T. Liu, B. Fan, L. Huo, Y. Li, W. Jiang, H. Choi, T. Kim, J. Y. Kim, Y. Sun, Z. Wang and A. J. Heeger, J. Am. Chem. Soc., 2016, 138, 375-380.
28. D. Sun, D. Meng, Y. Cai, B. Fan, Y. Li, W. Jiang, L. Huo, Y. Sun and Z. Wang, J. Am. Chem. Soc., 2015, 137, 11156-11162.

29. Q. Wu, D. Zhao, A. M. Schneider, W. Chen and L. Yu, J. Am. Chem. Soc., 2016, 138, 7248-7251.
30. Z. Luo, T. Liu, W. Cheng, K. Wu, D. Xie, L. Huo, Y. Sun and C. Yang, J. Mater. Chem. C, 2018, 6, 1136-1142.
31. Q. Wu, D. Zhao, J. Yang, V. Sharapov, Z. Cai, L. Li, N. Zhang, A. Neshchadin, W. Chen and L. Yu, Chem. Mater., 2017, 29, 1127-1133.
32. J. Zhang, Y. Li, J. Huang, H. Hu, G. Zhang, T. Ma, P. C. Y. Chow, H. Ade, D. Pan and H. Yan, J. Am. Chem. Soc., 2017, 139, 16092-16095.
33. A. D. Hendsbee, J.-P. Sun, W. K. Law, H. Yan, I. G. Hill, D. M. Spasyuk and G. C. Welch, Chem. Mater., 2016, 28, 7098-7109.
34. Y. Lin, J. Wang, S. Dai, Y. Li, D. Zhu and X. Zhan, Adv. Energy Mater., 4, 1400420.
35. S. Li, W. Liu, C.-Z. Li, T.-K. Lau, X. Lu, M. Shi and H. Chen, J. Mater. Chem. A, 2016, 4, 14983-14987.
36. Z.-F. Chang, Y. Cai, K.-K. Liu, X.-X. Song, J.-J. Liu, X. Liu, Y. Sun, R. bo Zhang and J.-L. Wang, Dyes Pigments, 2017, 147, 31-39.
37. S. M. McAfee, S. V. Dayneko, A. D. Hendsbee, P. Josse, P. Blanchard, C. Cabanetos and G. C. Welch, J. Mater. Chem. A, 2017, 5, 11623-11633.
38. A.-J. Payne, S. Li, S. V. Dayneko, C. Risko and G. C. Welch, Chem. Commun., 2017, 53, 10168-10171.
39. A.-J. Payne, S. M. McAfee and G. C. Welch, Chem. Pap., 2017, 1-6.
40. T. A. Welsh, A. Laventure and G. C. Welch, Molecules, 2018, 23, 931.
41. A. E. Rudenko and B. C. Thompson, J. Polym. Sci. Part Polym. Chem., 2015, 53, 135-147.
42. W. Li and T. Michinobu, Polym. Chem., 2016, 7, 3165-3171.
43. F. Lombeck, F. Marx, K. Strassel, S. Kunz, C. Lienert, H. Komber, R. Friend and M. Sommer, Polym. Chem., 2017, 8, 4738-4745.
44. S. V. Dayneko, A. D. Hendsbee and G. C. Welch, Small Methods, 2018, 2, 1800081.
45. J. Zhang, Y. Li, J. Huang, H. Hu, G. Zhang, T. Ma, P. C. Y. Chow, H. Ade, D. Pan and H. Yan, J. Amer. Chem. Soc., 2017, 139(45), 16092-16095.
46. J. Urieta-Mora et al. (2019) J. Mater. Chem. C, 7:6656.
47. A.-J. Payne et al. (2018) Chem. Commun. 54:11443-11446.
48. T. A. Welsh et al. (2019) New J. Chem. 43:9333-9337.

We claim:

1. An oligomeric PDI compound of formula:

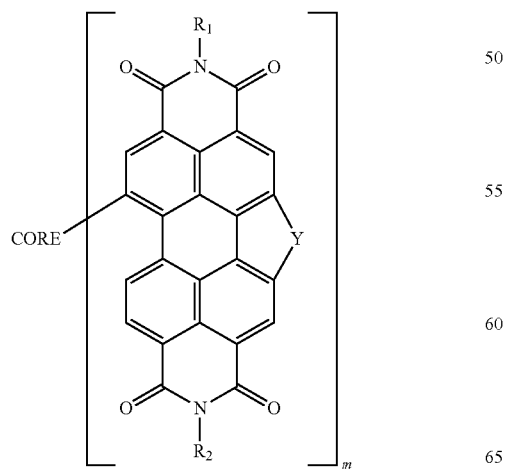

wherein:

m is an integer of 4-10;

Y is S, Se or N—$R_3$, $R_1$ and $R_2$ are the same or different and are each independently selected from alkyl groups having 1-30 carbon atoms;

$R_3$ is the same as or different from $R_1$ and $R_2$ and is selected from alkyl groups having 1-30 carbon atoms;

CORE is selected from the group consisting of the moieties C1-C40:

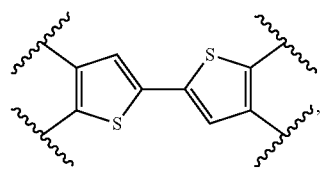

C1

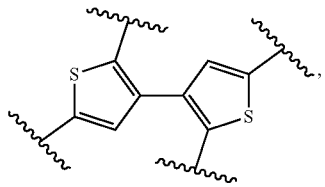

C2

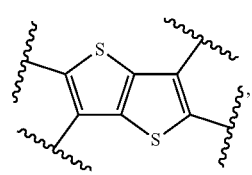

C3

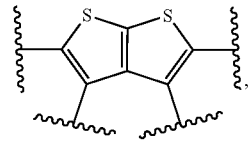

C4

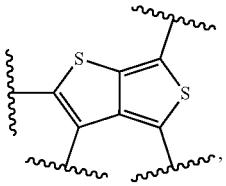

C5

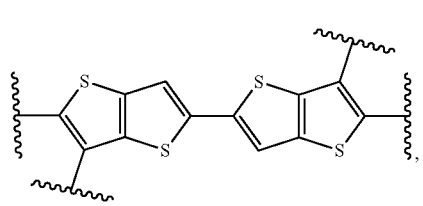

C6

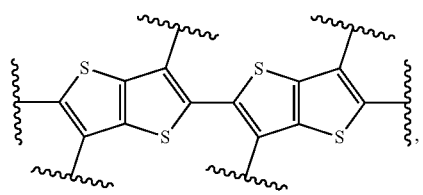

C7

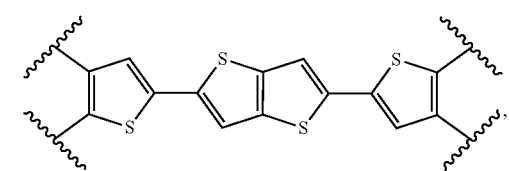
C8
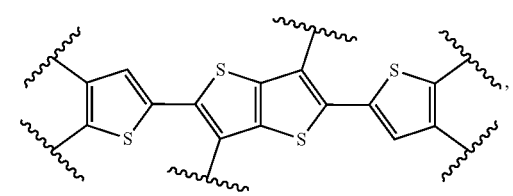
C9
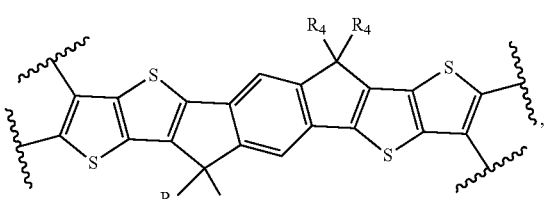
C10
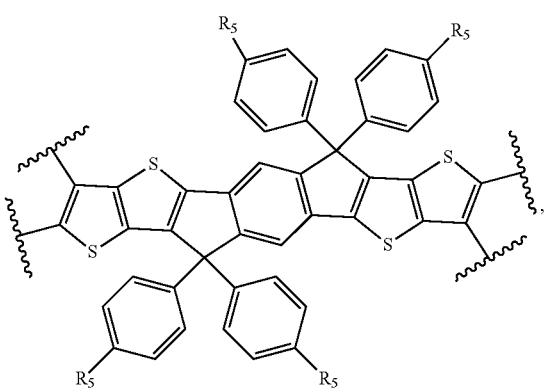
C11
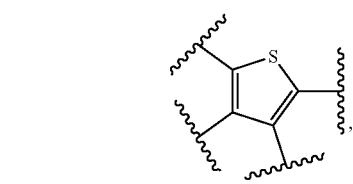
C12
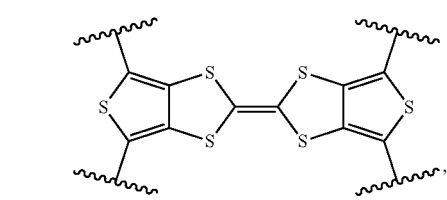
C13
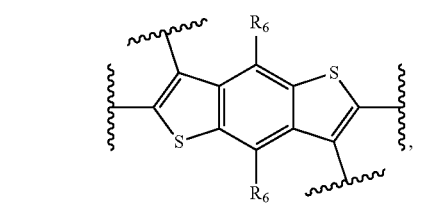
C14
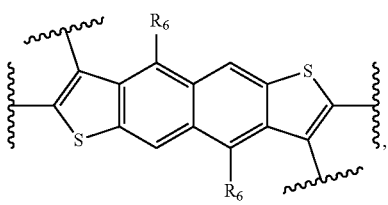
C15
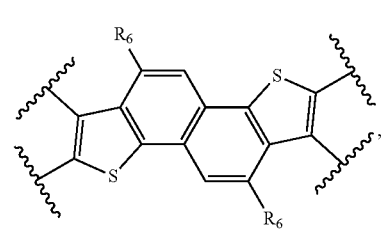
C16
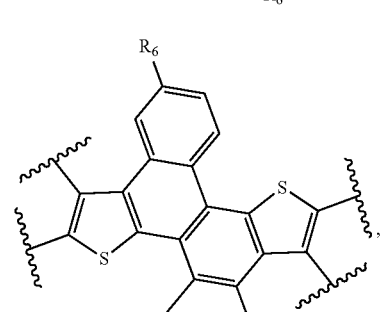
C17
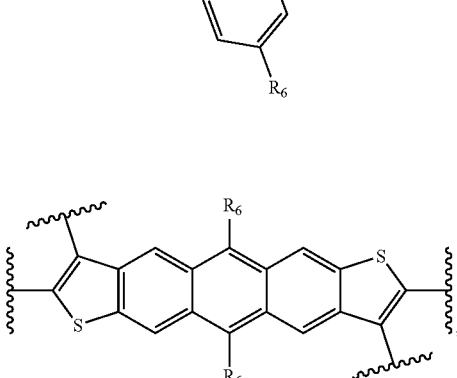
C18
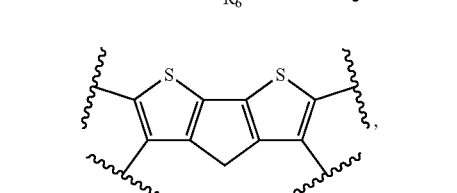
C19a
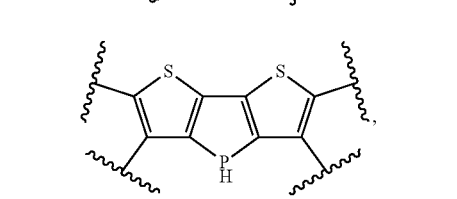
C19b
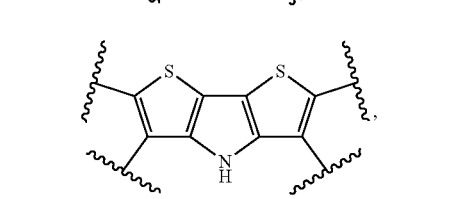
C19c

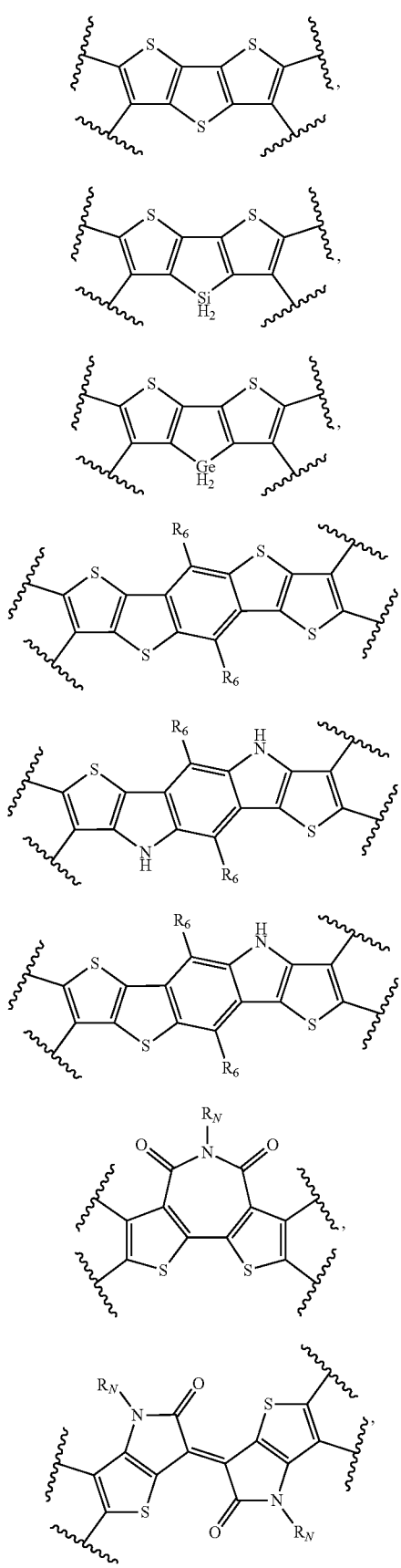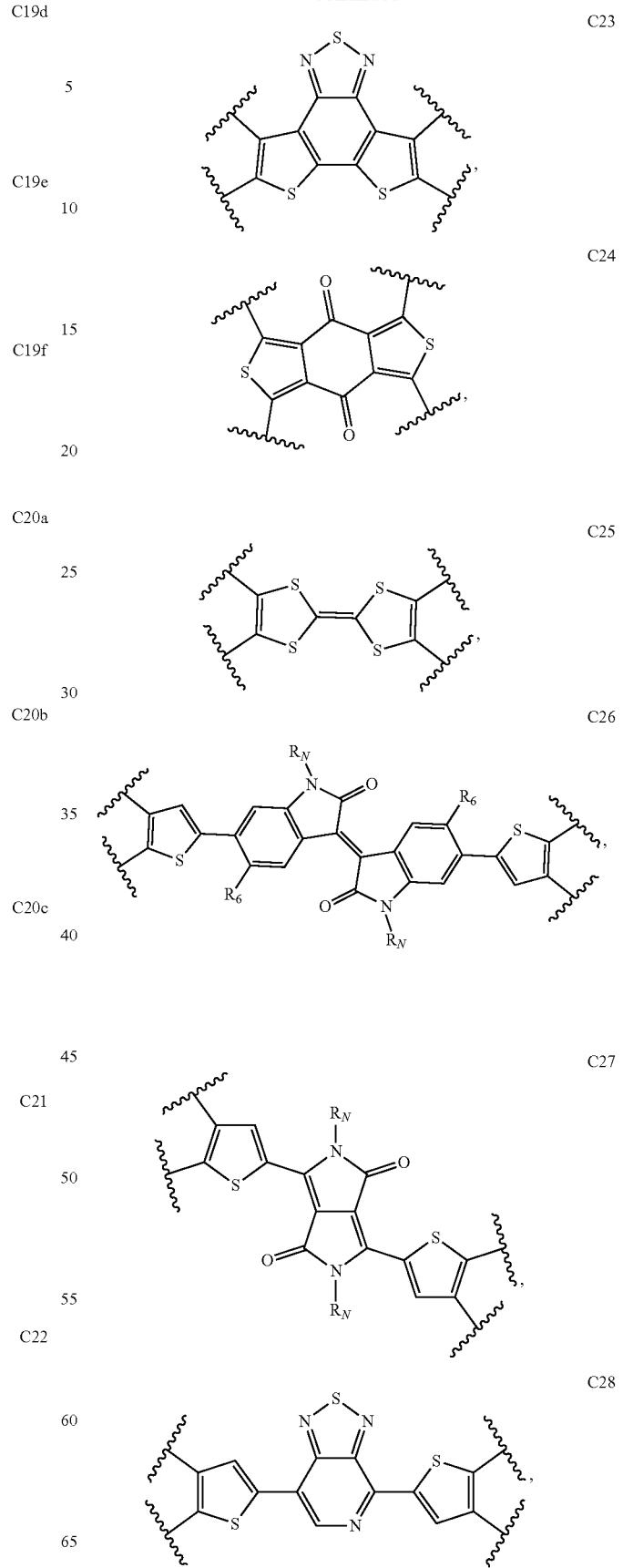

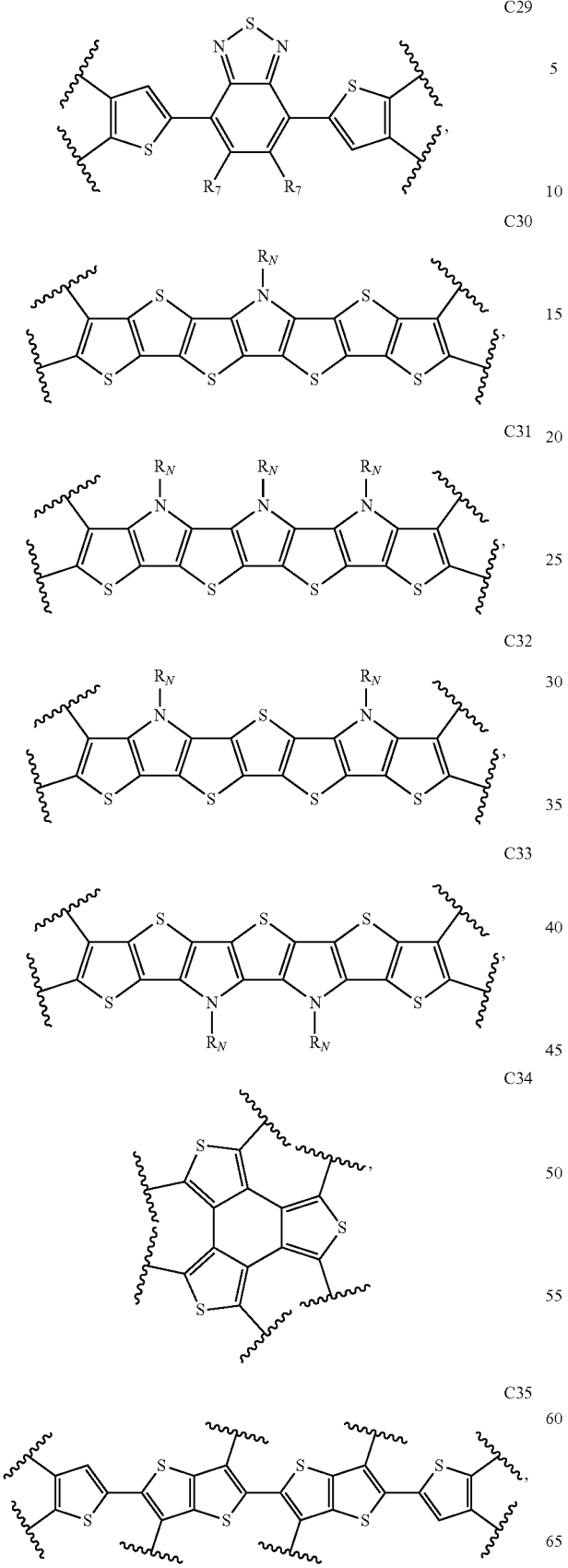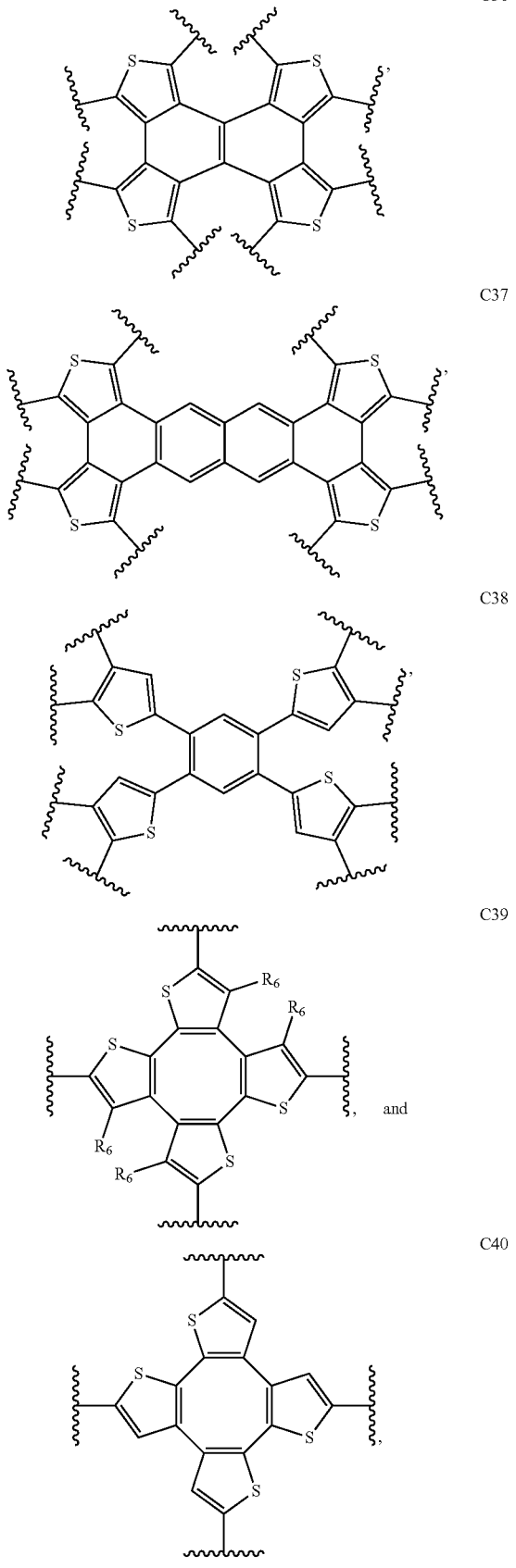

wherein:

each $R_4$ is independently selected from hydrogen, an alkyl group having 1-30 carbon atoms, an alkoxy group having 1-30 carbon atoms, an optionally-substituted aryl group, an optionally-substituted heteroaryl group;

each $R_5$ is independently selected from hydrogen, halogen, CN, an alkyl group having 1-30 carbon atoms, an alkoxy group having 1-30 carbon atoms;

each $R_6$ is independently selected from hydrogen, halogen, CN, an optionally-substituted phenyl group, an optionally-substituted benzyl group, an alkyl group having 1-30 carbon atoms and an alkoxy group having 1-30 carbon atoms;

each $R_7$ is independently selected from hydrogen, halogen, CN, an optionally-substituted phenyl group, an optionally-substituted benzyl group, an alkyl group having 1-30 carbon atoms and an alkoxy group having 1-30 carbon atoms;

each $R_N$ is selected from hydrogen, an alkyl group having 1-30 carbon atoms, an aryl group and an arylalkyl group; and where optional substitution is substitution with one or more halogen, CN, an alkyl group having 1-30 carbon atoms, or an alkoxy group having 1-30 carbon atoms.

2. The oligomeric PDI compound of claim 1, wherein the CORE is:

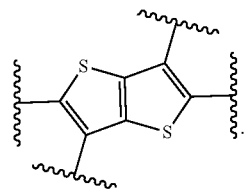 [SMILES: *c1sc2c(*)c(*)sc2c1*]

3. The oligomeric PDI compound of claim 1, wherein the CORE is:

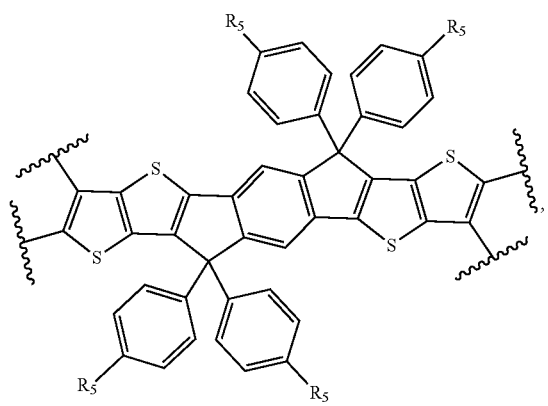

where each $R_5$ is independently selected from hydrogen, halogen, CN, an alkyl group having 1-30 carbon atoms, and an alkoxy group having 1-30 carbon atoms.

4. The oligomeric PDI compound of claim 3, wherein each $R_5$ is independently hydrogen or an alkyl group having 1-12 carbon atoms.

5. The oligomeric PDI compound of claim 1, wherein the CORE is:

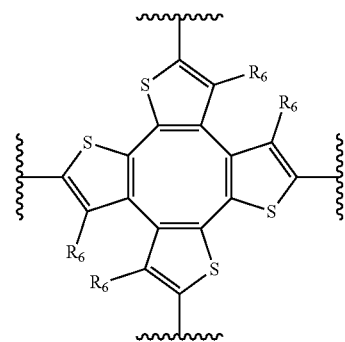

and each $R_6$ is independently selected from hydrogen, halogen, CN, an optionally-substituted phenyl group, an optionally-substituted benzyl group, an alkyl group having 1-30 carbon atoms, and an alkoxy having 1-30 carbon atoms.

6. The oligomeric PDI compound of claim 5, wherein $R_6$ is hydrogen or an alkyl group having 1-12 carbon atoms.

7. A tetrameric PDI compound of formula:

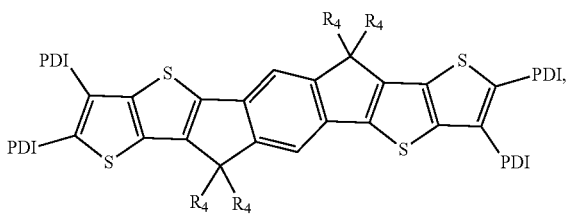

where:

each $R_4$ is independently selected from H, an alkyl group having 1-30 carbon atoms, an alkoxy group having 1-30 carbon atoms, an optionally-substituted aryl group and an optionally-substituted heteroaryl group, where optional substitution is substitution with one or more halogen, CN, alkyl group having 1-30 carbon atoms or alkoxy group having 1-30 carbon atoms; and PDI has formula:

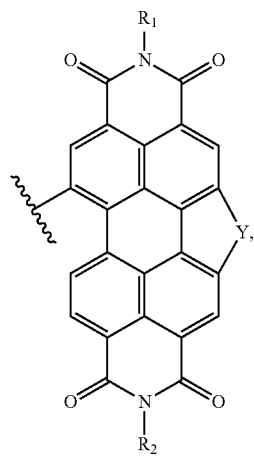

where:
Y is S, Se or N—R$_3$,
R$_1$ and R$_2$ are the same or different and are each independently selected from alkyl groups having 1-30 carbon atoms, and
R$_3$ is the same or different from R$_1$ and R$_2$ and is selected from alkyl groups having 1-30 carbon atoms.

8. The tetramer of claim 7, wherein each R$_4$ is an optionally-substituted aryl group.

9. The tetramer of claim 7, wherein each R$_4$ is an optionally-substituted phenyl group.

10. An electronic device employing an electron acceptor, wherein the electron acceptor is one or more PDI oligomeric compounds of claim 1.

11. The device of claim 10, which is an organic solar cell, an organic thin film transistor or a redox flow battery.

12. A method for making an oligomeric PDI compound which employs direct (hetero)arylation (DHA), wherein one or more equivalents of a PDI precursor are reacted with 1 equivalent of a CORE precursor, where the CORE precursor has four or more C—H bonds that are active for DHA.

13. The method of claim 12, wherein four or more equivalents of the PDI precursor are reacted with 1 equivalent of the CORE precursor.

14. A method for making an oligomeric PDI compound which employs direct (hetero)arylation (DHA), wherein one or more equivalents of a PDI precursor are reacted with 1 equivalent of a CORE precursor, where the CORE precursor has four or more C—H bonds that are active for DHA, where the oligomeric compound is a compound of claim 1.

15. The oligomeric PDI compound of claim 1, wherein R$_1$ and R$_2$ are the same or different and are each independently selected from alkyl groups having 1-12 carbon atoms; and
R$_3$ is the same as or different from R$_1$ and R$_2$ and is selected from alkyl groups having 1-12 carbon atoms.

16. The oligomeric PDI compound of claim 15, wherein each alkyl or alkoxy group has 1-12 carbon atoms.

17. The oligomeric PDI compound of claim 7,
wherein:
each Y is —NR$_3$;
each R$_1$ and R$_2$ are the same and are selected from alkyl groups having 3-12 carbon atoms;
each R$_3$ is the same as or different from R$_1$ and R$_2$ and is selected from alkyl groups having 3-12 carbon atoms; and
each R$_4$ is an optionally-substituted aryl group or an optionally-substituted heteroaryl group.

18. The oligomeric PDI compound of claim 17,
wherein: each R$_3$ is n-hexyl, each R$_1$ and each R$_2$ are 3-pentyl, and each R$_4$ is 4-n-alkyl-substituted phenyl.

19. The oligomeric PDI compound of claim 5, wherein each R$_6$ is hydrogen.

20. The oligomeric PDI compound of claim 19,
wherein:
each Y is —NR$_3$;
each R$_1$ and R$_2$ are the same and are selected from alkyl groups having 3-12 carbon atoms; and
each R$_3$ is the same as or different from R$_1$ and R$_2$ and is selected from alkyl groups having 3-12 carbon atoms.

21. The oligomeric PDI compound of claim 20,
wherein: each R$_3$ is n-hexyl, each R$_1$ is 3-pentyl and each R$_2$ is 3-pentyl.

22. The oligomeric PDI compound of claim 1 of formula:

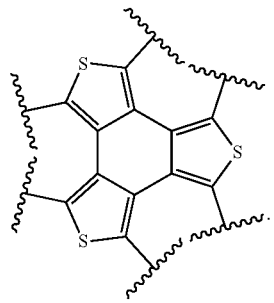 [SMILES: *c1sc(*)c2c1c1c(*)sc(*)c1c1c(*)sc(*)c21]

23. The oligomeric PDI compound of claim 22,
wherein:
each Y is —NR$_3$;
each R$_1$ and R$_2$ are the same and are selected from alkyl groups having 3-12 carbon atoms;
each R$_3$ is the same as or different from R$_1$ and R$_2$ and is selected from alkyl groups having 3-12 carbon atoms; and
each R$_4$ is an optionally-substituted aryl group or an optionally-substituted heteroaryl group.

24. The oligomeric PDI compound of claim 23,
wherein: each R$_3$ is n-hexyl, each R$_1$ and each R$_2$ are 3-pentyl, and each R$_4$ is 4-n-alkyl-substituted phenyl.

25. An electronic device employing an electron acceptor, wherein the electron acceptor is one or more PDI oligomeric compounds of claim 1.

26. An electronic device employing an electron acceptor, wherein the electron acceptor is one or more PDI oligomeric compounds of claim 5.

27. An electronic device employing an electron acceptor, wherein the electron acceptor is one or more PDI oligomeric compounds of claim 7.

28. An electronic device employing an electron acceptor, wherein the electron acceptor is one or more PDI oligomeric compounds of claim 22.

* * * * *